(12) United States Patent
Van Ostrand et al.

(10) Patent No.: US 12,352,713 B2
(45) Date of Patent: Jul. 8, 2025

(54) ORGANIC AND/OR INORGANIC MATERIAL TEST SYSTEM USING DIFFERENTIAL DRIVE-SENSE CIRCUITS

(71) Applicant: SIGMASENSE, LLC., Wilmington, DE (US)

(72) Inventors: Daniel Keith Van Ostrand, Leander, TX (US); Richard Stuart Seger, Jr., Belton, TX (US); Gerald Dale Morrison, Redmond, WA (US); Patrick Troy Gray, Cedar Park, TX (US); Phuong Huynh, Fairfax, VA (US); Timothy W. Markison, Mesa, AZ (US); Patricia M. Healy, Phoenix, AZ (US)

(73) Assignee: SIGMASENSE, LLC., Austin, TX (US)

( * ) Notice: Subject to any disclaimer, the term of this patent is extended or adjusted under 35 U.S.C. 154(b) by 982 days.

(21) Appl. No.: 17/446,574

(22) Filed: Aug. 31, 2021

(65) Prior Publication Data
US 2022/0057349 A1 Feb. 24, 2022

Related U.S. Application Data

(63) Continuation-in-part of application No. 16/730,118, filed on Dec. 30, 2019, now Pat. No. 11,935,397.

(51) Int. Cl.
*G01N 27/02* (2006.01)
(52) U.S. Cl.
CPC .................................. *G01N 27/02* (2013.01)
(58) Field of Classification Search
CPC ... G01N 27/02; G01N 33/4833; G01N 27/026
(Continued)

(56) References Cited

U.S. PATENT DOCUMENTS 5,437,178 A   8/1995   Esin et al.
6,218,972 B1  4/2001   Groshong
(Continued)

FOREIGN PATENT DOCUMENTS

CN   104536627 A   4/2015
CN   107771273 A   3/2018
(Continued)

OTHER PUBLICATIONS

Baker; How delta-sigma ADCs work, Part 1; Analog Applications Journal; Oct. 1, 2011; 6 pgs.
(Continued)

*Primary Examiner* — Giovanni Astacio-Oquendo
(74) *Attorney, Agent, or Firm* — Garlick & Markison; Timothy W. Markison; Patricia M. Healy

(57) ABSTRACT

An organic and inorganic material test system includes at least one test container, a first and second set of electrodes embedded in the at least one test container, a set of transmit circuits coupled to the first set of electrodes, and a set of differential drive-sense circuits (DDSCs) coupled to the second set of electrodes. A first transmit circuit coupled to a first electrode is operable to produce a first transmit signal at a first frequency for transmission through contents of a first test container. A first DDSC coupled to a second electrode of the first test container includes a pair of drive-sense circuits (DSCs) and an output operational amplifier. The pair of DSCs are operable to generate receive signals at the first frequency. The output operational amplifier compares receive signals to produce a signal representative of the contents with respect to positioning of the first and second electrodes.

11 Claims, 42 Drawing Sheets

(58) Field of Classification Search
USPC .................................. 324/650, 649, 600
See application file for complete search history.

(56) References Cited

U.S. PATENT DOCUMENTS

| | | |
|---|---|---|
| 6,665,013 B1 | 12/2003 | Fossum et al. |
| 7,476,233 B1 | 1/2009 | Wiener et al. |
| 7,528,755 B2 | 5/2009 | Hammerschmidt |
| 8,031,094 B2 | 10/2011 | Hotelling |
| 8,089,289 B1 | 1/2012 | Kremin et al. |
| 8,279,180 B2 | 10/2012 | Hotelling et al. |
| 8,547,114 B2 | 10/2013 | Kremin |
| 8,625,726 B2 | 1/2014 | Kuan |
| 9,201,547 B2 | 12/2015 | Elias |
| 9,351,653 B1 | 5/2016 | Harrison |
| 2003/0052657 A1 | 3/2003 | Koernle et al. |
| 2005/0235758 A1 | 10/2005 | Kowal et al. |
| 2011/0063154 A1 | 3/2011 | Hotelling et al. |
| 2011/0298745 A1 | 12/2011 | Souchkov |
| 2012/0287431 A1* | 11/2012 | Matsiev ............... G01N 27/026 356/306 |
| 2013/0021294 A1 | 1/2013 | Maharyta et al. |
| 2013/0278447 A1 | 10/2013 | Kremin |
| 2014/0346058 A1* | 11/2014 | Robitzki ........ G01N 33/48707 204/403.01 |
| 2016/0188049 A1 | 6/2016 | Yang et al. |
| 2018/0157354 A1 | 6/2018 | Blondin et al. |
| 2018/0202955 A1* | 7/2018 | Brun ................. G01N 27/021 |
| 2018/0275824 A1 | 9/2018 | Li |
| 2018/0364861 A1 | 12/2018 | Gray |
| 2019/0216358 A1* | 7/2019 | Gregory ............. G01N 27/026 |

FOREIGN PATENT DOCUMENTS

| | | |
|---|---|---|
| CN | 110325293 A | 10/2019 |
| EP | 2284637 A1 | 2/2011 |

OTHER PUBLICATIONS

Brian Pisani, "Digital Filter Types in Delta-Sigma ADCs", Application Report SBAA230, May 2017, pp. 1-8, Texas Instruments Incorporated, Dallas, Texas.
China National Intellectual Property Administration; First Office Action; Application No. 202080090673.4; Nov. 20, 2023; 12 pgs.
European Patent Office; Extended European Search Report; Application No. 19853507.2; Jun. 13, 2023; 7 pgs.

* cited by examiner

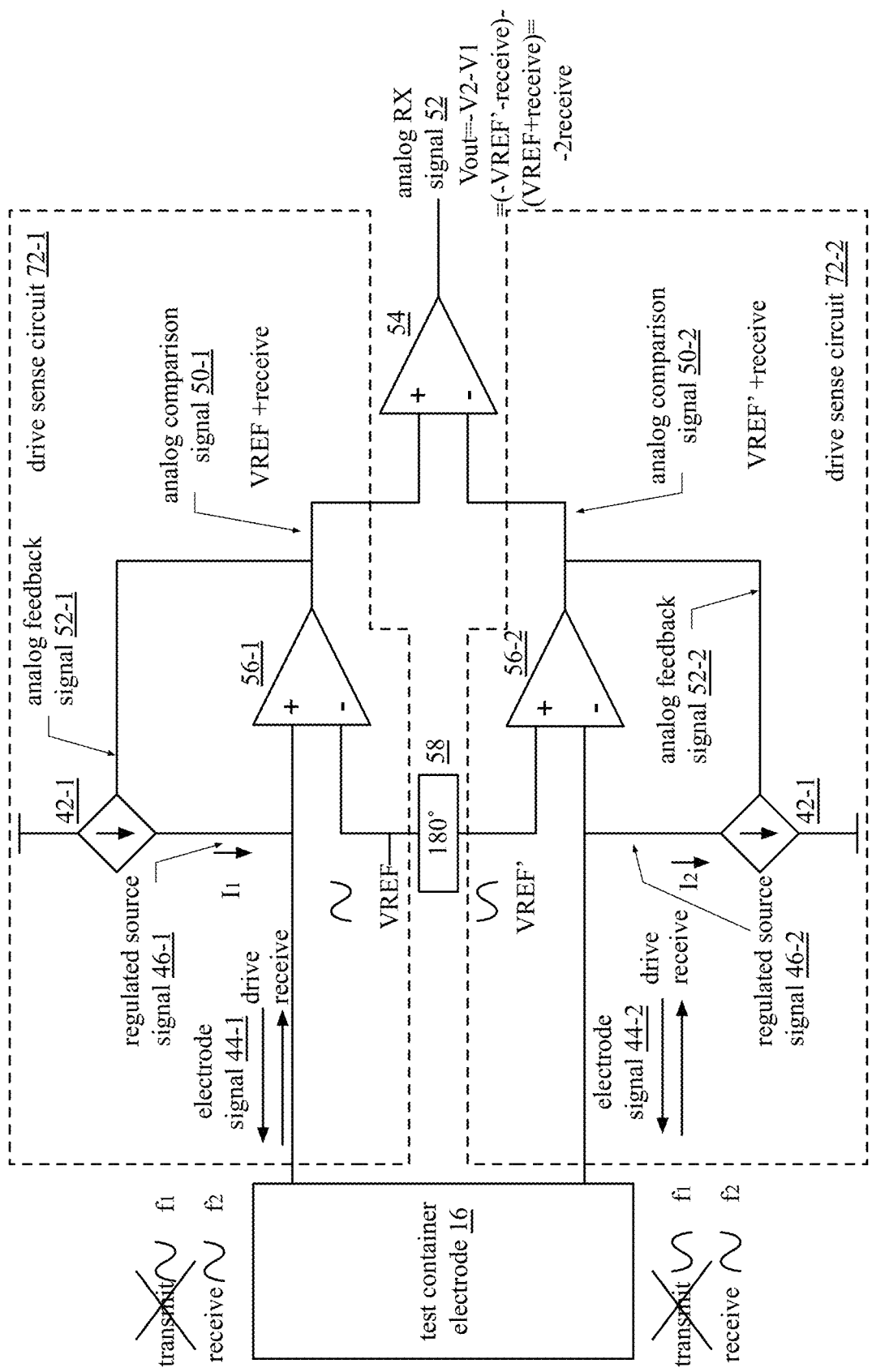
FIG.5 "receive only" differential drive-sense circuit (DDSC) 40

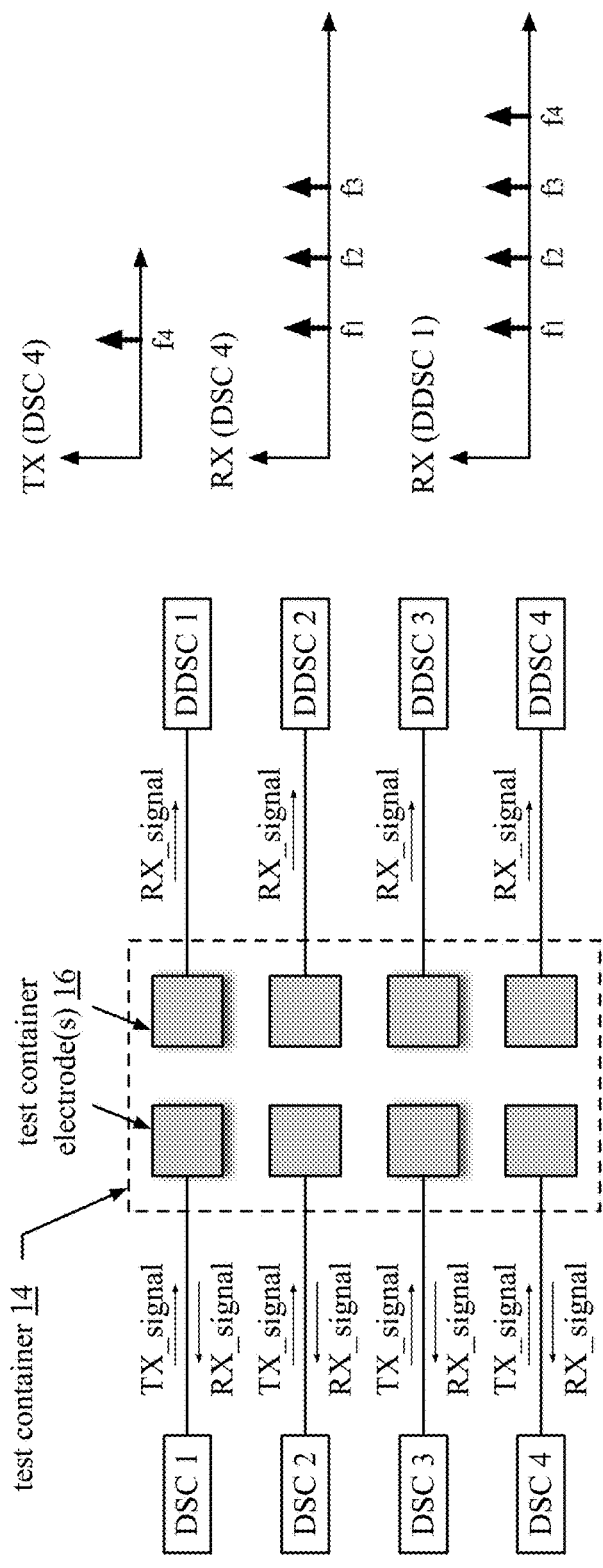
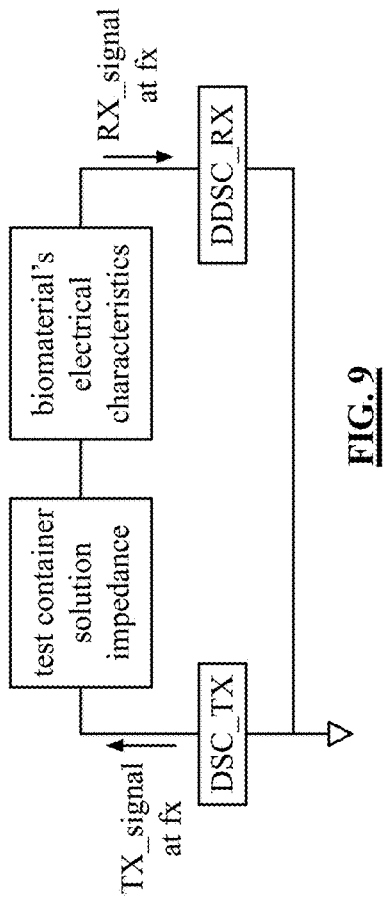
FIG. 6
FIG. 7
FIG. 8
FIG. 9

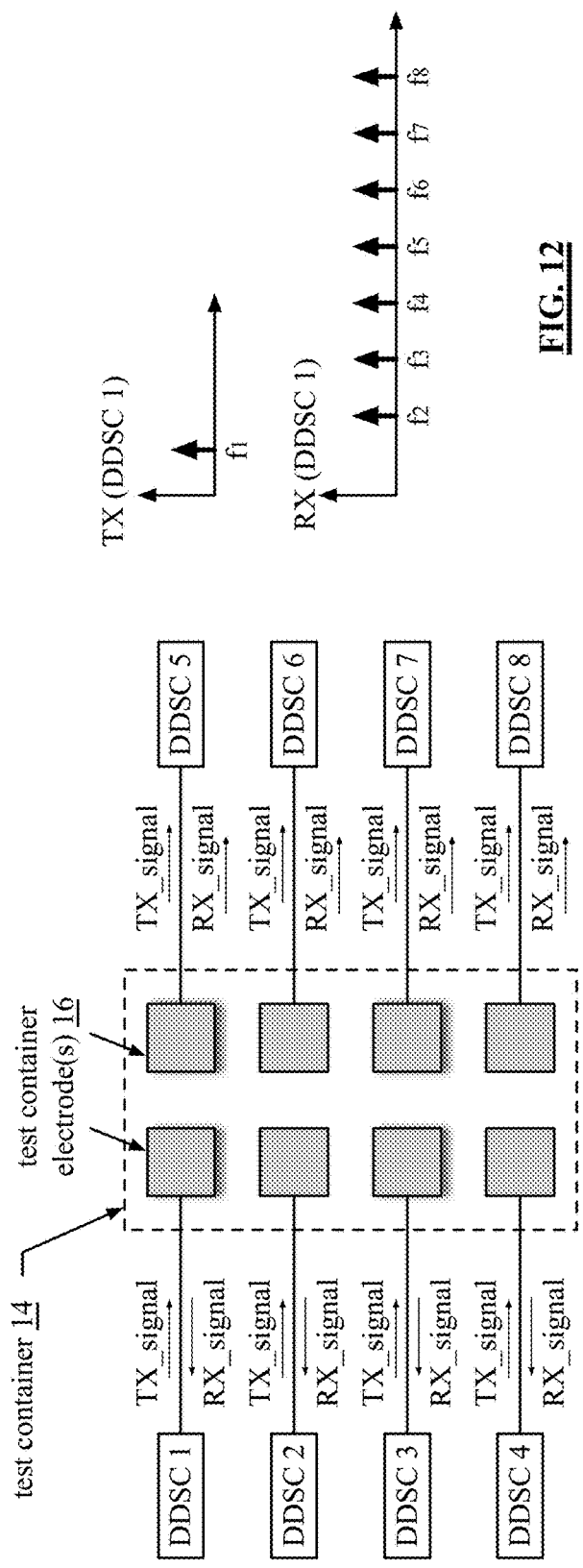
FIG. 11
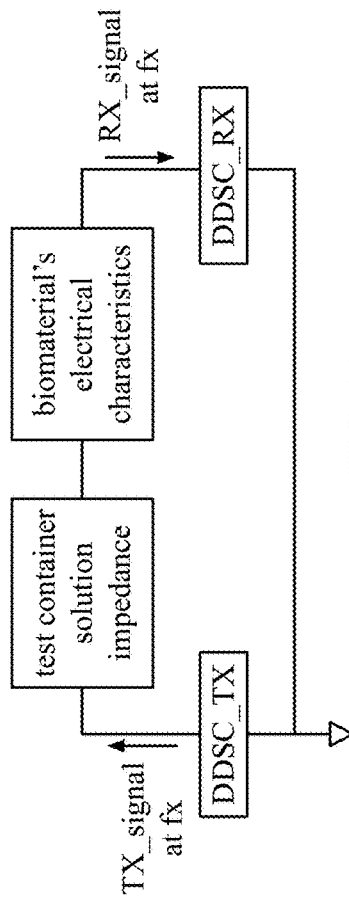
FIG. 12
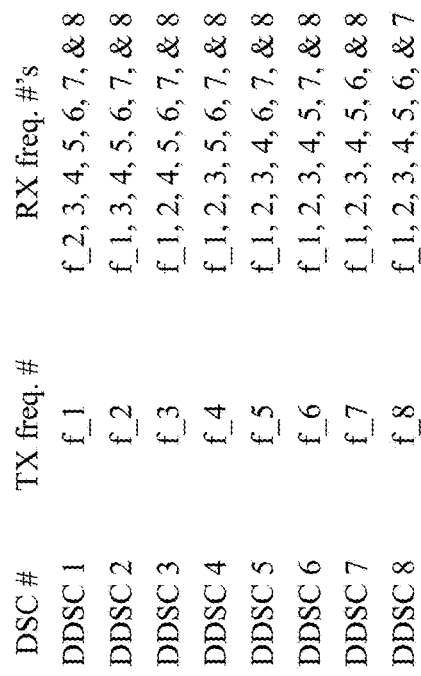
FIG. 14
| DSC # | TX freq. # | RX freq. #'s |
|---|---|---|
| DDSC 1 | f_1 | f_2, 3, 4, 5, 6, 7, & 8 |
| DDSC 2 | f_2 | f_1, 3, 4, 5, 6, 7, & 8 |
| DDSC 3 | f_3 | f_1, 2, 4, 5, 6, 7, & 8 |
| DDSC 4 | f_4 | f_1, 2, 3, 5, 6, 7, & 8 |
| DDSC 5 | f_5 | f_1, 2, 3, 4, 6, 7, & 8 |
| DDSC 6 | f_6 | f_1, 2, 3, 4, 5, 7, & 8 |
| DDSC 7 | f_7 | f_1, 2, 3, 4, 5, 6, & 8 |
| DDSC 8 | f_8 | f_1, 2, 3, 4, 5, 6, & 7 |
FIG. 13

1st set of impedances of impedance map "receive only" DDSCs

5th set of impedances of impedance map "receive only" DDSCs

|                       |     |     |     |     |
|-----------------------|-----|-----|-----|-----|
| 1st set of impedances | 1-2 | 1-3 | (1-4) |   |
| 2nd set of impedances | 2-1 | 2-3 | 2-4 |   |
| 3rd set of impedances | 3-1 | 3-2 | 3-4 |   |
| 4th set of impedances | (4-1) | 4-2 | 4-3 |   |
| 5th set of impedances | 1D-1 | 1D-2 | 1D-3 | 1D-4 |
| 6th set of impedances | 2D-1 | 2D-2 | 2D-3 | 2D-4 |
| 7th set of impedances | 3D-1 | 3D-2 | 3D-3 | 3D-4 |
| 8th set of impedances | 4D-1 | 4D-2 | 4D-3 | 4D-4 |

FIG. 18 test container impedance map 118 (solution 20 only with a set of "receive only" DDSCs)

1st set of impedances of impedance map "transmit & receive" DDSCs

5th set of impedances of impedance map "transmit & receive" DDSCs

|                        | 1-2 | 1-3 | 1-4 | 1-5 | 1-6 | 1-7 | 1-8 |
|------------------------|-----|-----|-----|-----|-----|-----|-----|
| 1st set of impedances  |     |     |     |     |     | (1-7) | 1-8 |
| 2nd set of impedances  | 2-1 | 2-3 | 2-4 | 2-5 | 2-6 | 2-7 | 2-8 |
| 3rd set of impedances  | 3-1 | 3-2 | 3-4 | 3-5 | 3-6 | 3-7 | 3-8 |
| 4th set of impedances  | 4-1 | 4-2 | 4-3 | 4-5 | 4-6 | 4-7 | 4-8 |
| 5th set of impedances  | 5-1 | 5-2 | 5-3 | 5-4 | 5-6 | 5-7 | 5-8 |
| 6th set of impedances  | 6-1 | 6-2 | 6-3 | 6-4 | 6-5 | 6-7 | 6-8 |
| 7th set of impedances  | (7-1) | 7-2 | 7-3 | 7-4 | 7-5 | 7-6 | 7-8 |
| 8th set of impedances  | 8-1 | 8-2 | 8-3 | 8-4 | 8-5 | 8-6 | 8-7 |

FIG. 21 test container impedance map 119 (solution 20 only with set of "transmit and receive" DDSCs)

transfer function of test container 14 contents

H(s) =Vout/VREF

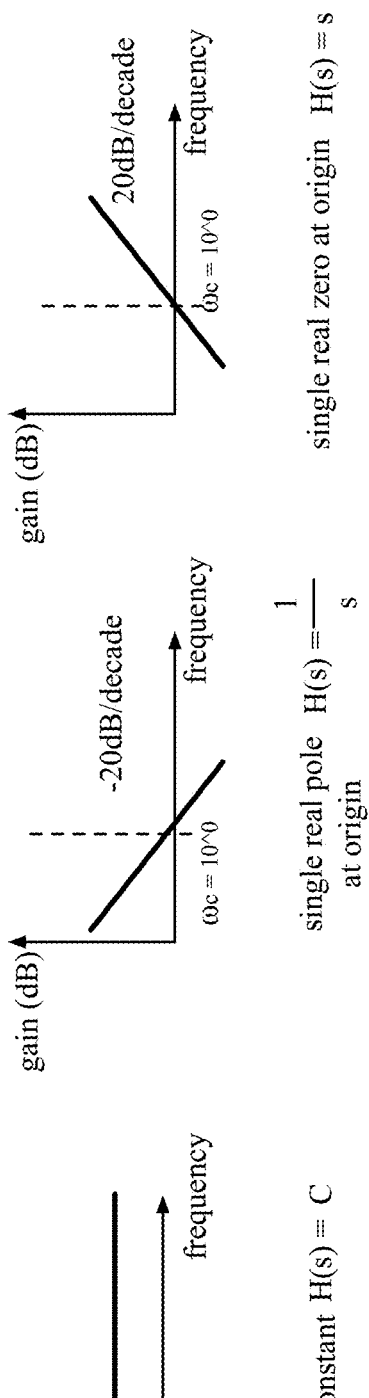
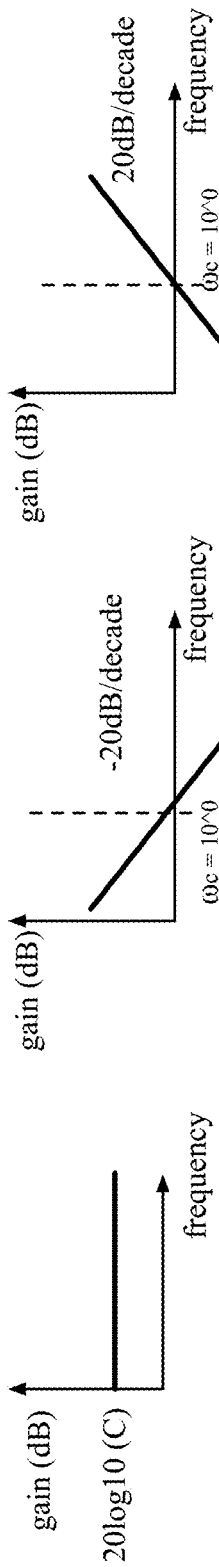
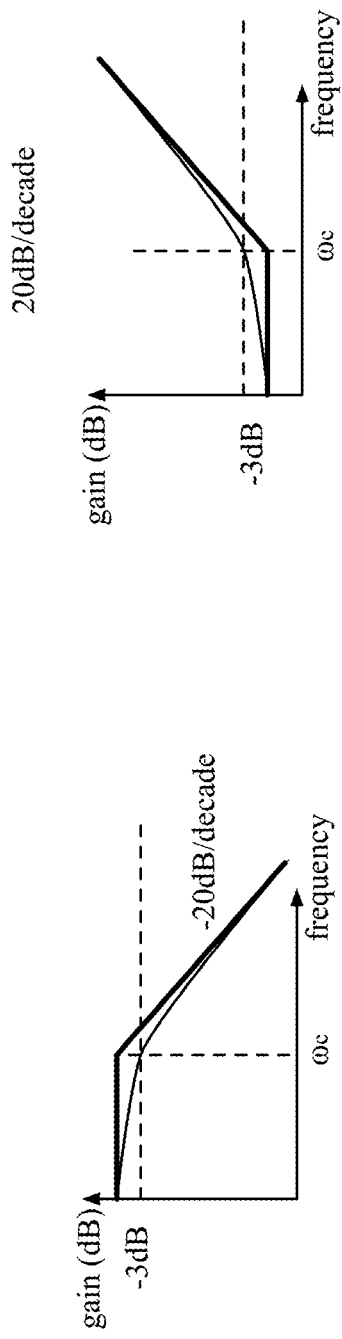
FIG. 29A constant $H(s) = C$
FIG. 29B single real pole at origin $H(s) = \frac{1}{s}$
FIG. 29C single real zero at origin $H(s) = s$
FIG. 29D single real pole (not at origin) $H(s) = \frac{1}{1 + s/\omega}$
FIG. 29E single real zero (not at origin) $H(s) = 1 + \frac{s}{\omega}$

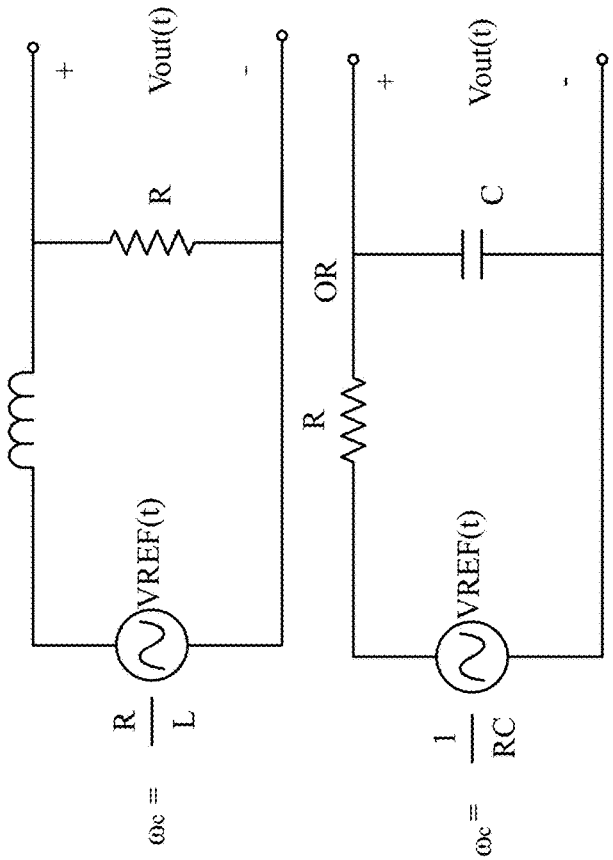
FIG. 31B
transfer function of solution and the mass
$$\omega c = \frac{R}{L}$$
$$\omega c = \frac{1}{RC}$$
FIG. 31C
electrical model of the mass
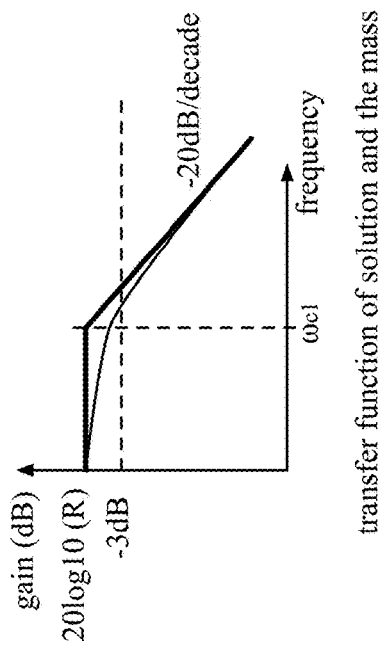
VREF @ f1    Vout @ f1
FIG. 31A transfer function of solution, mass, & testing substance electrical model of mass with testing substance 122b transfer function of solution, biological material, & testing substance electrical model of biological material with testing substance 122c reactive material test system 142
DDSC = differential drive-sense circuit

ORGANIC AND/OR INORGANIC MATERIAL TEST SYSTEM USING DIFFERENTIAL DRIVE-SENSE CIRCUITS

STATEMENT REGARDING FEDERALLY SPONSORED RESEARCH OR DEVELOPMENT

The present U.S. Utility patent application claims priority pursuant to 35 U.S.C. § 120 as a continuation-in-part of U.S. Utility application Ser. No. 16/730,118 entitled "ORGANIC & INORGANIC TEST SYSTEM", filed Dec. 30, 2019, which is hereby incorporated herein by reference in its entirety and made part of the present U.S. Utility patent application for all purposes.

INCORPORATION-BY-REFERENCE OF MATERIAL SUBMITTED ON A COMPACT DISC

Not Applicable.

BACKGROUND OF THE INVENTION

Technical Field of the Invention

This invention relates generally to data communication systems and more particularly to sensed data collection and/or communication.

Description of Related Art

Sensors are used in a wide variety of applications ranging from in-home automation, to industrial systems, to health care, to transportation, and so on. For example, sensors are placed in bodies, automobiles, airplanes, boats, ships, trucks, motorcycles, cell phones, televisions, touch-screens, industrial plants, appliances, motors, checkout counters, etc. for the variety of applications.

In general, a sensor converts a physical quantity into an electrical or optical signal. For example, a sensor converts a physical phenomenon, such as a biological condition, a chemical condition, an electric condition, an electromagnetic condition, a temperature, a magnetic condition, mechanical motion (position, velocity, acceleration, force, pressure), an optical condition, and/or a radioactivity condition, into an electrical signal.

A sensor includes a transducer, which functions to convert one form of energy (e.g., force) into another form of energy (e.g., electrical signal). There are a variety of transducers to support the various applications of sensors. For example, a transducer is capacitor, a piezoelectric transducer, a piezoresistive transducer, a thermal transducer, a thermal-couple, a photoconductive transducer such as a photoresistor, a photodiode, and/or phototransistor.

A sensor circuit is coupled to a sensor to provide the sensor with power and to receive the signal representing the physical phenomenon from the sensor. The sensor circuit includes at least three electrical connections to the sensor: one for a power supply; another for a common voltage reference (e.g., ground); and a third for receiving the signal representing the physical phenomenon. The signal representing the physical phenomenon will vary from the power supply voltage to ground as the physical phenomenon changes from one extreme to another (for the range of sensing the physical phenomenon).

The sensor circuits provide the received sensor signals to one or more computing devices for processing. A computing device is known to communicate data, process data, and/or store data. The computing device may be a cellular phone, a laptop, a tablet, a personal computer (PC), a work station, a video game device, a server, and/or a data center that support millions of web searches, stock trades, or on-line purchases every hour.

The computing device processes the sensor signals for a variety of applications. For example, the computing device processes sensor signals to determine temperatures of a variety of items in a refrigerated truck during transit. As another example, the computing device processes the sensor signals to determine a touch on a touch screen. As yet another example, the computing device processes the sensor signals to determine behavior of biological cells.

In vitro study of the behavior of cells is conventionally done using petri dishes, glass slides, or microplates (e.g., flat assay plates with multiple testing wells) as culture substrates and a form of optical analysis such as absorbance, fluorescence intensity, luminescence, time-resolved fluorescence, and/or fluorescence. Chemicals such as drugs and pesticides have different effects on cells such as destruction of cell membrane, prevention of protein synthesis, irreversible binding to receptors, enzymatic reactions, etc. Such effects can cause voltage changes, presence or absence of particular ions or molecules, etc. Dyes sensitive to those changes are applied to cells and different cellular effects are indicated through visual changes (e.g., a level of fluorescence). The dyes adversely affect the cells such that the cells usually die within a few hours. This substantially limit the usefulness of such testing techniques, especially when testing the cells' responses to a variety of stimuli.

BRIEF DESCRIPTION OF THE SEVERAL VIEWS OF THE DRAWING(S)

FIG. 5 is a schematic block diagram of an embodiment of a "receive only" differential drive-sense circuit (DDSC) in accordance with the present invention;

FIG. 6 is a schematic block diagram of an embodiment of a first set of test container electrodes coupled to a set of drive-sense circuits (DSCs) and a second set of test container electrodes coupled to a set of "receive only" differential drive-sense circuits (DDSCs) in accordance with the present invention;

FIG. 7 is a diagram of an example of a transmit signal of a drive-sense circuit (DSC) and receive signals of the DSC and a "receive only" differential drive-sense circuits (DDSCs), in the frequency domain, of the embodiment of FIG. 6 in accordance with the present invention;

FIG. 8 is a diagram of an example of a frequency pattern used by the drive-sense circuits (DSCs) of the embodiment of FIG. 6 in accordance with the present invention;

FIG. 9 is a schematic diagram of an example of a generic circuit of a transmit drive-sense circuit (DSC) and a "receive only" differential drive-sense circuit (DDSC) of the embodiment of FIG. 6 in accordance with the present invention;

FIG. 11 is a schematic block diagram of an embodiment of a set of test container electrodes coupled to a set of "transmit and receive" differential drive-sense circuits (DDSCs) in accordance with the present invention;

FIG. 12 is a diagram of an example of a transmit signal and a receive signal of a "transmit and receive" differential drive-sense circuit (DDSC), in the frequency domain, of the embodiment of FIG. 11 in accordance with the present invention;

FIG. 13 is a diagram of an example of a frequency pattern used by the "transmit and receive" differential drive-sense circuits (DDSCs) of the embodiment of FIG. 11 in accordance with the present invention;

FIG. 14 is a schematic diagram of an example of a generic circuit of a transmit differential drive-sense circuit (DDSC) and a receive differential drive-sense circuit (DDSC) of the embodiment of FIG. 11 in accordance with the present invention;

FIG. 18 is a schematic block diagram of a test container impedance map in accordance with the present invention;

FIG. 21 is a schematic block diagram of a test container impedance map in accordance with the present invention;

FIGS. 29A-29G are schematic block diagrams of examples of transfer functions produced by a frequency sweep of an input signal of a differential drive-sense circuit (DDSC) of a test container in accordance with the present invention;

FIGS. 31A-31C are schematic block diagrams of an embodiment of determining a transfer function of a test container containing a solution and an organic and/or inorganic mass in accordance with the present invention;

DETAILED DESCRIPTION OF THE INVENTION

Figure 1:
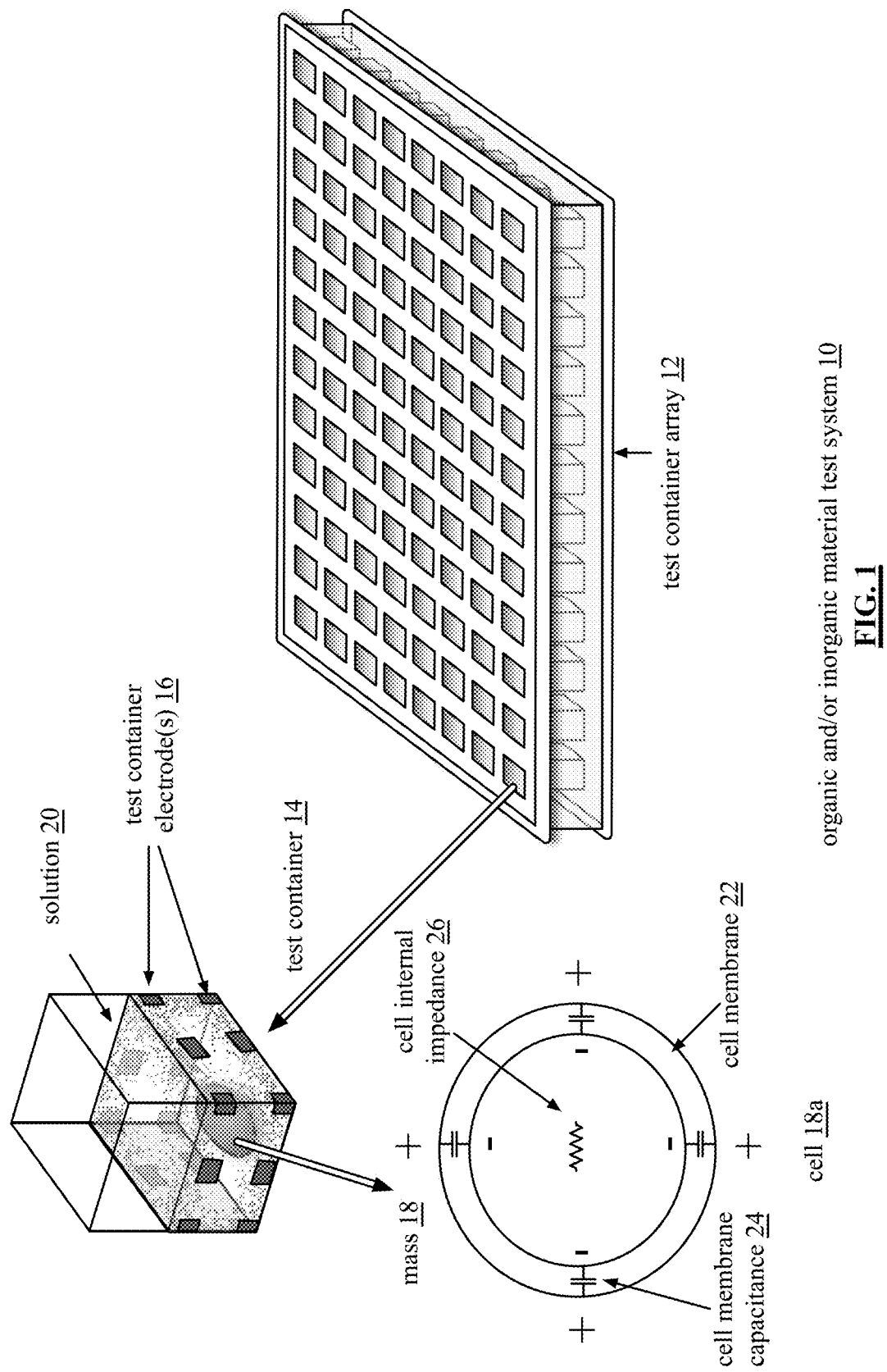
FIG. 1 is a schematic block diagram of an embodiment of an organic and/or inorganic material test system in accordance with the present invention.

FIG. 1 is a schematic block diagram of an embodiment of an organic and/or inorganic material test system 10 ("test system") that includes a test container array 12 including a plurality of test containers 14. The test container array 12 may be comprised of a variety of materials such as polystyrene, polypropylene, glass, flexible plastic tape, and quartz, and may be a variety of shapes and sizes. The test container array 12 is shown as a rectangular array of 8×12 cubical test containers 14. The test container array may include more or less test containers 14 than shown. For example, the test system includes at least one test container 14. The test containers 14 may be a variety of shapes, depths, and sizes (e.g., cylindrical, rectangular prism, circular, test tube, petri dish, etc.). Each test container 14 includes a plurality of test container electrodes 16 (e.g., two or more test container electrodes 16).

The test container electrodes 16 are electric conductors used to monitor electrical characteristics of contents within the test container 14. The test container electrodes 16 are constructed of electrically conductive material (e.g., a conductive metal such as copper, silver, gold, tin, or a non-metallic conductor such as graphite, conductive polymer, etc.). The test container electrodes 16 may be a transparent conductive material, such that optical observations of the testing container 14 are unobstructed. For instance, an electrode is constructed from one or more of: Indium Tin Oxide, Graphene, Carbon Nanotubes, Thin Metal Films, Silver Nanowires Hybrid Materials, Aluminum-doped Zinc Oxide (AZO), Amorphous Indium-Zinc Oxide, Gallium-doped Zinc Oxide (GZO), and poly polystyrene sulfonate (PEDOT). The test container electrodes 16 may be a variety of shapes (e.g., coil, cylindrical, conical, flat, square, circular, domed, spherical, spear shaped, etc.) and may be placed in a variety of positions within the test container 14. For example, eight test container electrodes 16 are shown near the bottom of the test container 14 and eight test container electrodes 16 are below a solution 20 fill line of the test container 14.

The test system 10 is operable to detect and interpret electrical characteristics of an organic and/or inorganic material ("mass" 18) present in a test container 14 of the test container array 12. An organic mass (or material) includes living organisms or portions thereof that always include carbon and may or may not contain hydrogen. As used herein, the terms organic material and organic mass are intended to generally encompass materials from living organisms. For example, the organic mass includes one or more cells (e.g., an individual cell 18, multiple cells, tissue, etc.) and/or one or more portions of a cell (e.g., a section of cell membrane). A cell may be from an animal, human, plant, and/or other biological cell and is any type of cell (e.g., heart, brain, neuron, muscle, skin, lung, etc.). Inorganic masses/materials involve all other parts of the periodic table such as non-living organisms that produce an electrical characteristic (e.g., voltage, current, impedance, resistance, reactance, etc.) with or without a stimulus. As used herein, the terms inorganic material and inorganic mass are intended to generally encompass materials from non-living organisms. For example, some inorganic masses/materials include chemical catalysts, medicines, fuels, etc.

As an example of a mass 18, a cell 18a is shown. The cell 18a is a complex structural entity consisting of many organelles that can be electrically characterized as an impedance. Animal cells are surrounded by a cell membrane 22 composed of a lipid bilayer with proteins embedded in it. The cell membrane 22 acts as both an insulator and a diffusion barrier to the movement of ions. Internal and external ion concentrations of the cell 18a are different resulting in a cell membrane capacitance 24. The cell 18a has an internal impedance 26 (resistance and/or reactance) and a cell membrane impedance that arises from the fact that the cell membrane 22 impedes the movement of charges across it. Depending on the nature of testing, the inductance of a cell may or may not be negligible. The cell membrane capacitance 24 is relatively unaffected by molecules embedded in it and has a value estimated at about 0.9-2 pF/cm$^2$ (i.e., 90-200 pF/μm$^2$) where the total capacitance of the membrane is proportional to its area. There are hundreds of different types of biological cells ranging in size from about 5 μm-150 μm in diameter with cell membrane thicknesses ranging from 7.5 nm to 10 nm.

A cell 18a can also be electrically characterized by cell membrane 22 potential. Cell membrane 22 potential or cell membrane 22 voltage is the difference in electric potential between the interior and exterior of the cell 18. Typical values of cell membrane 22 potential from the exterior of the cell are measured in ranges from a few nano-volts to milli-volts. In electrically excitable cells such as neurons and muscle cells, membrane potential changes occur when signals are transmitted within the cell. Signals are transmitted by the opening and closing of ion channels in the cell membrane 22 which can make the interior voltage of the cell more negative (hyperpolarization) or less negative (depolarization). For non-excitable cells, membrane potential is held at a relatively stable value called resting potential.

In FIG. 1, a mass 18 (e.g., one or more cells 18a) is shown in a solution 20 in the testing container 14. The solution 20 maintains the integrity and viability of the mass 18 and negligibly interferes with testing substances and/or biochemical reactions. For example, the solution 20 is a saline solution, a preservative, a cell culture solution, etc., that is electrically conductive. The test system 10 is operable to detect and interpret the electrical characteristics of the contents (e.g., a solution, an organic mass, an inorganic mass, a testing substance, etc.) present in the testing container 14. For example, the test system 10 is operable to detect and interpret the electrical characteristics of the solution 20, the electrical characteristics of the mass 18 in the solution 20, and the electrical characteristics of the mass 18 in the solution 20 when a testing substance is added.

Based on the differences between the detected electrical characteristics of the mass 18 (e.g., with and without the testing substance), the test system 10 can determine the effect of a testing substance on the mass. The electrical characteristics of the mass 18 include one or more of: impedance, membrane potential, size, shape, density, movement, orientation, cell excitation (e.g., beat amplitude), etc. For example, in a cell becoming non-viable, the cell membrane 22 is unable to maintain its potential resulting in a decreased capacitance (e.g., as a cell dies, its impedance drops). The test system 10 is able to detect this change in impedance and interpret the effect as cell death.

As another example, the size and shape of a cell responds to chemical, biological, and/or physical stimuli. Based on which test container electrodes 16 experience changes in electrical characteristics and at what level, the size, shape, and movement of a cell can be mapped. The test system 10 is able to detect changes in cell size, shape, and position (e.g., migration) in response to a testing substance and interpret the effect as a cell condition (e.g., a shrinking cell may indicate cell destruction, etc.).

As another example, a testing substance can impact the ion concentration of a cell 18$a$ and thus affect the cell membrane 22 voltage. The test system 10 is able to detect this change in cell membrane 22 voltage and interpret the effect as the change in ion concentration caused by the testing substance. A more detailed discussion of data processing of the test system 10 is discussed with reference to one or more of the following Figures.

Figure 2:
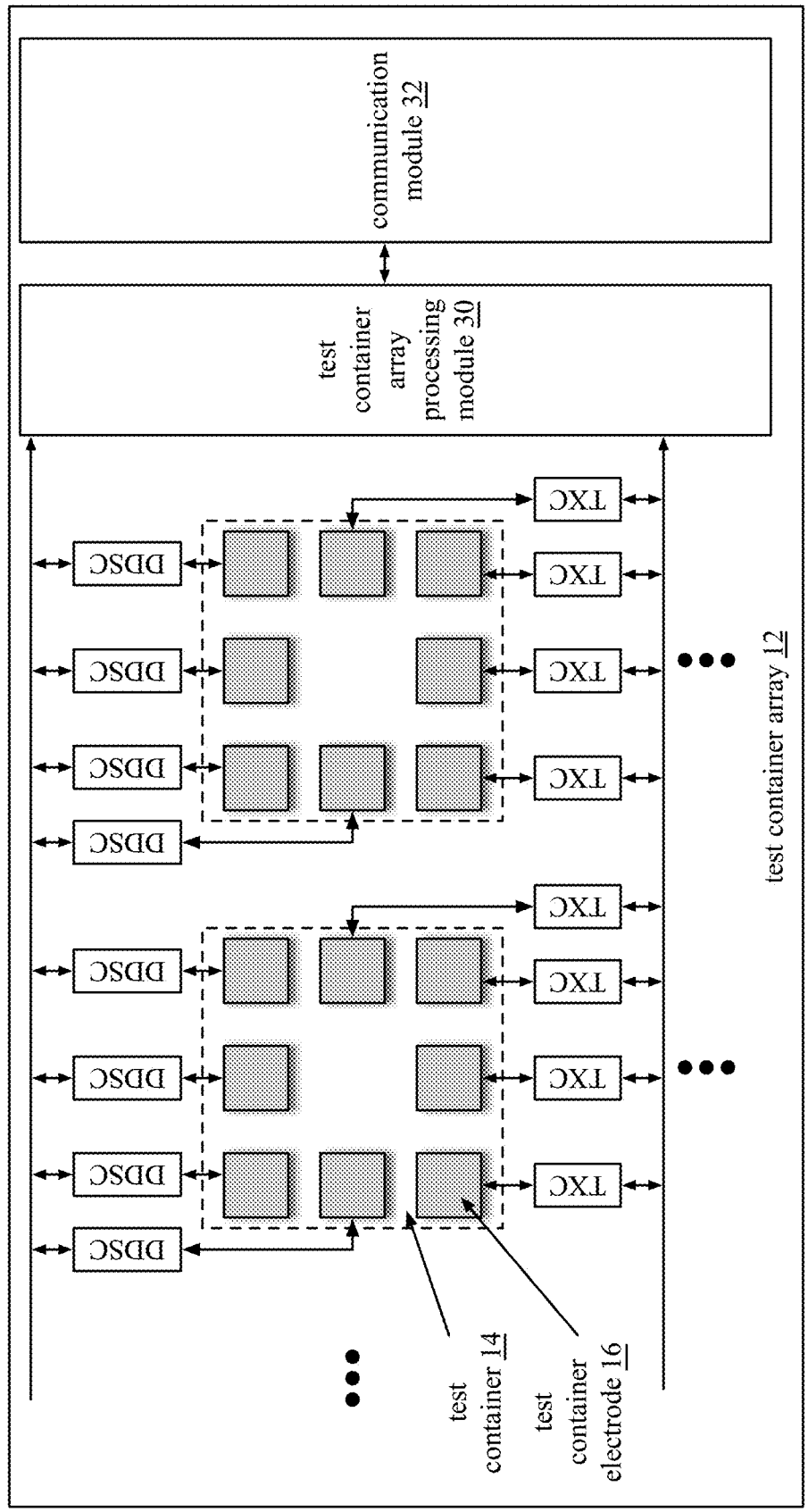
FIG. 2 is a schematic block diagram of an embodiment of an organic and/or inorganic material test system in accordance with the present invention.

FIG. 2 is a schematic block diagram of an embodiment of a test system 10 that includes a test container array 12 including at least one test container 14, a plurality of test container electrodes 16 (e.g., at least two test container electrodes per test container), a plurality of transmit (TX) circuits (TXCs), a plurality of differential drive-sense circuits (DDSCs), a test container array processing module 30, and a communication module 32.

One or more of the test container array processing module 30 and the communication module 32 are integrated into the test container array 12 or within separate devices. The communication module 32 includes a wireless communication unit and/or a wired communication unit. A wireless communication unit includes a wireless local area network (WLAN) communication device, a cellular communication device, a Bluetooth device, and/or a ZigBee communication device. A wired communication unit includes a Gigabit LAN connection, a Firewire connection, and/or a proprietary computer wired connection. Regardless of the specific implementation of the communication module 32, it is constructed in accordance with one or more wired communication protocol and/or one or more wireless communication protocols that is/are in accordance with the one or more of the Open System Interconnection (OSI) model, the Transmission Control Protocol/Internet Protocol (TCP/IP) model, and other communication protocol module.

Each test container 14 includes at least two test container electrodes 16. For example, eight test container electrodes 16 are included in each test container 14. Four test container electrodes 16 of the eight test container electrodes 16 may be near the bottom of the test container 14 and four test container electrodes 16 of the eight test container electrodes 16 may be near a fill line of the test container 14.

A first set of test container electrodes 16 of the test container electrodes 16 are coupled to a set of transmit (TX) circuits (TXCs). A second set of test container electrodes 16 of the test container electrodes 16 are coupled to a set of differential drive-sense circuits (DDSCs). The first set of test container electrodes 16 is located in an opposite location to the second set of test container electrodes 16. For example, the first set of test container electrodes 16 includes four test container electrodes 16 in this example and is located on one side of the test container 14. The second set of test container electrodes 16 includes the other four test container electrodes 16 and is located on the other side of the test container 14.

A TXC may include a drive-sense circuit (DSC) or a differential drive-sense circuit (DDSC) that are operable to transmit a signal through contents of the test container 14. A DSC functions as described in co-pending patent application entitled, "DRIVE SENSE CIRCUIT WITH DRIVE-SENSE LINE", having a serial number of Ser. No. 16/113,379, and a filing date of Aug. 27, 2018.

The TXCs coupled to the first set of test container electrodes 16 provide transmit signals to the second set of test container electrodes 16 and detect changes in electrical characteristics of the test container electrodes 16 without the use of electric field enhancers. As such, materials such as cell(s) are not damaged during testing, since an electric field enhancer is not used, and the changes to the electrical characteristics of the materials are directly attributable to the stimulus added to the solution (e.g., various medications, various environmental elements, pollutants, viruses, bacteria, etc.). This provides a significant benefit for individualized medicine where a patient's cells can be tested for a variety of conditions and responses. And not just an immediate reaction, but over time since the testing itself does not kill the cells.

The DDSCs coupled to the second set of test container electrodes 16 are operable to detect very small changes in electrical characteristics of the test container electrodes 16 without the use of electric field enhancers. The DDSCs will be described in greater detail with reference to FIGS. 5 and 10.

The DDSCs and TXCs provide the detected changes in electrical characteristics of the test container electrodes 16 (i.e., sensed signals, analog receive signals, etc.) to the test container array processing module 30. In another embodiment, a processing module is coupled to each test container (e.g., a test container processing module). The test container array processing module 30 (i.e., the processing module) is described in greater detail at the end of the detailed description of the invention section. The test container array processing module 30 processes the detected changes in electrical characteristics of the test container electrodes 16 from the DDSCs and the TXCs to determine the electrical characteristics of contents of the test system 10. For example, the test container array processing module 30 filters the data (e.g., via one or more bandpass filters) received from the DDSCs and TXCs and interprets the filtered data to determine impedance values representative of the electrical characteristics of contents of the test container 14. As another example, the test container array processing module 30 performs a frequency sweep on the signals generated by the DDSCs to produce a transfer function representative of the contents of the test container 14. The test container array processing module 30 is operable to analyze the transfer function to determine characteristics of the contents of the test container 14. A more detailed discussion of data processing of the test system 10 is discussed with reference to one or more of the following Figures.

The test container array processing module 30 communicates the electrical characteristics of test container contents to the communication module 32. Communicating the electrical characteristics of test container contents to the communication module 32 may include formatting the data in a particular format with respect to the communication protocol of the communication module. The communication module 32 is operable to communicate the electrical characteristics of test container contents via one or more communication protocols.

In another embodiment, the test system 10 does not include a processing module and communicates signals via the communication module 32 to an external computing device and/or processing module for analysis.

Figure 3:
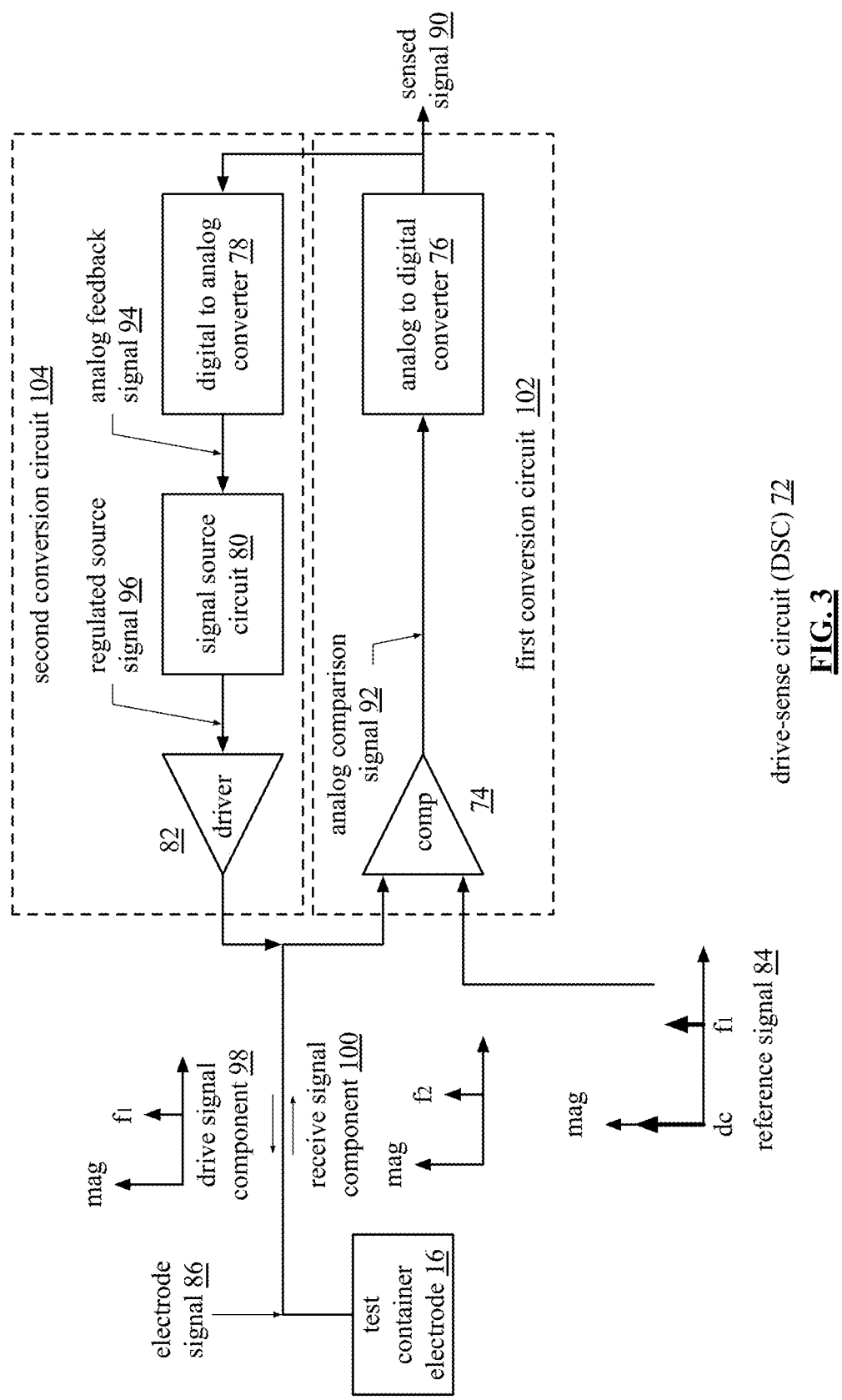
FIG. 3 is a schematic block diagram of an embodiment of a drive-sense circuit (DSC) in accordance with the present invention.

FIG. 3 is a schematic block diagram an embodiment of a drive-sense circuit (DSC) 72 that includes a first conversion circuit 102 and a second conversion circuit 104. The first conversion circuit 102 includes comparator (comp) 74 and an analog to digital converter (ADC) 76. The second conversion circuit 104 includes a digital to analog converter (DAC) 78, a signal source circuit 80, and a driver 82. The analog to digital converter (ADC) 76 may be implemented in a variety of ways. For example, the (ADC) 76 is one of: a flash ADC, a successive approximation ADC, a ramp-compare ADC, a Wilkinson ADC, an integrating ADC, a delta encoded ADC, and/or a sigma-delta ADC. The digital to analog converter (DAC) 214 may be a sigma-delta DAC, a pulse width modulator DAC, a binary weighted DAC, a successive approximation DAC, and/or a thermometer-coded DAC.

The feedback loop of the drive sense circuit 72 functions to keep the electrode signal 86 substantially matching the analog reference signal 84. As such, the electrode signal 86 will have a similar waveform to that of the analog reference signal 84. The electrode signal 86 includes a drive signal component 98 and a receive signal component 100. The drive signal component 98 corresponds to the transmit signal at f1 produced by the DSC and the receive signal component 100 corresponds to a received transmit signal at f2 produced by another DSC.

The first conversion circuit 102 converts the electrode signal 86 into a sensed signal 90. The second conversion circuit 104 generates the drive signal component 98 from the sensed signal 90. As an example, the first and second conversion circuits 102 and 104 function to keep the electrode signal 86 substantially constant (e.g., substantially matching the reference signal 84) with the first conversion circuit creating the sensed signal 90 to correspond the receive signal component 100 of the electrode signal 86 and the second conversion circuit 104 generating the drive signal component 98 based on adjusting the source signal in accordance with the sensed signal 90.

In an example, the electrode signal 86 is provided to a test container electrode 16 as a regulated current signal. The regulated current (I) signal in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. To regulate the current signal, the DSC adjusts the drive signal component 98 based on the receive signal component 100 of the sensed signal 90, which is indicative of the impedance of the test container contents and changes thereof.

More specifically, the comparator 74 compares the electrode signal 86 to the analog reference signal 84 having the oscillating component frequency f1 to produce an analog comparison signal 92. The analog comparison signal 92 contains a representation of the receive signal having the oscillating component frequency f2. The analog reference signal 84 (e.g., a current signal or a voltage signal) includes a DC component and an oscillating component at a first frequency f1. The DC component is a DC voltage in the range of a few tens of milli-volts to tens of volts or more. The oscillating component includes a sinusoidal signal, a square wave signal, a triangular wave signal, a multiple level signal (e.g., has varying magnitude over time with respect to the DC component), and/or a polygonal signal (e.g., has a symmetrical or asymmetrical polygonal shape with respect to the DC component). In another example, the frequency of the oscillating component may vary so that it can be tuned to the impedance of the electrode and/or to be off-set in frequency from other electrode signals.

In an embodiment, a processing module (e.g., one or more of a test container processing module, a test container array processing module, or external processing module) provides analog reference signals to the drive-sense circuits. For example, each drive-sense circuit receives a unique analog reference signal. As another example, a first group of drive-sense circuits receive a first analog reference signal and a second group of drive-sense circuits receive a second analog reference signal. In yet another example, the drive-sense circuits receive the same analog reference signal. Note that the processing module uses a combination of analog reference signals with control signals to ensure that different frequencies are used for oscillating components of the analog reference signal.

The analog to digital converter 76 converts the analog comparison signal 84 into a digital sensed signal 90 representative of the received signal. In another embodiment, the analog to digital converter 76 and the digital to analog converter 78 are not included and the analog comparison signal 84 is output to the processing module for analysis and analog filtering.

The second conversion circuit 104 adjusts the regulated current based on the changes to the sensed signal 90. More specifically, the digital to analog converter (DAC) 78 converts the sensed signal 90 into an analog feedback signal 94. The signal source circuit 80 (e.g., a dependent current source, a linear regulator, a DC-DC power supply, etc.) generates a regulated source signal 96 (e.g., a regulated current signal or a regulated voltage signal) based on the analog feedback signal 94. The driver 82 increases power of the regulated source signal 94 to produce the drive signal component 86. Note that, in an embodiment, the driver may be omitted.

As another example, the electrode signal 86 is provided to the test container electrode 16 as a regulated voltage signal. The regulated voltage (V) signal in combination with the impedance (Z) of the test container contents creates an electrode current (I), where I=V/Z. As the impedance (Z) of electrode changes, the regulated voltage (V) signal is adjusted to keep the electrode current (I) substantially unchanged. To regulate the voltage signal, the first conversion circuit 102 adjusts the sensed signal 90 based on the receive signal component 100, which is indicative of the impedance of the test container contents and changes thereof. The second conversion circuit 104 adjusts the regulated voltage based on the changes to the sensed signal 90.

When testing a cell, multiplexing of a DSC to a test container 14 is possible since the sampling rate of a cell(s) is very low (e.g., in the range of 100 Hz to 0.1 Hz). For example, a cell's electrical characteristics are sampled once per second. Further, at this sampling rate, the digital filtering of the DSC outputted signals can have a very narrow bandwidth (e.g., 100 Hz or less). The combination of low sampling rate, greater than 100 dBm SNR of the DSCs, and very narrow bandwidth allows for very accurate measurements of very low voltage (and/or current) changes of the cells (e.g., of a few nano-volts to tens of pico-volts) in this embodiment and in others. As discussed with reference to FIG. 2, the transmit circuits (TXCs) may be DSCs.

Figure 4:
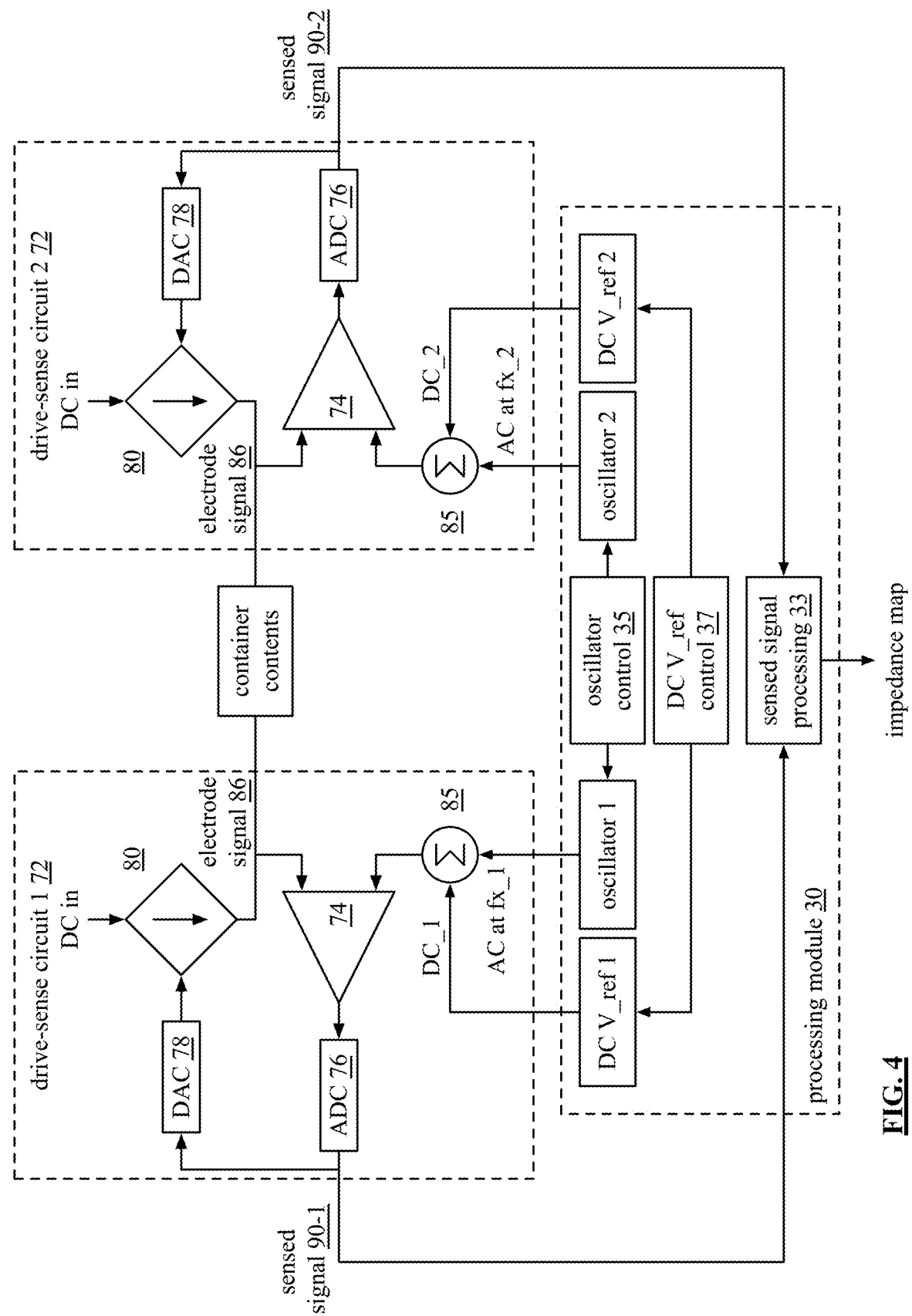
FIG. 4 is a schematic block diagram of an example of drive-sense circuits (DSCs) sensing contents of a test container in accordance with the present invention.

FIG. 4 is a schematic block diagram an example of drive-sense circuits (DSCs 1-2) 72 sensing contents of a test container 14. Each DSC includes a comparator 74, an analog to digital converter (ADC) 76, a digital to analog converter (DAC) 78, a regulated current source circuit 80, and an adder 85. The processing module 30 (e.g., the test container array processing module) includes a sensed signal processing unit 33, a DC V_ref control unit 37, and an oscillator control unit 35.

The DC V_ref control 37 generates DC voltage components (e.g., DC_1 and DC_2) of analog reference signals to provide to the DSCs. The DC V_ref control 37 generates DC V_ref 1 at a voltage of DC_1 to provide to DSC 1 and a DC V_ref 2 at a voltage of DC_2 to provide to DSC 2. DC_1 and DC_2 are voltages in the range of a few tens of milli-volts to tens of volts or more. The DC V_ref control 37 generates DC_1 and DC_2 to be different such that a voltage potential exists between the DSCs 1-2 72.

The oscillator control 35 generates the AC oscillating components of analog reference signals provided to the DSCs. The oscillator control 35 generates an oscillator 1 at frequency fx_1 to provide to DSC 1 and an oscillator 2 at a frequency fx-2 to provide to DSC 2. The oscillating components include a sinusoidal signal, a square wave signal, a triangular wave signal, a multiple level signal (e.g., has varying magnitude over time with respect to the DC component), and/or a polygonal signal (e.g., has a symmetrical or asymmetrical polygonal shape with respect to the DC component).

The adders 85 of the DSCs 1-2 72 combine the DC components with the oscillating components to produce analog reference signals for input to the comparators 74. The DSCs function to keep the electrode signal 86 substantially constant (e.g., substantially matching the reference signal).

For example, an electrode signal 86 is provided to a test container electrode as a regulated current signal. The regulated current (I) signal in combination with the impedance (Z) of the contents of test container (e.g., solution and/or biological material) creates a voltage (V), where V=I*Z. As the impedance (Z) of test container contents changes, the regulated current (I) signal is adjusted to keep the voltage (V) substantially unchanged. To regulate the current signal, each DSC 1-2 72 adjusts the sensed signals 90-1 and 90-2 based on the receive signal component of the electrode signal 86, which is indicative of the impedance of the test container contents and changes thereof.

The DSCs 72 provide the sensed signals 90-1 and 90-2 to the sensed signal processing unit 33 of the processing module 30. The processing module 30 generates an impedance map of the test container based on the sensed signals.

FIG. 5 is a schematic block diagram of a "receive only" differential drive sense circuit (DDSC) 40 that includes drive-sense circuits 72-1 and 72-2, a 180° phase shifter 58, and an output operational amplifier (op-amp) 54. The drive-sense circuits 72-1 and 72-2 each include an op-amp 56-1 and 56-2, and a regulated current source circuit 42-1 and 42-2. Within the drive-sense circuit 72-1, the positive input terminal of the op-amp 56-1 is coupled to a test container electrode 16 and the negative input terminal of the op-amp 56-1 is coupled to a voltage reference source (e.g., via a signal generator, via the processing module that generates and provides the voltage reference signal, etc.) that provides a voltage reference signal VREF. Within the drive-sense circuit 72-2, the positive input terminal of the op-amp 56-2 is coupled to the 180° degree phase shifter 58 which provides a 180° phase shifted version of voltage reference signal VREF (voltage reference signal VREF') and the negative input terminal of the op-amp 56-2 is coupled to the test container electrode 16.

The drive-sense circuits 72-1 and 72-2 operate similarly to the drive sense circuit 72 of FIGS. 3-4 where the feedback loops function to keep the electrode signals 44-1 and 44-2 substantially matching the analog voltage reference signal (VREF and VREF'). As such, the electrode signal 44-1 will have a similar waveform to that of the VREF and the electrode signal 44-2 will have a similar waveform to that of the VREF'. The drive components of the electrode signals (VREF and VREF') cancel each other out due to the 180° phase shift such that the differential drive-sense circuit 40 does not transmit a signal via the test container electrode 16 making it "receive only."

The electrode signals 44-1 and 44-2 include a drive signal component (that is canceled out) and a receive signal component. The drive signal component corresponds to the transmit signal at f1 produced by the DSCs and the receive signal component corresponds to a received transmit signal at f2 produced by a transmit circuit (e.g., a DSC) located at a different position in the test container.

The op-amp 56-1 of the drive-sense circuit 72-1 compares the electrode signal 44-1 to the VREF signal having the oscillating component frequency f1 to produce an analog comparison signal 50-1. The analog comparison signal 50-1 contains a representation of the receive signal having the oscillating component frequency f2 (e.g., the analog comparison signal 50-1 contains a representation of the VREF signal and the receive signal). The analog comparison signal 50-1 is fed back to the regulated current source circuit 42-1 as analog feedback signal 52-1. The regulated current source circuit 42-1 generates a regulated source signal 46-1 (e.g., a regulated current signal (I1)) based on the analog feedback signal 52-1. The regulated current signal (I1) in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. For example, if the impedance increases the voltage on the electrode, the regulated current signal (I1) provides more current to keep the voltage substantially equal to VREF.

The op-amp 56-2 of the drive-sense circuit 72-2 compares the electrode signal 44-2 to the VREF' signal (the 180° phase shifted VREF signal) having the oscillating component frequency f1 to produce an analog comparison signal 50-2. The analog comparison signal 50-2 contains a representation of the receive signal having the oscillating component frequency f2 (e.g., the analog comparison signal 50-2 contains a representation of the VREF' signal and the receive signal). The analog comparison signal 50-2 is fed back to the regulated current source circuit 42-2 as analog feedback signal 52-2. The regulated current source circuit 42-2 generates a regulated source signal 46-2 (e.g., a regulated current signal (I2)) based on the analog feedback signal 52-2. The regulated current signal (I2) in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. For example, if the impedance lowers the voltage on the electrode, the regulated current signal (I2) is increased to keep the voltage substantially equal to VREF'.

The output op-amp 54 compares the analog comparison signal 50-1 and the analog comparison signal 50-2 to produce an analog receive (RX) signal 52. Comparing the analog comparison signal 50-1 and the analog comparison signal 50-2 cancels out the VREF and VREF' components due to the phase and doubles the receive component. As such, the differential drive-sense circuit 40 is more sensitive than the drive-sense circuit 72 at sensing very low signals since the sensed receive signal is doubled in comparison to the drive-sense circuit 72. Further, with the differential drive-sense circuit 40, because the VREF and VREF' components are canceled out, common mode noise is canceled out. Therefore, the differential drive-sense circuit 40 is more sensitive and has better signal to noise ratio than the drive-sense circuit 72.

In another embodiment, the "receive only" DDSC 40 includes an analog to digital converter (ADC) operable to convert the analog RX signal 52 to a digital sensed signal for input to a processing module.

Figure 5A:
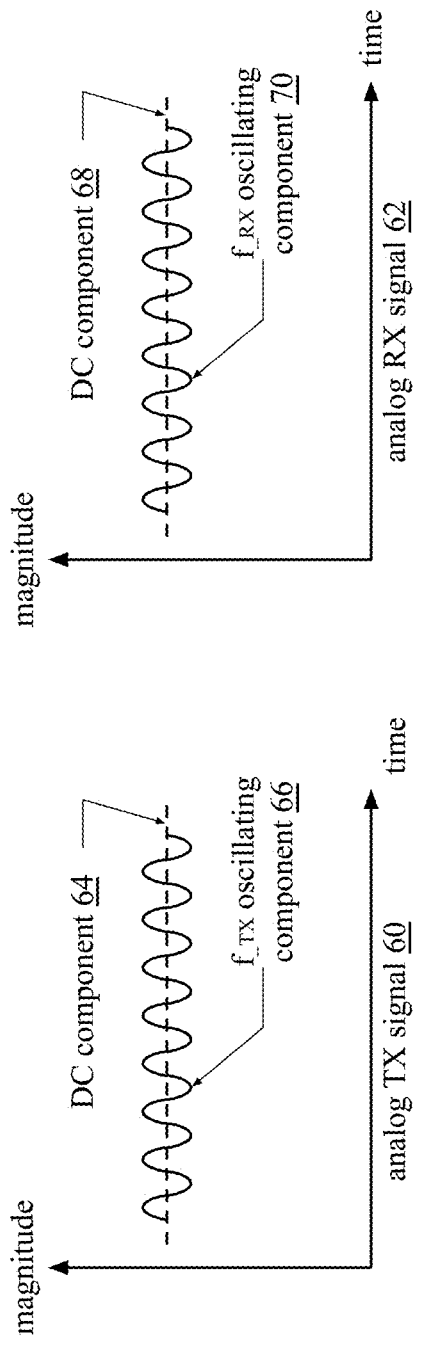
FIGS. 5A-5B are schematic block diagrams of examples of drive-sense circuit (DSC) and "receive only" differential drive-sense circuit (DDSC) signals in accordance with the present invention.
Figure 5B:
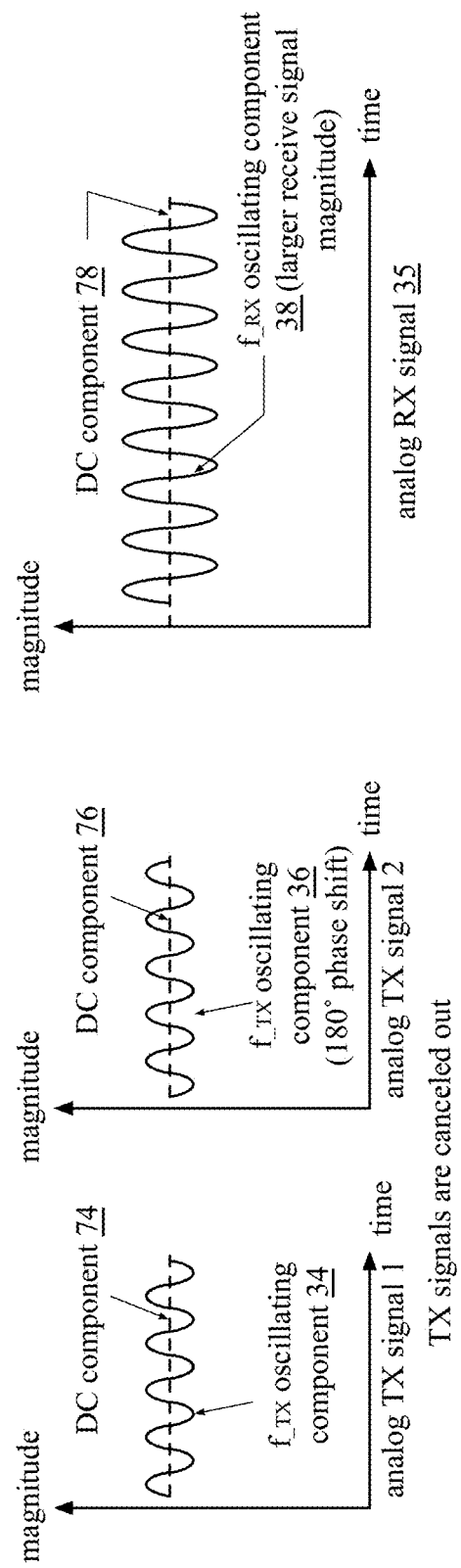

FIGS. 5A-5B are schematic block diagrams of examples of signals of the drive-sense circuit and the "receive only" differential drive-sense circuit of FIGS. 3 and 5. In FIG. 5A, an analog transmit (TX) signal 60 and an analog receive (RX) signal 62 (e.g., the analog comparison signal) of a drive-sense circuit are shown. The analog transmit signal 60 includes a DC component 64 and an oscillating component 66 at a frequency $f_{\_TX}$. The analog transmit signal 60 is regulated by the drive-sense circuit to be substantially equal to a voltage reference signal having the DC component 64 and an oscillating component 66. The analog receive signal 62 includes a DC component 68 and an oscillating component 70 at a frequency $f_{\_RX}$. The analog receive signal 62 is an analog transmit signal transmitted by another transmit circuit of the test container and is representative of changes in electrical characteristics in the contents of the test container.

In FIG. 5B, an analog transmit (TX) signal 1, an analog transmit (TX) signal 2, and an analog receive (RX) signal 35 of a "receive only" differential drive-sense circuit are shown. The analog transmit signal 1 includes a DC component 74 and an oscillating component 34 at a frequency $f_{\_TX}$. The analog transmit signal 1 is regulated by a first drive-sense circuit of the "receive only" differential drive-sense circuit to be substantially equal to a voltage reference signal (VREF) having the DC component 74 and an oscillating component 34.

The analog transmit signal 2 includes a DC component 76 and an oscillating component 36 at a frequency $f_{\_TX}$ and a 180° phase shift to the oscillating component 36. The analog transmit signal 2 is regulated by a second drive sense circuit of the differential drive sense circuit to be substantially equal to a 180° phase shifted voltage reference signal (VREF') having the DC component 76 and an oscillating component 36. As such the analog transmit signal 1 and the analog transmit signal 2 cancel each other out and no transmit signal is transmitted. The analog receive signal 35 includes a DC component 78 and an oscillating component 38 at a frequency $f_{\_RX}$. The analog receive signal 35 is an analog transmit signal transmitted by a drive-sense circuit or other transmit circuit of the test container and is representative of changes in electrical characteristics in the contents of the test container. As shown, the analog receive signal 35 has a greater magnitude in comparison to the analog RX signal 62.

FIG. 6 is a schematic block diagram of an embodiment of a first set of test container electrodes 16 coupled to a set of transmit circuits (drive sense circuits (DSCs) 1-4) and a second set of test container electrodes 16 coupled to a set of "receive only" differential drive sense circuits (DDSCs 1-4). Each DSC 1-4 is operable to transmit a transmit signal (TX_signal) at a particular frequency and receive a set of receive signals (RX_signals) from the other DSCs at a set of different frequencies. Each DDSC 1-4 is operable to receive a set of receive signals (RX_signals) from the DSCs at a set of different frequencies.

Because each of the DSCs 1-4 are operable to transmit and receive signals at different frequencies, each DSC 1-4 is able to obtain three different impedance measurements based on three different orientations within the test container 14. Because each of the DDSCs 1-4 are operable to receive signals from the DSCs 1-4, each DDSC 1-4 is able to obtain different four impedance measurements based on four different orientations within the test container 14. Different frequencies provide different impedance measurements for analysis. For example, the impedance of a capacitor (i.e., capacitor reactance) is equal to $1/(2\pi fC)$ where f is the frequency in Hz and C is the capacitance in farads.

FIG. 7 is a diagram of an example of a transmit signal and receive signals, in the frequency domain, of a drive sense circuit (DSC 4) and a receive signal of a "receive only" differential drive sense circuits (DDSC 1) of the embodiment of FIG. 6. Each DSC 1-4 is operable to transmit a transmit signal (TX_signal) at a particular frequency and receive a set of receive signals (RX_signals) at different frequencies from the other DSCs. For example, a DSC transmits a transmit signal at frequency f4 and is operable to receive a set of receive signals from the other three DSCs at frequencies f1-f3.

Each DDSC 1-4 is operable to receive a set of receive signals (RX_signals) at different frequencies from the DSCs. For example, a DDSC 1 is operable to receive a set of receive signals from the four DSCs at frequencies f1-f4.

FIG. 8 is a diagram of an example of a frequency pattern used by the drive-sense circuits (DSCs 1-4) of the embodiment of FIG. 6. In this example, the DSC 1 transmits a transmit signal at a frequency f_1, the DSC 2 transmits a transmit signal at a frequency f_2, the DSC 3 transmits a transmit signal at a frequency f_3, and the DSC 4 transmits a transmit signal at a frequency f_4. The DSCs 1-4 may transmit the transmit signals one at a time, all at the same time, or in a combination thereof.

The DSC 1 receives a set of receive signals from DSCs 2-4 at frequencies f_2, f_3, and f_4. The DSC 2 receives a set of receive signals from DSCs 1 and 3-4 at frequencies f_1, f_3, and f_4. The DSC 3 receives a set of receive signals from DSCs 1-2 and 4 at frequencies f_1, f_2, and. The DSC 4 receives a set of receive signals from DSCs 1-3 at frequencies f_1, f_2, and f_3. The DDSC 1 receives a set of receive signals from DSCs 1-4 at frequencies f_1, f_2, f_3, f_4. The DDSC 2 receives a set of receive signals from DSCs 1-4 at frequencies f_1, f_2, f_3, f_4. The DDSC 3 receives a set of receive signals from DSCs 1-4 at frequencies f_1, f_2, f_3, f_4. The DDSC 4 receives a set of receive signals from DSCs 1-4 at frequencies f_1, f_2, f_3, f_4.

Each of the four DSCs are operable to receive information from three different locations within a test container 14 (e.g., between 3 other DSCs and itself). Each of the four DDSCs are operable to receive information from four different locations within a test container 14 (e.g., between the 4 DSCs and itself).

FIG. 9 is a schematic diagram of an example of a generic circuit of a transmit drive-sense circuit (DSC_TX) and a "receive only" differential drive-sense circuit (DDSC_RX) of the embodiment of FIG. 6. Here, the DSC_TX is transmitting a transmit signal (TX_signal) at a frequency fx. The DDSC_RX receives a receive signal (RX_signal) at a frequency fx where the RX_signal at the frequency fx includes a representation of the electrical characteristics of contents of the test container 14 with respect to the orientation relationship between the DSC_TX and the DDSC_RX.

Figure 10:
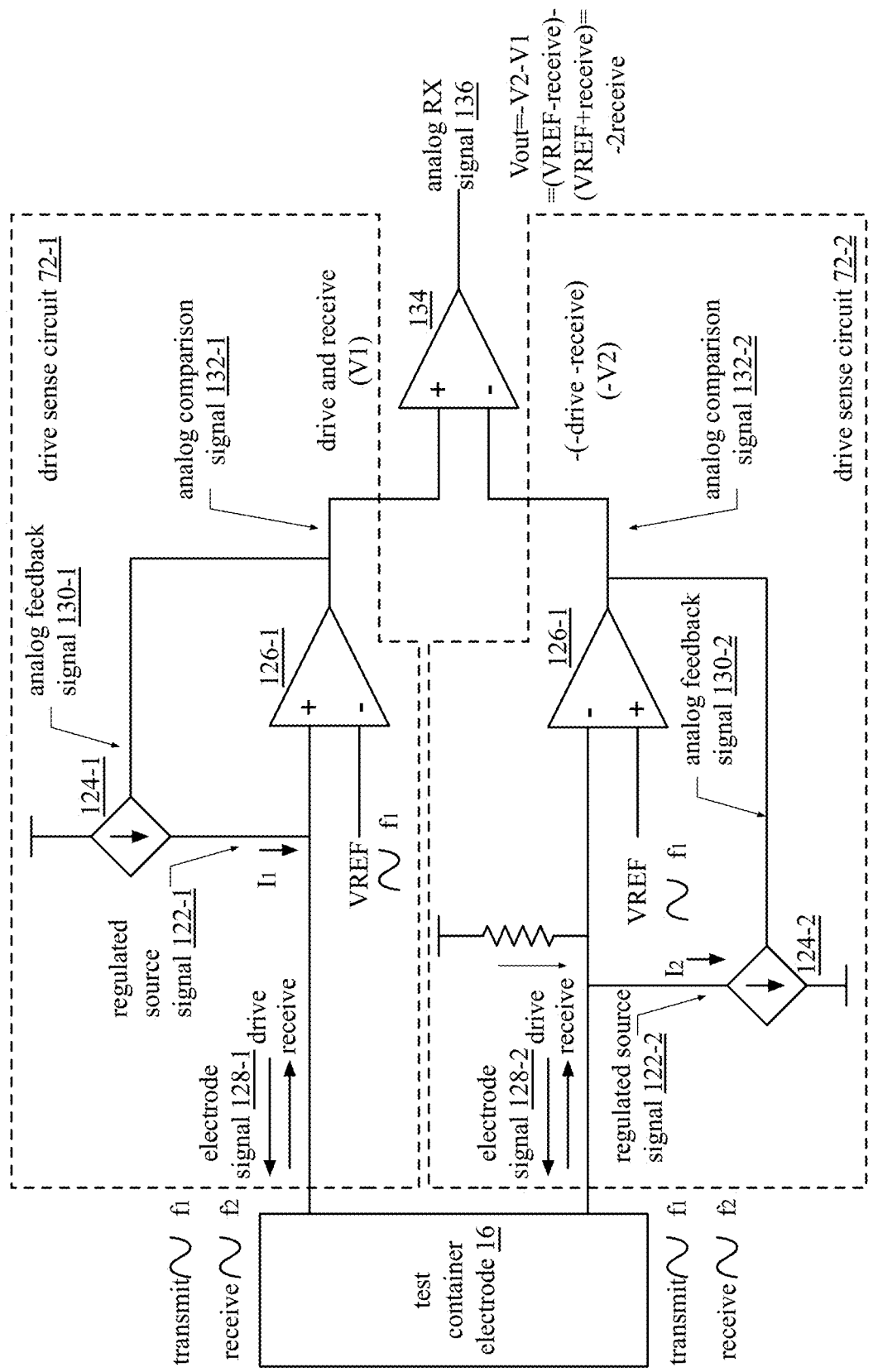
FIG. 10 is a schematic block diagram of an embodiment of a "transmit and receive" differential drive-sense circuit (DDSC) in accordance with the present invention.

FIG. 10 is a schematic block diagram of an embodiment of a "transmit and receive" differential drive-sense circuit (DDSC) 120 that includes drive-sense circuits 72-1 and 72-2 and an output operational amplifier (op-amp) 136. The drive-sense circuits 72-1 and 72-2 each include an op-amp 126-1 and 126-2, and a regulated current source circuit 124-1 and 124-2. Within the drive-sense circuit 72-1, the op-amp 126-1 is non-inverting and the positive input terminal of the op-amp 126-1 is coupled to a test container electrode 16 and the negative input terminal of the op-amp 126-1 is coupled to a voltage reference source (e.g., via a signal generator, via the processing module that generates and provides the voltage reference signal, etc.) that provides a voltage reference signal VREF. Within the drive-sense circuit 72-2, the op-amp 126-2 is inverting and the positive input terminal of the op-amp 126-2 is coupled to a voltage reference source that provides the voltage reference signal VREF and the negative input terminal of the op-amp 126-2 is coupled to the test container electrode 16.

The drive-sense circuits 72-1 and 72-2 operate similarly to the drive-sense circuits of previous Figures where the feedback loops function to keep the electrode signals 128-1 and 128-2 substantially matching the analog voltage reference signal (VREF). As such, the electrode signals 128-1 and 128-2 will have a similar waveform to that of the VREF (shown here having an oscillating component at f1).

The electrode signals 128-1 and 128-2 include a drive signal component and a receive signal component. The drive components of the electrode signals 128-1 and 128-2 (VREF and VREF) produce a transmit signal of 2VREF at f1. The receive signal components correspond to a received transmit signal at f2 produced by a DSC or another "transmit and receive" DDSC located at a different position in the test container.

The op-amp 126-1 of the drive-sense circuit 72-1 compares the electrode signal 128-1 to the VREF signal having the oscillating component frequency f1 to produce an analog comparison signal 132-1. The analog comparison signal 132-1 contains a representation of the receive signal having the oscillating component frequency f2 (e.g., the analog comparison signal 132-1 contains a representation of the VREF signal and the receive signal). The analog comparison signal 132-1 is fed back to the regulated current source circuit 124-1 as analog feedback signal 130-1. The regulated current source circuit 124-1 generates a regulated source signal 122-1 (e.g., a regulated current signal (I1)) based on the analog feedback signal 130-1. The regulated current signal (I1) in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. For example, if the impedance increases the voltage on the electrode, the regulated current signal (I1) provides more current to keep the voltage substantially equal to VREF.

The op-amp 126-2 of the drive-sense circuit 72-2 compares the electrode signal 128-2 to the VREF signal having the oscillating component frequency f1 to produce an analog comparison signal 132-2. The analog comparison signal 132-2 contains a representation of the receive signal having the oscillating component frequency f2 (e.g., the analog comparison signal 132-2 contains a representation of the VREF signal and the receive signal). The analog comparison signal 132-2 is fed back to the regulated current source circuit 124-2 as analog feedback signal 130-2. The regulated current source circuit 124-2 generates a regulated source signal 122-2 (e.g., a regulated current signal (I2)) based on the analog feedback signal 130-2. The regulated current signal (I2) in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. For example, if the impedance lowers the voltage on the electrode, the regulated current signal (I2) is increased to keep the voltage substantially equal to VREF.

The output op-amp 134 compares the analog comparison signal 132-1 and the analog comparison signal 132-2 to produce an analog receive (RX) signal 136. Comparing the analog comparison signal 132-1 and the analog comparison signal 132-2 removes the VREF components due to the inverting configuration of the op-amp 126-2 and doubles the receive component. As such, the differential drive-sense circuit 120 is more sensitive than the drive-sense circuit 72 at sensing very low signals since the sensed receive signal is doubled in comparison to the drive-sense circuit 72. Further, with the differential drive-sense circuit 120, because the VREF components are subtracted out, common mode noise is subtracted out. Therefore, the differential drive-sense circuit 120 is more sensitive and has better signal to noise ratio than the drive-sense circuit 72.

Additionally, the transmit signal produced by the differential drive-sense circuit 120 has twice the magnitude of the transmit signal of the drive-sense circuit 72 because the drive components combine. Therefore, the differential drive-sense circuit 120 could transmit signals using a lower magnitude VREF to reduce power and still transmit a similar transmit signal to a standard DSC. In another embodiment, the "transmit and receive" DDSC 120 includes an analog to digital converter (ADC) operable to convert the analog RX signal 136 to a digital sensed signal for input to a processing module.

FIG. 11 is a schematic block diagram of an embodiment of test container electrodes 16 coupled to "transmit and receive" differential drive sense circuits (DDSCs 1-8). Each DDSC 1-8 is operable to transmit a transmit signal (TX_signal) at a particular frequency and receive a set of receive signals (RX_signals) from the other DDSCs at a set of different frequencies.

Because each of the DSCs 1-8 are operable to transmit and receive signals at different frequencies, each DDSC 1-8 is able to obtain seven different impedance measurements based on three different orientations within the test container 14. Different frequencies provide different impedance measurements for analysis. For example, the impedance of a capacitor (i.e., capacitor reactance) is equal to $1/(2\pi fC)$ where f is the frequency in Hz and C is the capacitance in farads.

FIG. 12 is a diagram of an example of a transmit signal and receive signal, in the frequency domain, of a "transmit and receive" differential drive-sense circuit (DDSC 1) of the embodiment of FIG. 11. Each DDSC 1-8 is operable to transmit a transmit signal (TX_signal) at a particular frequency and receive a set of receive signals (RX_signals) at different frequencies from the other DDSCs. For example, a DDSC 1 transmits a transmit signal at frequency f1 and is operable to receive a set of receive signals from the other seven DDSCs at frequencies f2-f8.

FIG. 13 is a diagram of an example of a frequency pattern used by the "transmit and receive" differential drive-sense circuits (DDSCs 1-8) of the embodiment of FIG. 11. In this example, the DDSC 1 transmits a transmit signal at a frequency f_1, the DDSC 2 transmits a transmit signal at a frequency f_2, the DDSC 3 transmits a transmit signal at a frequency f_3, the DDSC 4 transmits a transmit signal at a frequency f_4, the DDSC 5 transmits a transmit signal at a frequency f_5, the DDSC 6 transmits a transmit signal at a frequency f_6, the DDSC 7 transmits a transmit signal at a frequency f_7, and the DDSC 8 transmits a transmit signal at a frequency f_8. The DDSCs may transmit the transmit signals one at a time, all at the same time, or in a combination thereof.

The DDSC 1 receives a set of receive signals from DDSCs 2-8 at frequencies f_2-f_8. The DDSC 2 receives a set of receive signals from DDSCs 1 and 3-8 at frequencies f_1 and f_3-f_8. The DDSC 3 receives a set of receive signals from DDSCs 1-2 and 4-8 at frequencies f_1-f_2 and f_4-f_8. The DDSC 4 receives a set of receive signals from DDSCs 1-3 and 5-8 at frequencies f_1-f_3 and f_5-f_8. The DDSC 5 receives a set of receive signals from DDSCs 1-4 and 6-8 at frequencies f_1-f_4 and f_6-f_8. The DDSC 6 receives a set of receive signals from DDSCs 1-5 and 7-8 at frequencies f_1-f_5 and f_7-f_8. The DDSC 7 receives a set of receive signals from DDSCs 1-6 and 8 at frequencies f_1-f_6 and f_8. The DDSC 8 receives a set of receive signals from DDSCs 1-7 at frequencies f_1-f_7.

Each of the eight DDSCs are operable to receive information from seven different locations within a test container 14 (e.g., between 7 other DDSCs and itself).

FIG. 14 is a schematic diagram of an example of a generic circuit of a transmit drive-sense circuit (DSC_TX) and a "transmit and receive" differential drive-sense circuit (DDSC_RX) of the embodiment of FIG. 11. Here, the DDSC_TX is transmitting a transmit signal (TX_signal) at a frequency fx. The DDSC_RX receives a receive signal (RX_signal) at a frequency fx where the RX_signal at the frequency fx includes a representation of the electrical characteristics of contents of the test container 14 with respect to the orientation relationship between the DDSC_TX and the DDSC_RX.

Figure 15:
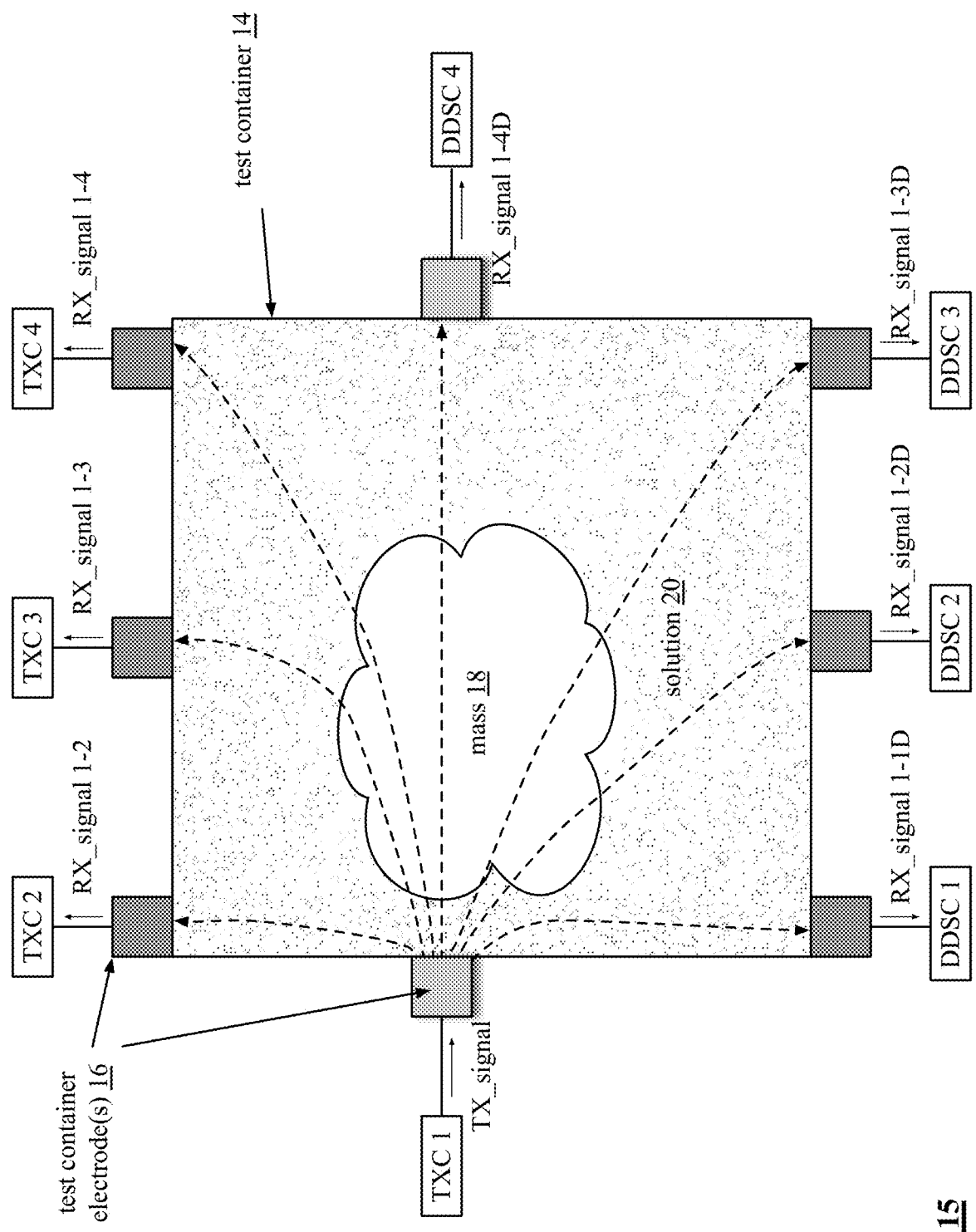
FIG. 15 is a schematic diagram of an example of a transmit circuit (TXC) transmitting a signal that is being received by the other TXCs and differential drive-sense circuits (DDSCs) within the embodiment of FIG. 6 or 11 in accordance with the present invention.

FIG. 15 is a schematic diagram of an example of a transmit (TX) circuit (TXC) transmitting a signal that is being received by other circuits of the test container 14. FIG. 15 includes a test container 14 including eight test container electrodes 16 where a first set of electrodes is coupled to transmit circuits (TXCs 1-4) and a second set of electrodes is coupled to differential drive-sense circuits (DDSCs 1-4). The TXCs 1-4 may be drive-sense circuits or "transmit and receive" differential drive-sense circuits. The differential drive-sense circuits (DDSCs 1-4) may be "receive only" differential drive-sense circuits or "transmit and receive" differential drive-sense circuits. The test container 14 contains a solution 20 and mass 18 (e.g., one or more cells, etc.).

The TXC 1 is transmitting a transmit signal TX_signal. The TXC 2 receives the RX_signal 1-2, where the RX_signal 1-2 is at the same frequency of TX_signal and includes a representation of the test container solution 20 impedance and the mass' 18 electrical characteristics measured with respect to TXC 2 from TXC 1. The TXC 3 receives the RX_signal 1-3, where the RX_signal 1-3 is at the same frequency of TX_signal and includes a representation of the test container solution 20 impedance and the mass' 18 electrical characteristics measured with respect to TXC 3 from TXC 1.

The TXC 4 receives the RX_signal 1-4, where the RX_signal 1-4 is at the same frequency of TX_signal and includes a representation of the test container solution 20 impedance and the mass' 18 electrical characteristics measured with respect to TXC 4 from TXC 1. The DDSC 1 receives the RX_signal 1-1D, where the RX_signal 1-1D is at the same frequency of TX_signal and includes a representation of the test container solution 20 impedance and the mass' 18 electrical characteristics measured with respect to DDSC 1 from TXC 1. The DDSC 2 receives the RX_signal 1-2D, where the RX_signal 1-2D is at the same frequency of the TX_signal and includes a representation of the test container solution 20 impedance and the mass' 18 electrical characteristics measured with respect to DDSC 2 from TXC 1.

The DDSC 3 receives the RX_signal 1-3D, where the RX_signal 1-3D is at the same frequency of the TX_signal and includes a representation of includes the test container solution 20 impedance and the mass' 18 electrical characteristics measured with respect to DDSC 3 from TXC 1. The DDSC 4 receives the RX_signal 1-4D, where the RX_signal 1-4D is at the same frequency of the TX_signal and includes a representation of the test container solution 20 impedance and the mass' 18 electrical characteristics measured with respect to DDSC 4 from TXC 1. As such, the impedance information obtained in the RX_signals 1-2 through 1-4 and 1-1D through 1-4D provides an impedance map of the materials present in the test container 14 (e.g., the solution 20 and the mass 18).

Figure 16:
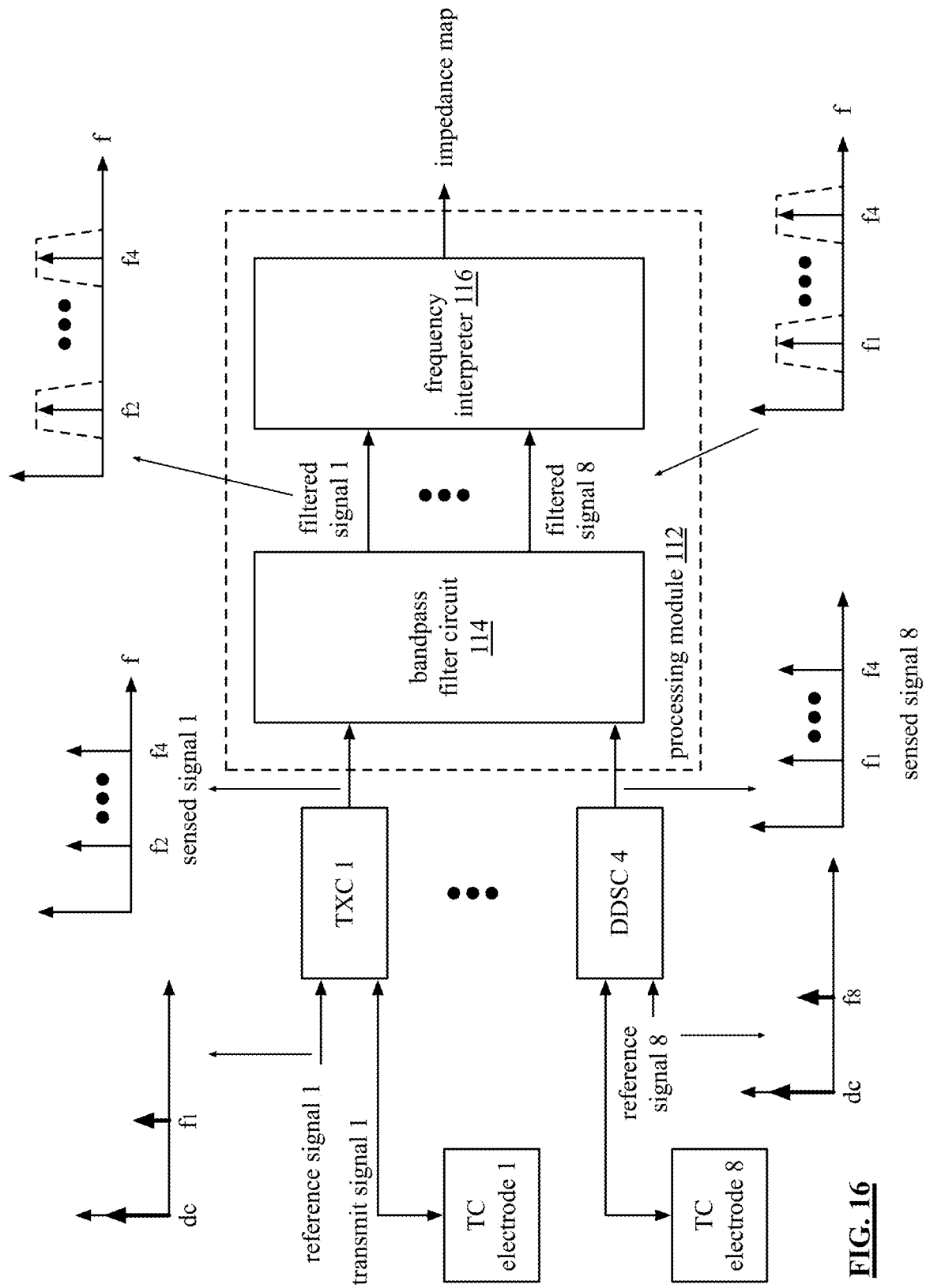
FIG. 16 is a schematic block diagram of an example of data processing of an organic and/or inorganic material test system in accordance with the present invention.

FIG. 16 is a schematic block diagram of an example of data processing of an organic and/or inorganic material test system that includes a processing module 112 (e.g., a test container processing module and/or the test container array processing module), test container (TC) electrodes 1-8 of a test container 14 of the test container array, a set of transmit circuits (TXs) 1-4 (e.g., drive-sense circuits) and a set of "receive only" differential drive-sense circuits (DDSCs) 1-4. In this example, the TXCs and DDSCs include analog to digital converters to output a digital sensed digital to the processing module 112. In another embodiment, the processing module 112 converts signals to the appropriate format for filtering. Sensed signals are sent to a processing module (e.g., a test container processing module and/or the test container array processing module) where they are processed to determine a set of impedance values (e.g., an impedance map) representative of the electrical characteristics of contents of the test container 14. The processing module 112 processes the impedance map to produce test container content electrical characteristic data with respect to the positioning of the electrodes and transmit frequencies.

The transmit circuits 1-4 provide transmit signals 1-4 to their respective test container electrodes 1-4 and produce respective sensed signals 1-4. The "receive only" DDSCs produce sensed signals 5-8. In an embodiment, the processing module 112 provides analog reference signals 1-4 to the transmit circuits 1-4 and analog reference signals 5-8 to the DDSCs 1-4. For example, each TXC and DDSC receives a unique analog reference signal.

The sensed signal 1 includes frequency components at $f_2$-$f_4$ that corresponds to the transmit signals of TXCs 2-4. As such, sensed signal 1 includes 3 different frequencies, which will produce 3 different impedance values. For example, impedance 1 is the impedance between TXC 1's electrode and TXC 2's electrode at frequency f2; impedance 2 is the impedance between TXC 1's electrode and TXC 3's electrode at frequency f3; and so on. The sensed signal 8 includes frequency components at $f_1$-$f_4$ that corresponds to transmit signals of TXCs 1-4. As such, sensed signal 8 includes 4 different frequencies, which will produce 4 different impedance values. For example, impedance 1 is the impedance between DDSC 4's electrode and TXC 1's electrode at frequency f1; impedance 2 is the impedance between DDSC 4's electrode and TXC 2's electrode at frequency f2; and so on.

The processing module 112 includes a bandpass filter 114 and a frequency interpreter 116. The bandpass filter circuit 114 passes (i.e., substantially unattenuated) signals in a bandpass region (e.g., tens of Hertz to hundreds of thousands of Hertz, or more) centered about frequencies $f_1$-$f_4$ and attenuates signals outside of the bandpass regions. The bandpass filter circuit 114 includes one or more digital filters, where a digital filter is implemented as a cascaded integrated comb (CIC) filter, a finite impulse response (FIR) filter, an infinite impulse response (IIR) filter, a Butterworth filter, a Chebyshev filter, an elliptic filter, etc. In another embodiment, the processing module obtains analog signals from the TXCs and DDSCs and performs one or more analog filtering techniques.

In this example, the processing module 112 filters the sensed signals 1-8 at different times in order to use the bandpass filter circuit 114 in a round robin fashion on the sensed signals 1-8. The processing module 112 may receive sensed signals 1-8 at the same or different times. For example, the processing module 112 receives sensed signals 1-8 from TXCs 1-4 and DDSCs 1-4 and the bandpass filter 114 filters sensed signal 1 at time T1 to produce a filtered signal 1, filters sensed signal 2 at time T2 to produce a filtered signal 2, filters sensed signal 3 at time T3 to produce a filtered signal 3, filters sensed signal 4 at time T4 to produce a filtered signal 4, filters sensed signal 5 at time T5 to produce a filtered signal 5, filters sensed signal 6 at time T6 to produce a filtered signal 6, filters sensed signal 7 at time T7 to produce a filtered signal 7, and filters sensed signal 8 at time T8 to produce a filtered signal 8.

The frequency interpreter 116 receives the filtered signal 1 at T1 and interprets it to render a first set of impedance values. As an example, the frequency interpreter 116 is a processing module, or portion thereof, that executes a function to convert the signal components of filtered signal 1 into the first set of impedance values, which are actual impedance values, relative impedance values (e.g., in a range), and/or difference impedance values (e.g., is the difference between a default impedance value and a sensed impedance value). As another example, the frequency interpreter 116 utilizes a look up table where the signal components of the filtered signal 1 are indexes for the table.

The frequency interpreter 116 produces eight sets of impedances (e.g., one for each TXC and DDSC) and further processes them to produce an impedance map of the test container per sampling interval. As an alternative to time multiplexing the use of four digital filters within the bandpass filter circuit 114, the bandpass filter circuit 114 includes 32 digital filters; four for each sensed signal.

Figure 17A:
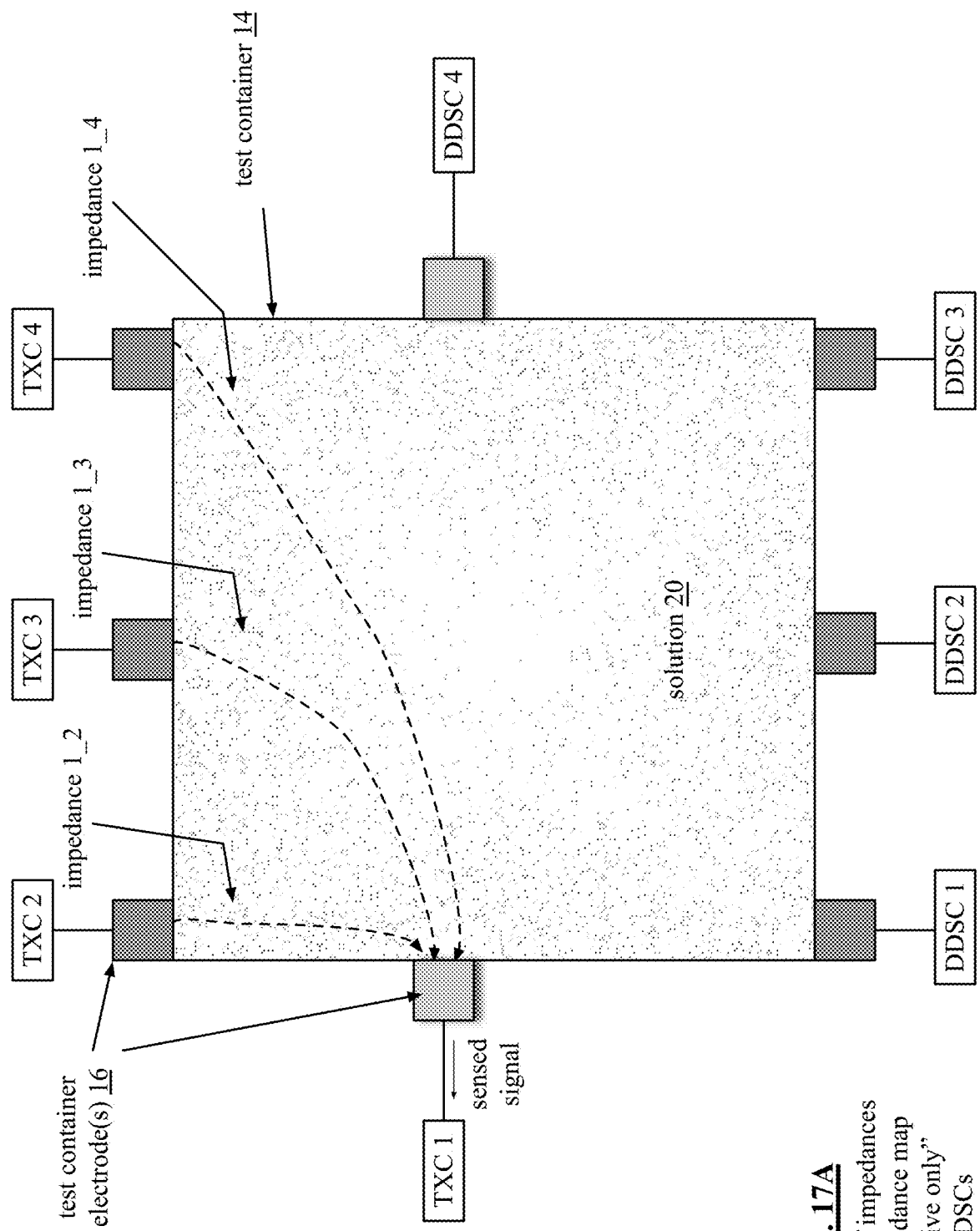
FIGS. 17A-17B are schematic block diagrams of an example of a first and second set of impedances of an impedance map in accordance with the present invention.

FIG. 17A is a schematic block diagram of an example of a first set of impedances of an impedance map of a test container 14 including a set of "receive only" differential drive-sense circuits (DDSCs 1-4) and a set of transmit circuits (TXCs 1-4) (e.g., a set of drive-sense circuits). The first set of impedances corresponds to a sensed signal (e.g., or an analog receive signal) produced by a transmit circuit (TXC) 1. TXCs 1-4 transmit signals at frequencies $f_1$-$f_4$. The sensed signal includes frequency components at $f_2$-$f_4$ corresponding to the transmit signals of TXCs 2-4. The sensed signal includes three different frequencies that produce three different impedance values.

For example, impedance 1_2 is the impedance between TXC 1's electrode and TXC2's electrode at frequency f2; impedance 13 is the impedance between TXC 1's electrode and TXC 3's electrode at frequency f3; and impedance 1_4 is the impedance between TXC 1's electrode and TXC 4's electrode at frequency f4.

Figure 17B:
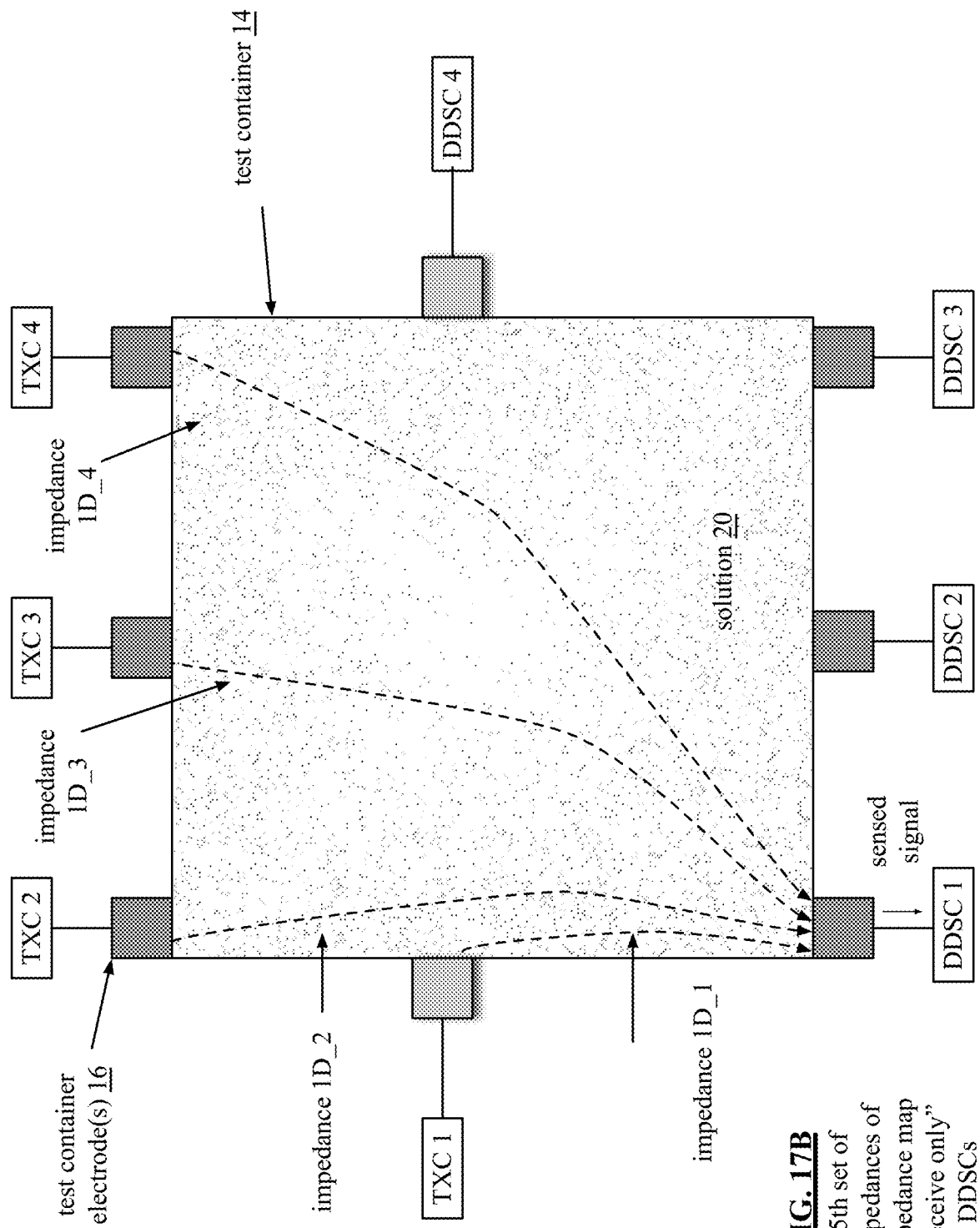

FIG. 17B is a schematic block diagram of an example of a fifth set of impedances of an impedance map of a test container 14 including a set of "receive only" differential drive-sense circuits (DDSCs 1-4) and a set of transmit circuits (TXCs 1-4) (e.g., a set of drive-sense circuits). The fifth set of impedances corresponds to a sensed signal produced by a DDSC 1. The TXCs 1-4 transmit signals at frequencies $f_1$-$f_4$. The sensed signal includes frequency components at $f_1$-$f_4$ corresponding to the transmit signals of the TXCs 1-4. The sensed signal includes four different frequencies that produce four different impedance values.

For example, impedance 1D_1 is the impedance between DDSC 1's electrode and TXC1's electrode at frequency f1; impedance 1D_2 is the impedance between DDSC 1's electrode and TXC 2's electrode at frequency f2; impedance 1D_3 is the impedance between DDSC 1's electrode and TXC 3's electrode at frequency f3; and impedance 1D_4 is the impedance between DDSC 1's electrode and TXC 4's electrode at frequency f4.

FIG. 18 is a schematic block diagram of an example of a test container impedance map 118 where the test container 14 includes a set of "receive only" differential drive-sense circuits (DDSCs) and a set of transmit circuits (TXCs) (e.g., drive-sense circuits). A processing module of a test system (e.g., one or more of a test container processing module and a test container array processing module) is operable to convert a sensed signal from a differential drive-sense circuit and/or a transmit circuit (e.g., a drive-sense circuit) into a set of impedances values (e.g., one or more impedance values). The processing module is further operable to generate and store a test container impedance map 118 that associates the sets of impedance values to their respective electrodes and physical placements within the testing container 14.

As shown, the first 4 sets of impedances each include 3 impedances: a transmit circuit receives the transmissions from the other 3 transmit circuits. The next 4 sets of impedances each include 4 impedances: a "receive only" DDSC receives the transmissions from the 4 transmit circuits. Note that the shaded impedances have a corresponding non-shaded impedance. For example, impedance 4-1 has a corresponding impedance 1-4. These impedance will be different since their reference signals are different (e.g., frequencies f1 and f4). While the impedances and frequencies are different, the resistive and reactive components between the first and fourth electrodes should be the same. Thus, from one or more of the two equations, the resistive and reactive components between the first and fourth electrodes (coupled to the first and fourth TXC) can be readily determined. For example, the resistance, capacitance, and/or inductance between the first and fourth electrodes can be readily determined (e.g., V=I*R, impedance of a capacitor is $\frac{1}{2\pi fC}$, and the impedance of an inductor is $2\pi fL$).

Figure 19:
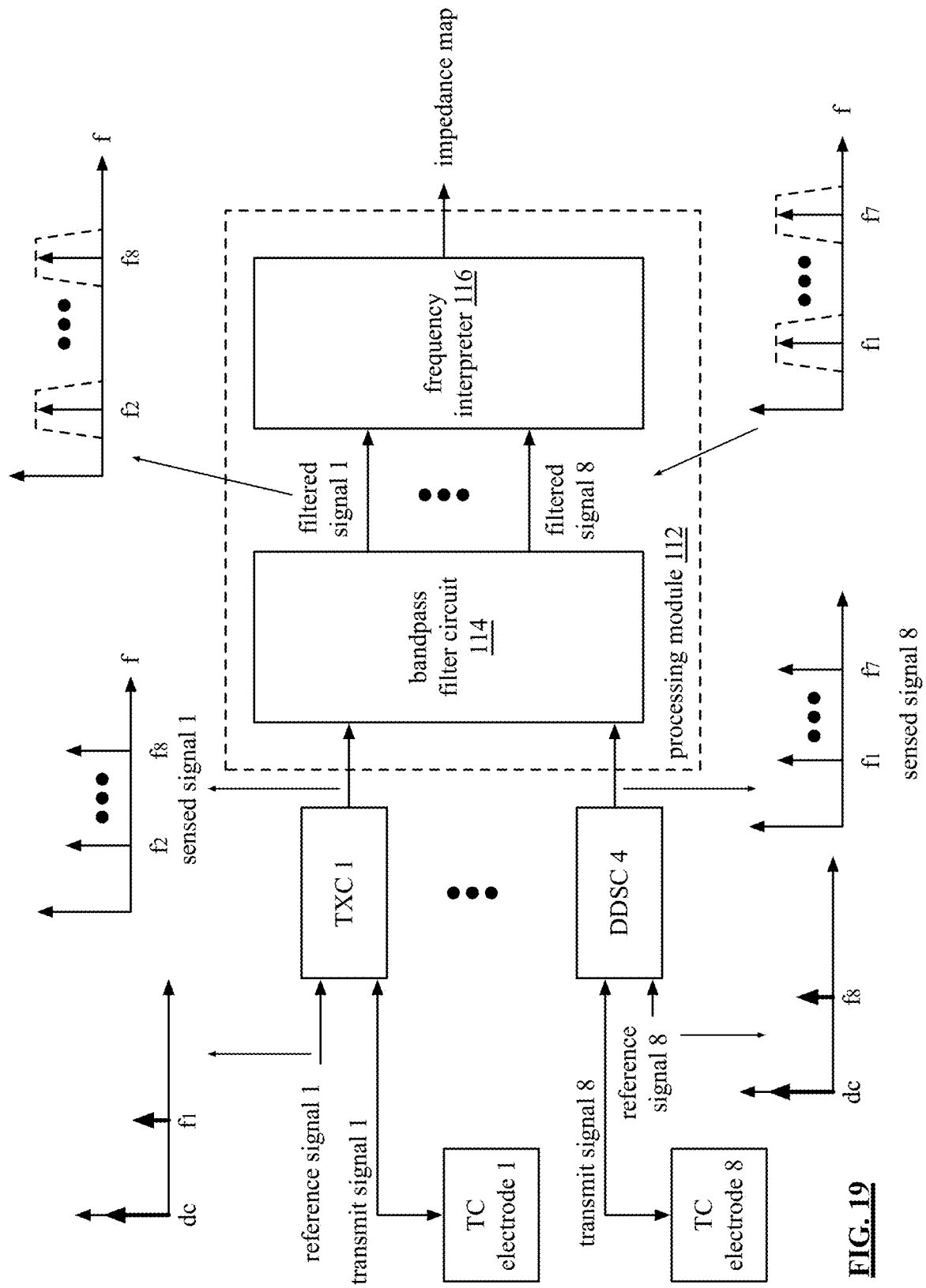
FIG. 19 is a schematic block diagram of an example of data processing of an organic and/or inorganic material test system in accordance with the present invention.

FIG. 19 is a schematic block diagram of an example of data processing of an organic and/or inorganic material test system that includes a processing module 112 (e.g., a test container processing module and/or the test container array processing module), test container (TC) electrodes 1-8 of a test container 14 of the test container array, a set of "transmit & receive" differential drive-sense circuits (DDSCs) 1-4, and a set of transmit circuits (TXs) 1-4 (e.g., drive-sense circuits or other transmit & receive DDSCs). In this example, the TXCs and DDSCs include analog to digital converters to output a digital sensed digital to the processing module 112. In another embodiment, the processing module 112 converts signals to the appropriate format for filtering.

Sensed signals are sent to a processing module (e.g., a test container processing module and/or the test container array processing module) where they are processed to determine a set of impedance values (e.g., an impedance map) representative of the electrical characteristics of contents of the test container 14. The processing module 112 processes the impedance map to produce test container content electrical characteristic data with respect to the positioning of the electrodes and transmit frequencies.

The transmit circuits 1-4 provide transmit signals 1-4 to their respective test container electrodes 1-4 and produce respective sensed signals 1-4. The "transmit and receive" DDSCs transmit signals 5-8 and produce sensed signals 5-8. In an embodiment, the processing module 112 provides analog reference signals 1-4 to the transmit circuits 1-4 and analog reference signals 5-8 to the DDSCs 1-4. For example, each TXC and DDSC receives a unique analog reference signal.

The sensed signal 1 includes frequency components at $f_2$-$f_8$ that corresponds to the transmit signals of TXCs 2-4 and DDSCs 1-4. As such, sensed signal 1 includes 7 different frequencies, which will produce 7 different impedance values. For example, impedance 1 is the impedance between TXC 1's electrode and TXC 2's electrode at frequency f2; impedance 2 is the impedance between TXC 1's electrode and TXC 3's electrode at frequency f3; and so on. The sensed signal 8 includes frequency components at $f_1$-$f_7$ that corresponds to transmit signals of TXCs 1-4 and DDSCs 1-3. As such, sensed signal 8 includes 7 different frequencies, which will produce 7 different impedance values. For example, impedance 1 is the impedance between DDSC 4's electrode and TXC 1's electrode at frequency f1; impedance 2 is the impedance between DDSC 4's electrode and TXC 2's electrode at frequency f2; and so on.

The processing module 112 includes a bandpass filter 114 and a frequency interpreter 116. The bandpass filter circuit 114 passes (i.e., substantially unattenuated) signals in a bandpass region (e.g., tens of Hertz to hundreds of thousands of Hertz, or more) centered about frequencies $f_1$-$f_8$ and attenuates signals outside of the bandpass regions. The bandpass filter circuit 114 includes one or more digital filters, where a digital filter is implemented as a cascaded integrated comb (CIC) filter, a finite impulse response (FIR) filter, an infinite impulse response (IIR) filter, a Butterworth filter, a Chebyshev filter, an elliptic filter, etc.

In this example, the processing module 112 filters the sensed signals 1-8 at different times in order to use the bandpass filter circuit 114 in a round robin fashion on the sensed signals 1-8. The processing module 112 may receive sensed signals 1-8 at the same or different times. For example, the processing module 112 receives sensed signals 1-8 from TXCs 1-4 and DDSCs 1-4 and the bandpass filter 114 filters sensed signal 1 at time T1 to produce a filtered signal 1, filters sensed signal 2 at time T2 to produce a filtered signal 2, filters sensed signal 3 at time T3 to produce a filtered signal 3, filters sensed signal 4 at time T4 to produce a filtered signal 4, filters sensed signal 5 at time T5 to produce a filtered signal 5, filters sensed signal 6 at time T6 to produce a filtered signal 6, filters sensed signal 7 at time T7 to produce a filtered signal 7, and filters sensed signal 8 at time T8 to produce a filtered signal 8.

The frequency interpreter 116 receives the filtered signal 1 at T1 and interprets it to render a first set of impedance values. As an example, the frequency interpreter 116 is a processing module, or portion thereof, that executes a function to convert the signal components of filtered signal 1 into the first set of impedance values, which are actual impedance values, relative impedance values (e.g., in a range), and/or difference impedance values (e.g., is the difference between a default impedance value and a sensed impedance value). As another example, the frequency interpreter 116 utilizes a look up table where the signal components of the filtered signal 1 are indexes for the table.

The frequency interpreter 116 produces eight sets of impedances (e.g., one for each TXC and DDSC) and further processes them to produce an impedance map of the test container per sampling interval. As an alternative to time multiplexing the use of eight digital filters within the bandpass filter circuit 114, the bandpass filter circuit 114 includes 56 digital filters; seven for each sensed signal.

Figure 20A:
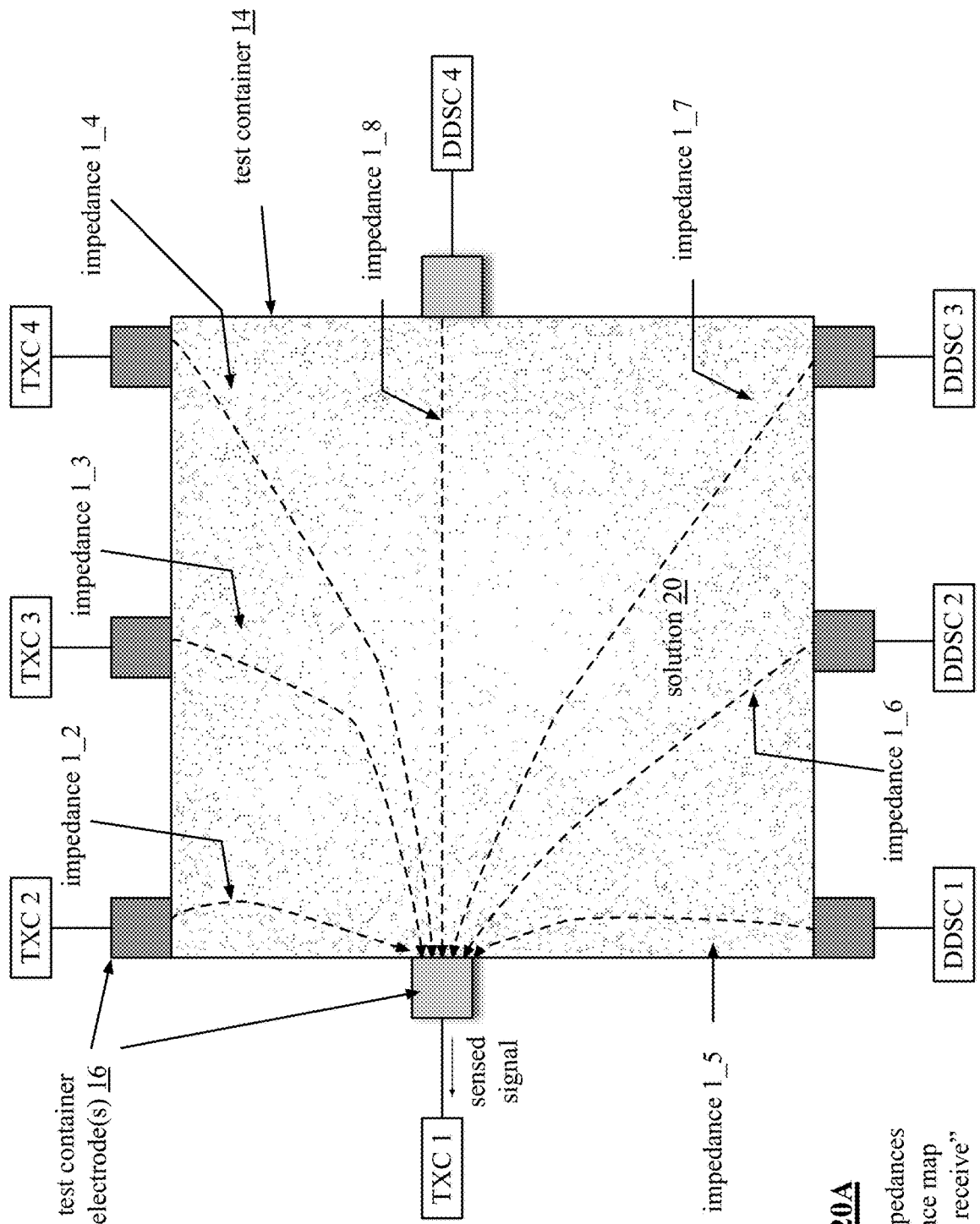
FIGS. 20A-20B are schematic block diagrams of an example of a first and second set of impedances of an impedance map in accordance with the present invention.

FIG. 20A is a schematic block diagram of an example of a first set of impedances of an impedance map of a test container including a set of "transmit and receive" differential drive-sense circuits (DDSCs) and a set of transmit circuits (TXCs) (e.g., drive sense circuits or other transmit and receive DDSCs). The first set of impedances corresponds to a sensed signal produced by a transmit circuit (TXC) 1. TXCs 1-4 transmit signals at frequencies $f_1$-$f_4$ and DDSCs 1-4 transmit signals at frequencies $f_4$-$f_8$. The sensed signal includes frequency components at $f_2$-$f_8$ corresponding to the transmit signals of TXCs 2-4 and DDSCs 1-4. The sensed signal includes seven different frequencies that produce seven different impedance values.

For example, impedance 1_2 is the impedance between TXC 1's electrode and TXC 2's electrode at frequency f2; impedance 1_3 is the impedance between TXC 1's electrode and TXC 3's electrode at frequency f3; impedance 1_4 is the impedance between TXC 1's electrode and TXC 4's electrode at frequency f4; impedance 15 is the impedance between TXC 1's electrode and DDSC 1's electrode at frequency f5; impedance 1_6 is the impedance between TXC 1's electrode and DDSC 2's electrode at frequency f6; impedance 17 is the impedance between TXC 1's electrode and DDSC 3's electrode at frequency f7; and impedance 18 is the impedance between TXC 1's electrode and DDSC 4's electrode at frequency f8.

Figure 20B:
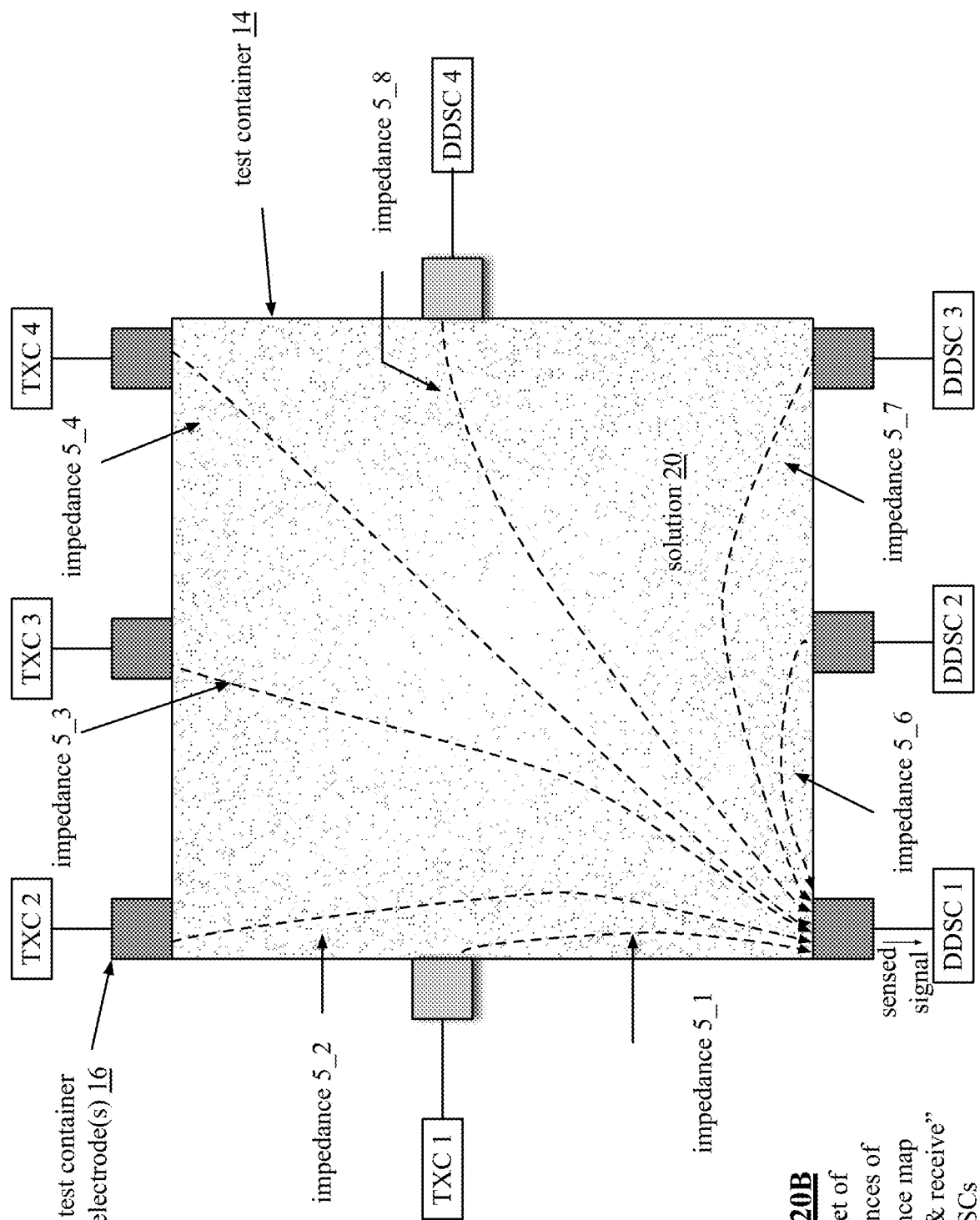

FIG. 20B is a schematic block diagram of an example of a fifth set of impedances of an impedance map of a test container including a set of "transmit and receive" differential drive-sense circuits (DDSCs) and a set of transmits circuits (TXCs) (e.g., drive-sense circuits or other transmit and receive" differential drive-sense circuits). The fifth set of impedances corresponds to a sensed signal produced by DDSC 1. TXCs 1-4 transmit signals at frequencies $f_1$-$f_4$ and DDSCs transmit signals at frequencies $f_5$-$f_8$. The sensed signal includes frequency components at $f_1$-$f_4$ and $f_6$-$f_8$ corresponding to the transmit signals of TXCs 1-4 and DDSCs 2-4. The sensed signal includes seven different frequencies that produce seven different impedance values.

For example, impedance 5_1 is the impedance between DDSC 1's electrode and TXC 1's electrode at frequency f1; impedance 5_2 is the impedance between DDSC 1's electrode and TXC 2's electrode at frequency f2; impedance 5_3 is the impedance between DDSC 1's electrode and TXC 3's electrode at frequency f3; impedance 5_4 is the impedance between DDSC 1's electrode and TXC 4's electrode at frequency f4; impedance 5_6 is the impedance between DDSC 1's electrode and DDSC 2's electrode at frequency f6; impedance 5_7 is the impedance between DDSC 1's electrode and DDSC 3's electrode at frequency f7; and impedance 5_8 is the impedance between DDSC 1's electrode and DDSC 4's electrode at frequency f8.

FIG. 21 is a schematic block diagram of an example of a test container impedance map 119 where the test container 14 includes a set of "transmit and receive" differential drive-sense circuits (DDSCs) and a set of transmit circuits (TXCs) (e.g., drive-sense circuits or other "transmit and receive" DDSCs). A processing module of a test system (e.g., one or more of a test container processing module and a test container array processing module) is operable to convert a sensed signal from a differential drive-sense circuit and/or a transmit circuit (e.g., a drive-sense circuit) into a set of impedances values (e.g., one or more impedance values). The processing module is further operable to generate and store a test container impedance map 119 that associates the sets of impedance values to their respective electrodes and physical placements within the test container 14.

As shown, each set of impedances includes 7 impedances: a DDSC or TXC receives the transmissions from the other DDSCs and TXCs to produce a set of impedances. Note that the shaded impedances have a corresponding non-shaded impedance. For example, impedance 7-1 has a corresponding impedance 1-7. These impedance will be different since their reference signals are different (e.g., frequencies f1 and f7). While the impedances and frequencies are different, the resistive and reactive components between the first and seventh electrodes should be the same. Thus, from one or more of the two equations, the resistive and reactive components between the first and seventh electrodes can be readily determined. For example, the resistance, capacitance, and/or inductance between the first and seventh electrodes can be readily determined (e.g., V=I*R, impedance of a capacitor is $1/2\pi fC$, and the impedance of an inductor is $2\pi fL$).

Figure 22:
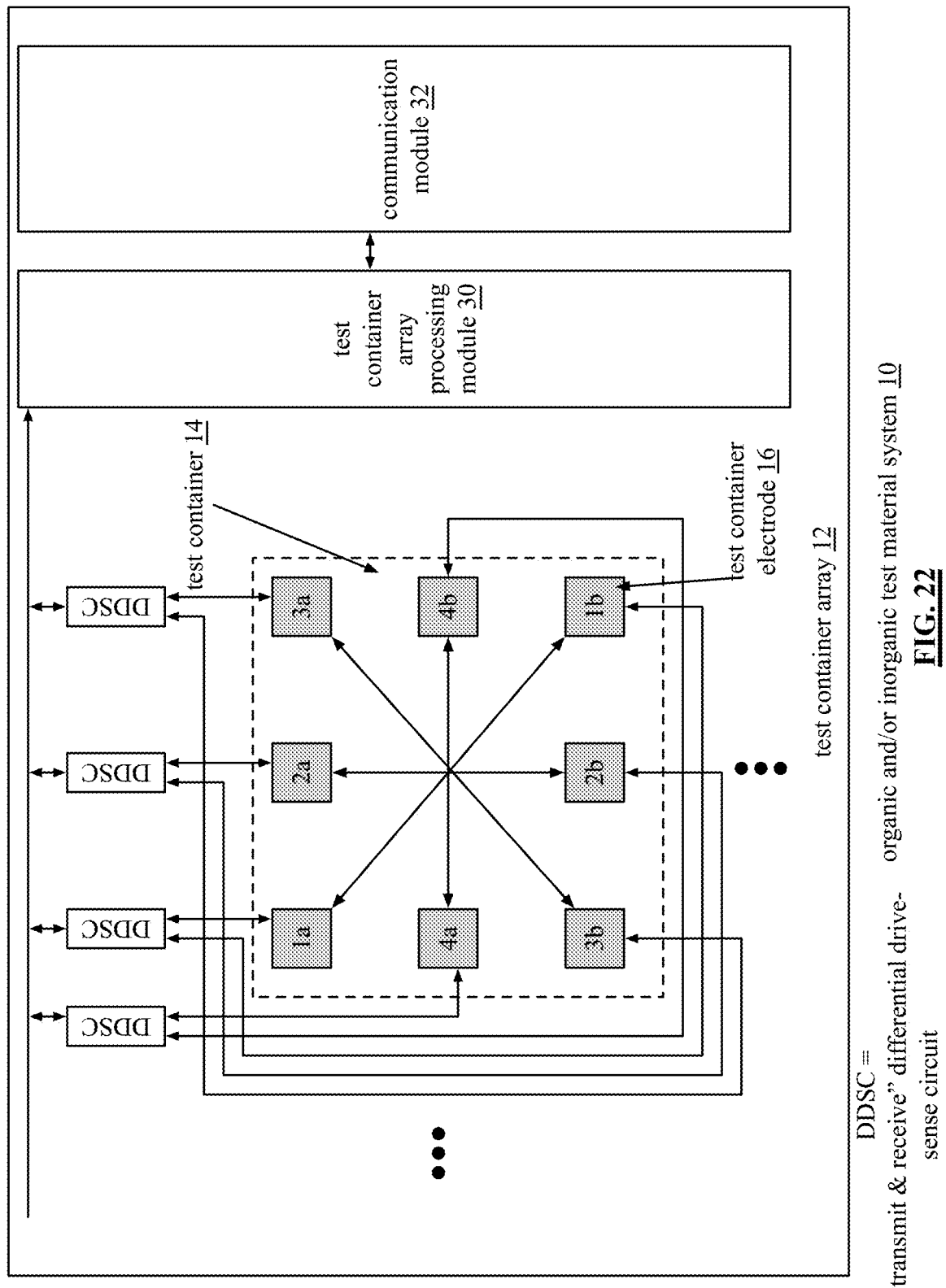
FIG. 22 is a schematic block diagram of an embodiment of an organic and/or inorganic material test system in accordance with the present invention.

FIG. 22 is a schematic block diagram of another embodiment of an organic and/or inorganic test system 10 that includes a test container array 12 including at least one test container 14, at least one differential pair of test container electrodes 16, at least one "transmit and receive" differential drive sense circuits (DDSCs), a test container array processing module 30, and a communication module 32.

Each test container 14 includes at least one differential pair of test container electrodes 16. For example, four differential pairs of test container electrodes 16 are included in a test container 14. Two of the four differential pairs of test container electrodes 16 may be near the bottom of the test container 14 and two of four differential pairs of test container electrodes 16 may be near a fill line of the test container 14.

A differential pair of test container electrodes 16 of the test container electrodes 16 is coupled to a "transmit and receive" differential drive-sense circuit (DDSC). The DDSCs are operable to provide transmit signals to the differential pair of test container electrodes 16 and detect changes in electrical characteristics of the differential pair of test container electrodes 16 without the use of electric field enhancers.

The test container array processing module 30 (i.e., the processing module) is described in greater detail at the end of the detailed description of the invention section. The test container array processing module 30 processes the detected changes in electrical characteristics of the test container electrodes 16 from DDSCs to determine the electrical characteristics of contents of a test container 14. For example, the test container array processing module 30 filters the data (e.g., via a bandpass filter) received from the DDSCs and interprets the filtered data to determine impedance values representative of the electrical characteristics of test container contents. As another example, the test container array processing module 30 performs a frequency sweep on the sensed signals generated by the DDSCs to produce a transfer function representative of electrical characteristics of the contents of the test container 14. The test container array processing module 30 is operable to analyze the transfer function to determine characteristics of the contents of the test container 14.

The test container array processing module 30 communicates the electrical characteristics of the contents to the communication module 32. Communicating the electrical characteristics of contents to the communication module 32 may include formatting the data in a particular format with respect to the communication protocol of the communication module. The communication module 32 is operable to communicate the electrical characteristics of cells via one or more communication protocols.

Figure 23:
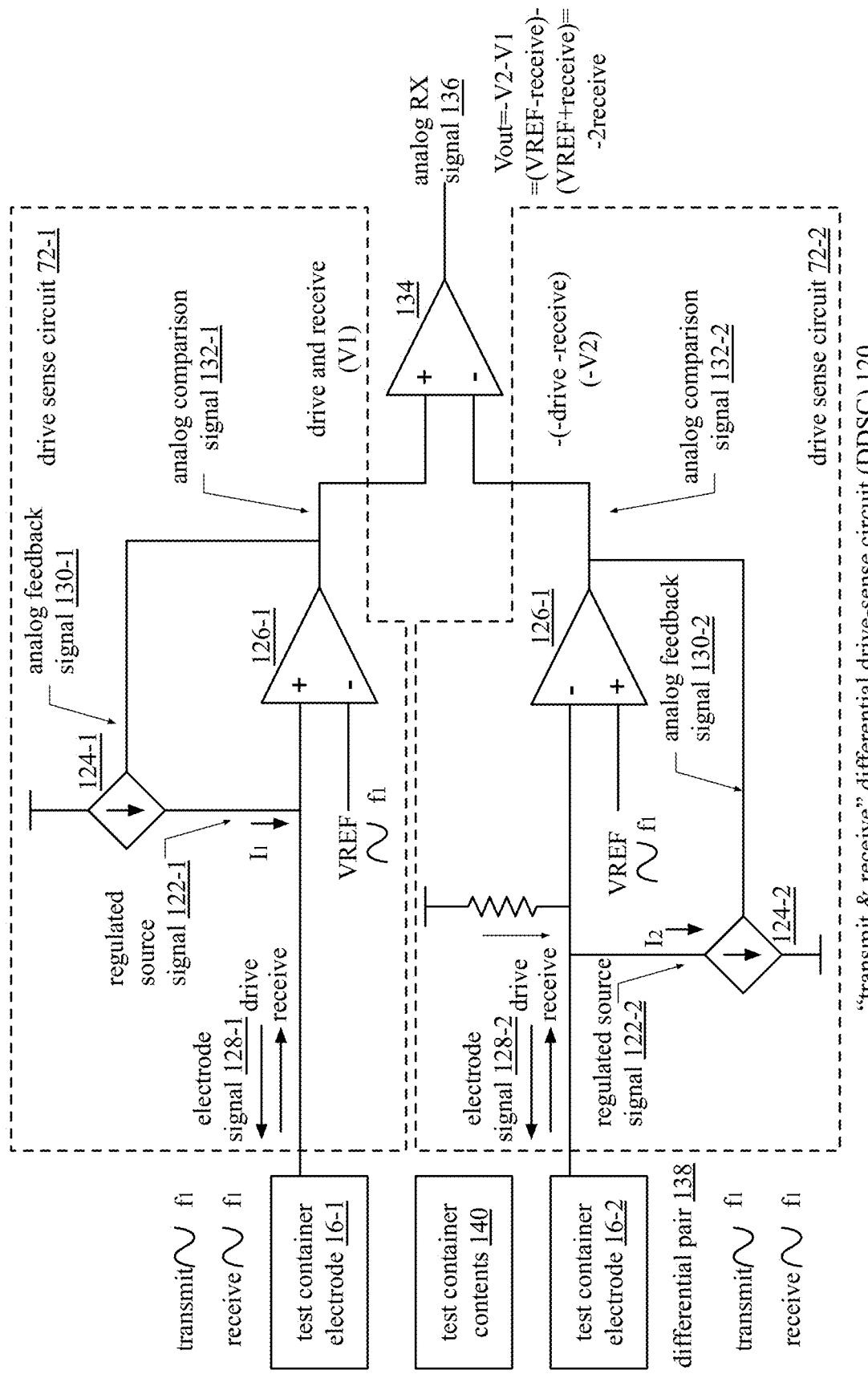
FIG. 23 is a schematic block diagram of an embodiment of a "transmit and receive" differential drive-sense circuit (DDSC) in accordance with the present invention.

FIG. 23 is a schematic block diagram of an embodiment of a "transmit and receive" differential drive-sense circuit (DDSC) 120 that includes drive-sense circuits 72-1 and 72-2 and an output operational amplifier (op-amp) 136. The differential drive-sense circuit (DDSC) 120 operates similarly to the "transmit and receive" differential drive-sense circuit (DDSC) 120 of FIG. 10 except that within the drive-sense circuit 72-1, the positive input terminal of the op-amp 126-1 is coupled to a first test container electrode 16-1 of a differential pair 138 of test container electrodes and within the drive-sense circuit 72-2, the negative input terminal of the op-amp 126-2 is coupled to a second test container electrode 16-1 of the differential pair 138.

The drive-sense circuits 72-1 and 72-2 operate similarly to the drive sense circuits of previous Figures where the feedback loops function to keep the electrode signals 128-1 and 128-2 substantially matching the analog voltage reference signal (VREF). As such, the electrode signals 128-1 and 128-2 will have a similar waveform to that of the VREF (shown here having an oscillating component at f1).

The electrode signals 128-1 and 128-2 include a drive signal component and a receive signal component. The drive components of the electrode signals 128-1 and 128-2 (VREF and VREF) produce transmit signals of VREF at f1. The receive signal includes a component corresponding to a received transmit signal at f1 transmitted by the other electrode of the differential pair of electrodes.

The op-amp 126-1 of the drive-sense circuit 72-1 compares the electrode signal 128-1 to the VREF signal having the oscillating component frequency f1 to produce an analog comparison signal 132-1. The analog comparison signal 132-1 contains a representation of the receive signal having the oscillating component frequency f1 (e.g., the analog comparison signal 132-1 contains a representation of the VREF signal and the receive signal). The analog comparison signal 132-1 is fed back to the regulated current source circuit 124-1 as analog feedback signal 130-1. The regulated current source circuit 124-1 generates a regulated source signal 122-1 (e.g., a regulated current signal (I1)) based on the analog feedback signal 130-1. The regulated current signal (I1) in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. For example, if the impedance increases the voltage on the electrode, the regulated current signal (I1) provides more current to keep the voltage substantially equal to VREF.

The op-amp 126-2 of the drive-sense circuit 72-2 compares the electrode signal 128-2 to the VREF signal having the oscillating component frequency f1 to produce an analog comparison signal 132-2. The analog comparison signal 132-2 contains a representation of the receive signal having the oscillating component frequency f1 (e.g., the analog comparison signal 132-2 contains a representation of the VREF signal and the receive signal). The analog comparison signal 132-2 is fed back to the regulated current source circuit 124-2 as analog feedback signal 130-2. The regulated current source circuit 124-2 generates a regulated source signal 122-2 (e.g., a regulated current signal (I2)) based on the analog feedback signal 130-2. The regulated current signal (I2) in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. For example, if the impedance lowers the voltage on the electrode, the regulated current signal (I2) is increased to keep the voltage substantially equal to VREF.

The output op-amp 134 compares the analog comparison signal 132-1 and the analog comparison signal 132-2 to produce an analog receive (RX) signal 136. Comparing the analog comparison signal 132-1 and the analog comparison signal 132-2 removes the VREF components due to the inverting configuration of the op-amp 126-1 and doubles the receive component.

Figure 23A:
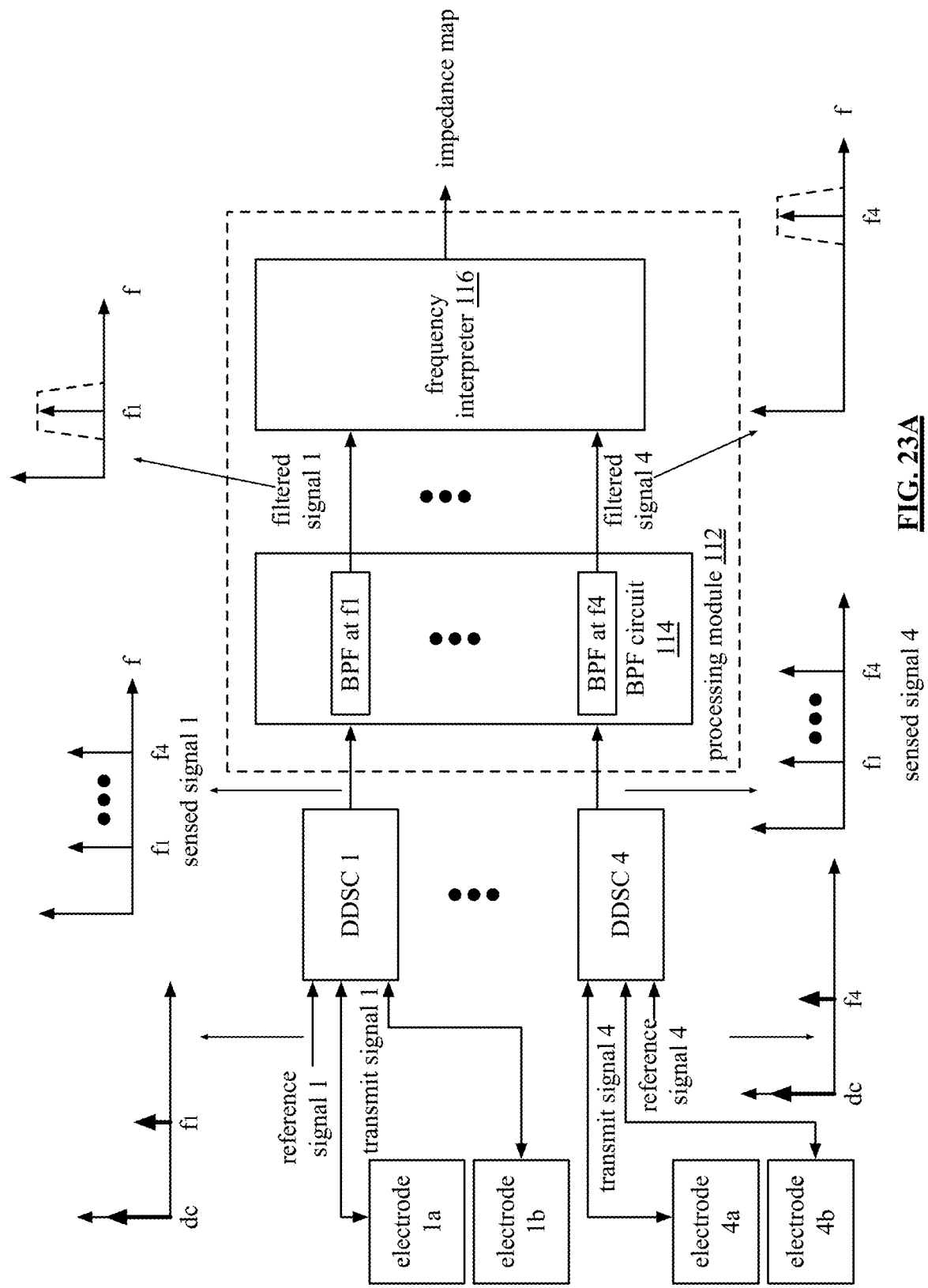
FIGS. 23A-23B are schematic block diagrams of examples of data processing of an organic and/or inorganic material test system in accordance with the present invention.
Figure 23B:
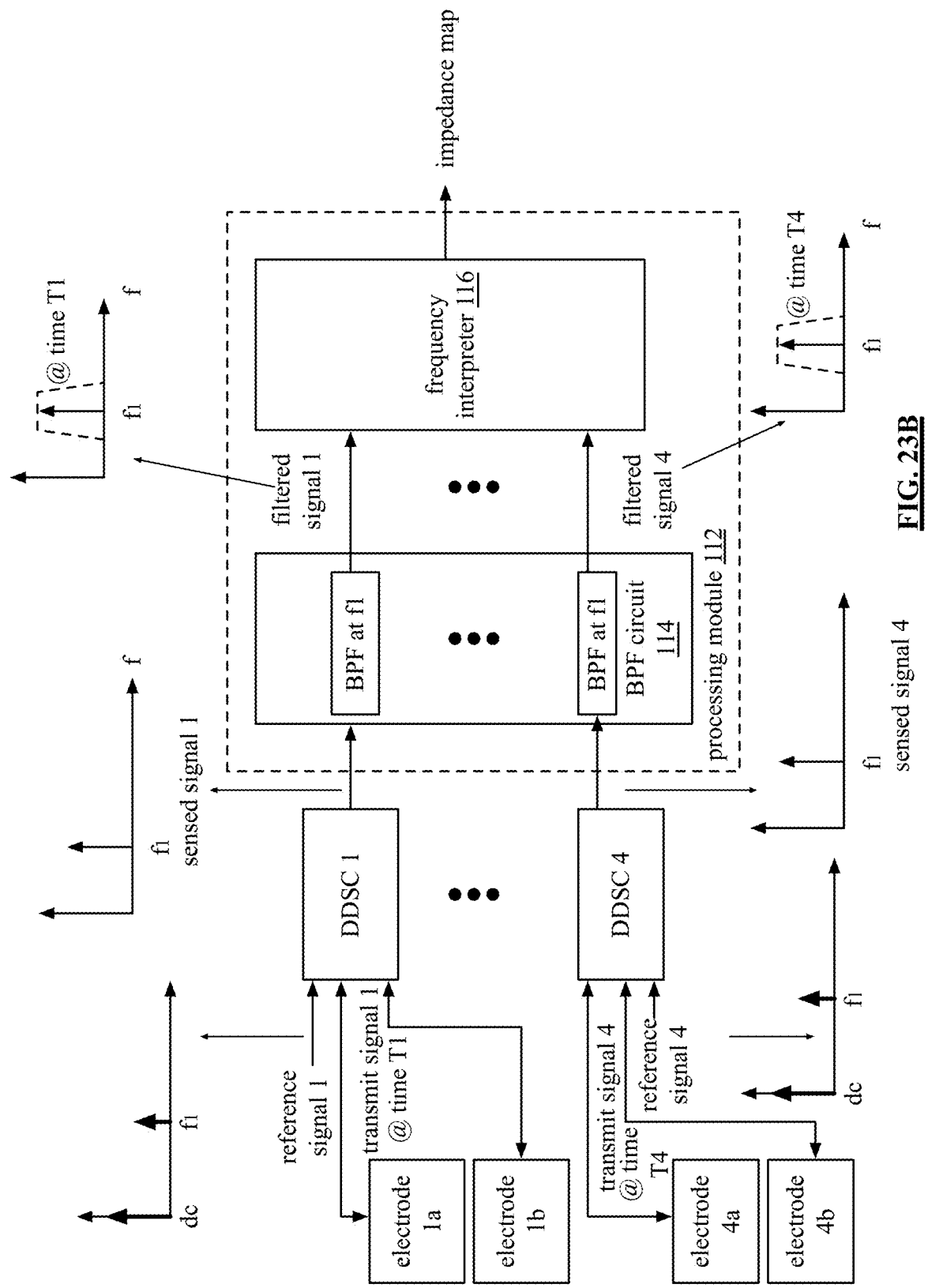

FIGS. 23A-23B are schematic block diagrams of embodiments of data processing of an organic and/or inorganic material test system that includes a processing module 112 (e.g., a test container processing module and/or the test container array processing module), differential pairs of test container electrodes 1a-4b of a test container 14 of the test container array, and a set of "transmit & receive" differential drive-sense circuits (DDSCs) 1-4. In this example, the DDSCs include analog to digital converters to output a digital sensed digital to the processing module 112. In another embodiment, the processing module 112 converts signals to the appropriate format for filtering.

Sensed signals are sent to a processing module (e.g., a test container processing module and/or the test container array processing module) where they are processed to determine a set of impedance values (e.g., an impedance map) representative of the electrical characteristics of contents of the test container 14. The processing module 112 processes the impedance map to produce test container content electrical characteristic data with respect to the positioning of the electrodes and transmit frequencies.

The "transmit and receive" DDSCs transmit signals 1-4 produce sensed signals 1-4. In FIG. 23A, the processing module 112 provides analog reference signals 1-4 to the DDSCs 1-4. For example, each DDSC receives a unique analog reference signal.

The sensed signal 1 includes frequency components at $f_1$-$f_4$ that corresponds to the transmit signals of DDSCs 1-4 (e.g., from the other electrode of the electrode pair and from other DDSCs of the test container). As such, sensed signal 1 includes 4 different frequencies, which will produce 4 different impedance values. For example, impedance 1 is the impedance between DDSC 1's electrode 1a and electrode 1b at frequency f1; impedance 2 is the impedance between DDSC 1's electrode 1a or electrode 1b and DDSC 2's electrode 2a or 2b at frequency f2; impedance 3 is the impedance between DDSC 1's electrode 1a or electrode 1b and DDSC 3's electrode 3a or 3b at frequency f3; and impedance 4 is the impedance between DDSC 1's electrode 1a or electrode 1b and DDSC 4's electrode 4a or 4b at frequency f4. The sensed signal 4 includes frequency components at $f_1$-$f_4$ that corresponds to transmit signals of DDSCs 1-4. As such, sensed signal 4 includes 4 different frequencies, which will produce 4 different impedance values. For example, impedance 1 is the impedance between DDSC 4's electrode 4a or electrode 4b and DDSC 1's electrode 1a or 1b at frequency f1; impedance 2 is the impedance between DDSC 4's electrode 4a or electrode 4b and DDSC 2's electrode 2a or 2b at frequency f2; impedance 3 is the impedance between DDSC 4's electrode 4a or electrode 4b and DDSC 3's electrode 3a or 3b at frequency f3; and impedance 4 is the impedance between DDSC 4's electrode 4a and electrode 4b at frequency f4.

The processing module 112 includes a bandpass filter 114 and a frequency interpreter 116. The bandpass filter circuit 114 passes (i.e., substantially unattenuated) signals in a bandpass region (e.g., tens of Hertz to hundreds of thousands of Hertz, or more) centered about frequencies $f_1$-$f_4$ and attenuates signals outside of the bandpass regions. The bandpass filter circuit 114 includes one or more digital filters, where a digital filter is implemented as a cascaded integrated comb (CIC) filter, a finite impulse response (FIR) filter, an infinite impulse response (IIR) filter, a Butterworth filter, a Chebyshev filter, an elliptic filter, etc.

In this example, the bandpass filter circuit includes bandpass filters (BPFs) centered about frequencies $f_1$-$f_4$. The processing module 112 receives sensed signals 1-4 from DDSCs 1-4. The bandpass filter centered about frequency $f_1$ of the bandpass filter circuit 114 filters sensed signal 1 to produce a filtered signal 1, the bandpass filter centered about frequency $f_2$ of the bandpass filter circuit 114 filters sensed signal 2 to produce a filtered signal 2, the bandpass filter centered about frequency $f_3$ of the bandpass filter circuit 114 filters sensed signal 3 to produce a filtered signal 3, and the bandpass filter centered about frequency $f_4$ of the bandpass filter circuit 114 filters sensed signal 4 to produce a filtered signal 4.

The frequency interpreter 116 receives the filtered signals 1-4 and produces a set of impedance values. As an example, the frequency interpreter 116 is a processing module, or portion thereof, that executes a function to convert the signal components of filtered signal 1 into an impedance value, which is an actual impedance value, a relative impedance value (e.g., in a range), and/or a difference impedance value (e.g., is the difference between a default impedance value and a sensed impedance value). As another example, the frequency interpreter 116 utilizes a look up table where signal components of the filtered signal 1 are indexes for the table.

The frequency interpreter 116 produces four impedances (e.g., one for each DDSC) and further processes them to produce an impedance map of the test container per sampling interval.

FIG. 23B operates similarly to FIG. 23A except that a multiplexor and/or the processing module 112 selects a reference signal input for each DDSC such that the DDSCs transmit signals one at a time using the same frequency. For example, a reference signal at a frequency f1 is selected as the transmit signal for each DDSC. The sensed signals 1-4 each include a frequency components at $f_1$ corresponding to the transmit signal produced by the DDSC that is currently transmitting.

In this example, the bandpass filter circuit includes bandpass filters (BPFs) centered about frequencies $f_1$. The processing module 112 receives sensed signals 1-4 from DDSCs 1-4 at times T1-T4. The bandpass filter centered about frequency $f_1$ of the bandpass filter circuit 114 filters sensed signals 1-4 to produce filtered signals 1-4 at different times T1-T4. In an example, when DDSC 1 is transmitting, the sensed signals 1-4 includes frequency components at $f_1$ that corresponds to the transmit signal of DDSC 1. The bandpass filter circuit 114 filters the sensed signal 1 at time T1 at the frequency $f_1$ to produce a filtered signal 1 at the frequency $f_1$. The bandpass filter circuit 114 filters the sensed signal 2 at time T2 at the frequency $f_1$ to produce a filtered signal 2 at the frequency $f_1$ and so on. The frequency interpreter 116 receives the filtered signals 1-4 and interprets it to render a first set of impedance values. As such, 4 different impedance values are provided at the same frequency.

Figure 24:
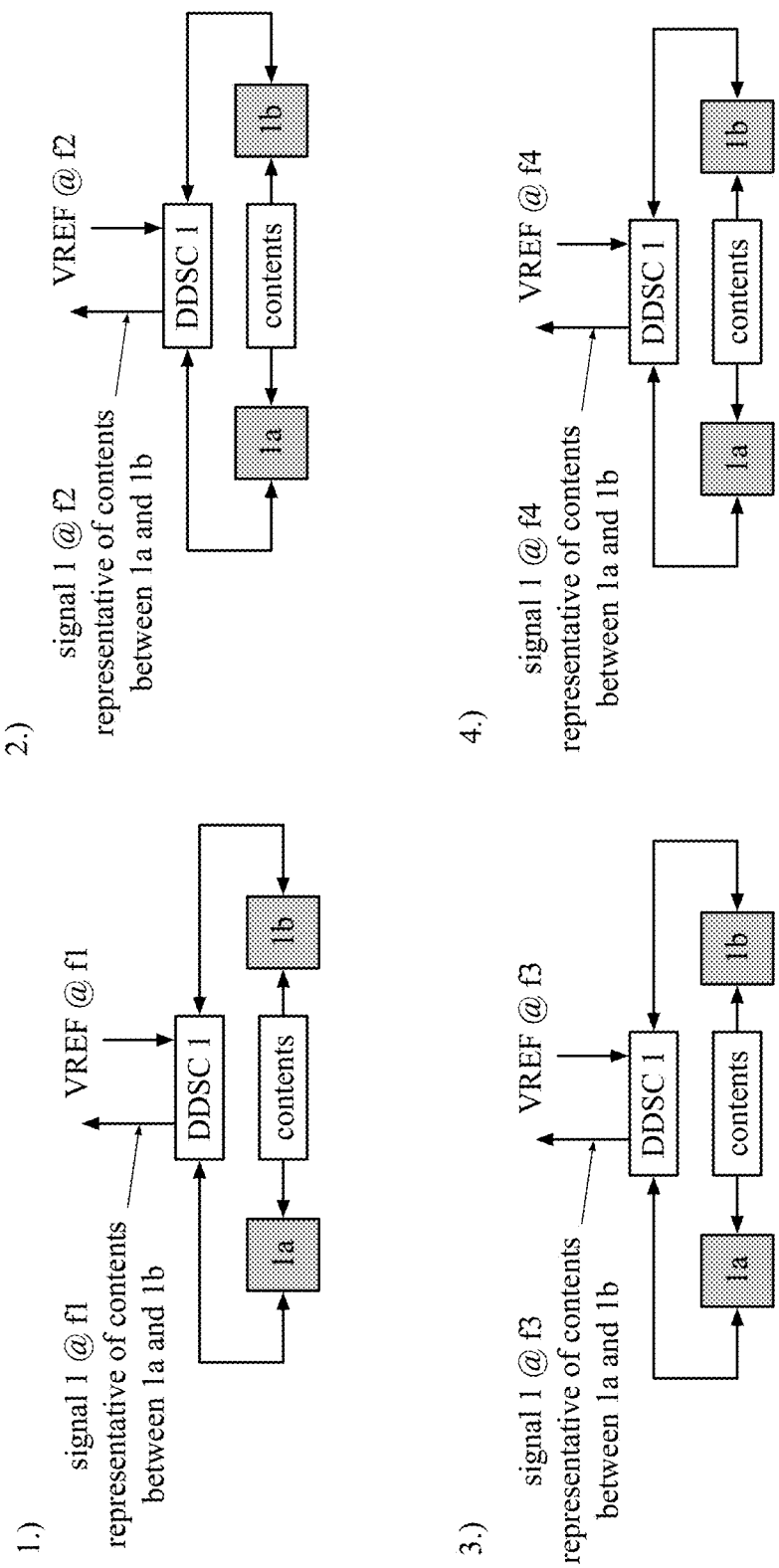
FIG. 24 is a schematic block diagram of an organic and/or inorganic material test system in accordance with the present invention.

FIG. 24 is a schematic block diagram of an example of normalizing a signal generated by a "transmit and receive" differential drive-sense circuit coupled to a differential pair of electrodes. FIG. 24 includes a differential pair electrodes (electrodes 1a and 1b) coupled to a "transmit and receive" differential drive-sense circuit (DDSC 1). A voltage reference signal (VREF) is provided as an input to DDSC 1. VREF can be generated having different oscillating components. For example at step 1, a VREF signal having an oscillating component with a frequency f1 is provided to DDSC 1 and an analog receive signal 1 is generated having the oscillating component with a frequency f1.

At step 2, a VREF signal having an oscillating component with a frequency f2 is provided to DDSC 1 and an analog receive signal 1 is generated having the oscillating component with a frequency f2. At step 3, a VREF signal having an oscillating component with a frequency f3 is provided to DDSC 1 and an analog receive signal 1 is generated having the oscillating component with a frequency f3. At step 4, a VREF signal having an oscillating component with a frequency f4 is provided to DDSC 1 and an analog receive signal 1 is generated having the oscillating component with a frequency f4.

At step 5, each analog receive signal 1 produced from receiving a transmit signal at frequencies f1, f2, f3, and f4 can be normalized to eliminate and/or compare any differences between the signals. For example, the processing module determines a mean signal and standard deviation for signal 1 and normalizes signal 1 based on those terms.

Figure 25B:
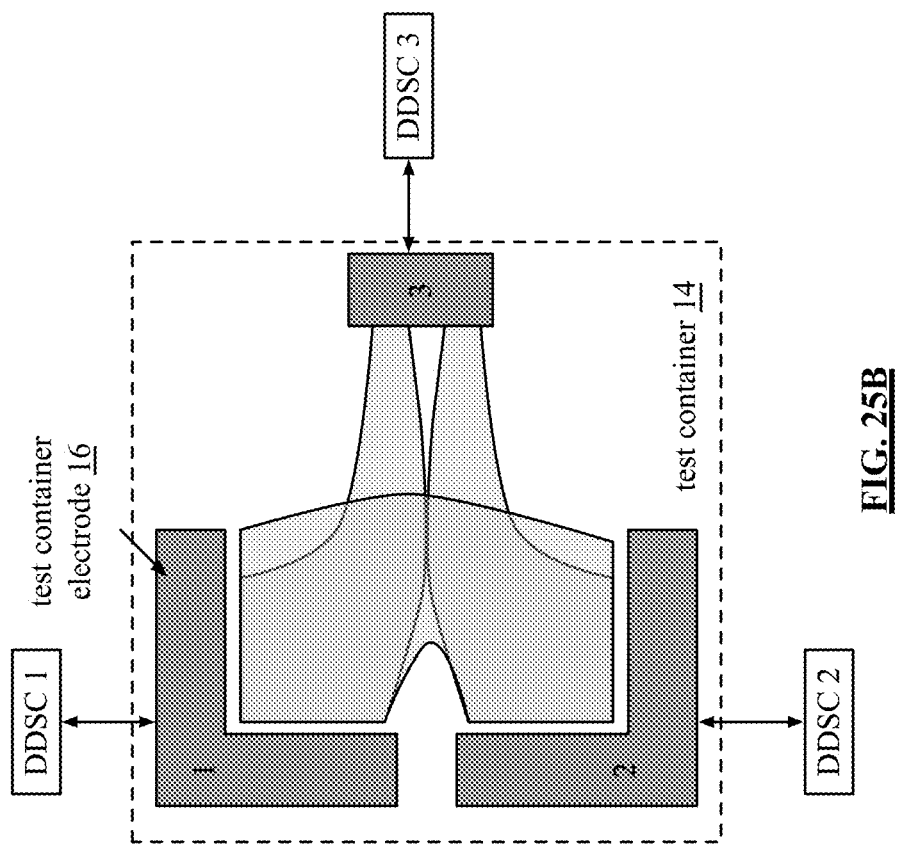
FIGS. 25A-25B are schematic block diagrams of examples of shaped electrodes of an organic and/or inorganic material test system in accordance with the present invention.
Figure 25A:
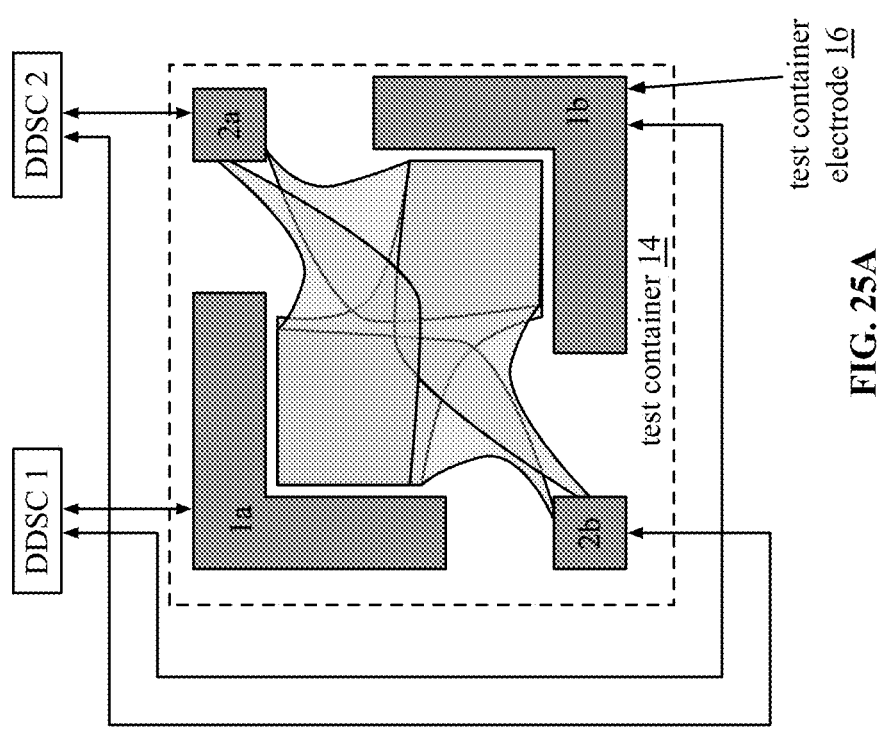

FIGS. 25A-25B are schematic block diagrams of a test container 14 that includes shaped test container electrodes 16. In FIG. 25A, a differential pair of electrodes 1a and 1b are coupled to a "transmit and receive" differential drive-sense circuit (DDSC 1) and a differential pair of electrodes 2a and 2b are coupled to a "transmit and receive" differential drive-sense circuit (DDSC 2). The differential pair of electrodes 1a and 1b are "L" shaped and positioned on opposite corners of the test container 14 taking up more area of the test container perimeter than previously shown electrodes. The differential pair of electrodes 2a and 2b are similar size and shape to previously shown electrodes and are positioned on opposite corners of the test container 14.

The electrodes 1a and 1b transmit and receive signals through a larger area of the testing container 14 such that impedances measured based on received signals are representative of this larger area (e.g., the shaded areas between electrodes). The size and shape of the electrodes can be adjusted and/or selected in accordance with desired testing materials and methods of testing. For example, many small electrodes may be required to get accurate information on extremely small organic and/or inorganic materials. As another example, when the location of the organic and/or inorganic material is fixed and known in the testing container, the electrodes can be positioned around that particular area. As another example, when position of the organic and/or inorganic material is large and/or unimportant (e.g., the biological material fills the entire testing container, is unlikely to change position and/or shape during testing, etc.), shaped electrodes of larger sizes could be used.

In FIG. 25B, three test container electrodes 1-3 are coupled to differential drive-sense circuits DDSC 1-DDSC 3 (e.g., they are not differential pair electrodes). The electrodes 1-2 are "L" shaped and positioned on corners of same side of the test container 14 taking up almost half the perimeter of one side of the test container 14. The electrode 3 is a similar size and shape to previously shown electrodes and is positioned on the opposite side of the test container 14 to electrodes 1-2.

The electrodes 1 and 2 transmit and receive signals through a larger area of the testing container 14 such that impedances measured based on received signals are representative of this larger area (e.g., the shaded areas between electrodes). The size and shape of the electrodes can be adjusted and/or selected in accordance with desired testing materials and methods of testing.

Figure 26:
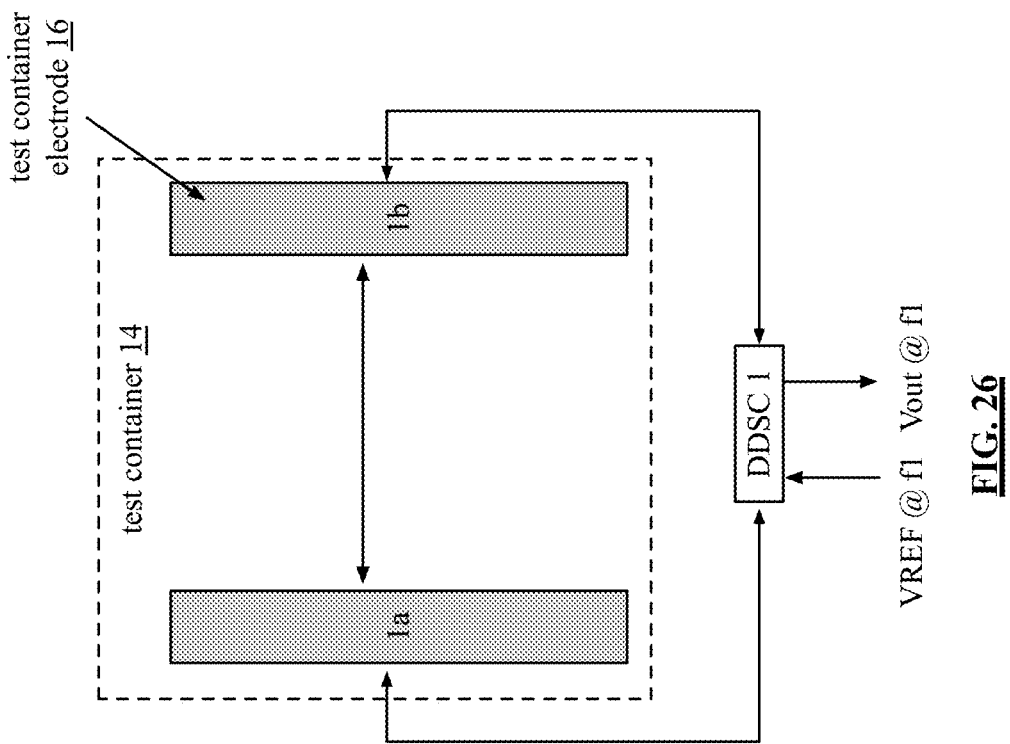
FIG. 26 is a schematic block diagram of an embodiment of a test container including a differential pair of electrodes coupled to a differential drive-sense circuit (DDSC) in accordance with the present invention.

FIG. 26 is a schematic block diagram of an embodiment of a test container 14 including a differential pair of electrodes 1a and 1b coupled to a "transmit and receive" differential drive-sense circuit (DDSC 1). The DDSC 1 operates similarly to "transmit and receive" differential drive sense circuits of previous Figures. An analog voltage reference signal (VREF) is input to the DDSC 1 and a voltage signal Vout is outputted. The VREF signal includes an oscillating component at a frequency f1 and a DC component. As such, Vout also includes an oscillating component at frequency f1 and a DC component. The Vout signal contains a representation of electrical characteristics of contents of the test container 14. Other configurations of the test container 14 are possible. For example, each electrode is coupled to its own DDSC.

Figure 27:
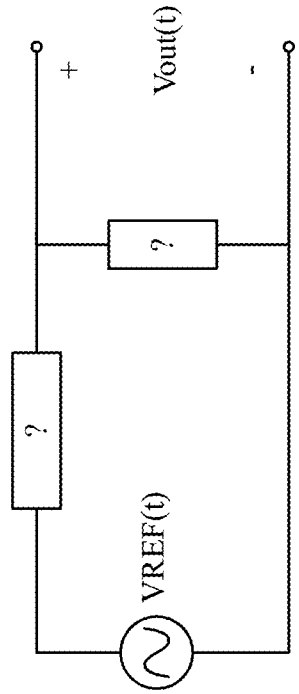
FIG. 27 is a schematic block diagram of an example of a circuit equivalent of the test container of FIG. 26 in accordance with the present invention.

FIG. 27 is a schematic block diagram of an example of a circuit equivalent of the test container 14 of FIG. 26. The test container 14 can be modeled as a circuit having an alternating current (AC) voltage source VREF(t) (e.g., in the time domain) and some unknown impedance where Vout is measured across an impedance. The circuit may include one or more voltage and/or current sources generated by an organic and/or inorganic material present in the test container.

Figure 28:
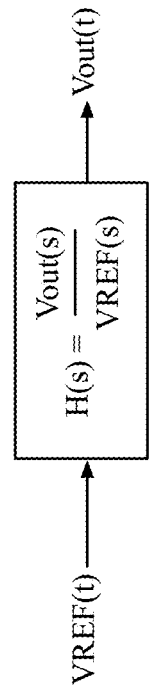
FIG. 28 is a schematic block diagram of an example of a transfer function representation of test container contents of FIG. 26 in accordance with the present invention.

FIG. 28 is a schematic block diagram of an example of a transfer function representation of the test container contents of FIG. 26. A transfer function is a mathematical function which theoretically models a device or system's output for each possible input. The term transfer function is also used in frequency domain analysis of systems using transform methods such as a Laplace transform where the amplitude of the output is a function of the frequency of the input signal. The simplest representation of a system is through ordinary differential equations. When dealing with ordinary differential equations, the dependent variables are a function of a real positive variable (often time). For example, x(t) (in the time domain) models a system's output y(t) for each possible input x(t). By applying the Laplace transform, the function of time is switched to a function of a complex variable s (frequency) (e.g., x(t) becomes X(s) and y(t) becomes Y(s)) and the differential equation becomes an algebraic equation.

The transfer function of the circuit equivalent of the test container 27 shown in FIG. 27 in the s-domain (i.e., from doing a Laplace transform) is H(s)=output signal/input signal or H(s)=Vout/VREF. By conducting a frequency sweep of the input signal VREF, the transfer function related to Vout can be generated, and impedance information of the equivalent circuit can be determined and analyzed.

For example, all transfer functions have some number of constants, poles and/or zeros at the origin, poles and/or zeros not at the origin, and/or complex poles and/or zeros. Poles of a transfer function are the frequencies (values of s) for which the denominator of the transfer function becomes zero. Zeros of a transfer function are the frequencies (values of s) for which the numerator of the transfer function becomes zero. Depending on the poles, zeros, and/or constants found in the transfer function generated, electrical characteristics (e.g., impedance) of the test container contents can be determined.

Figure 29F:
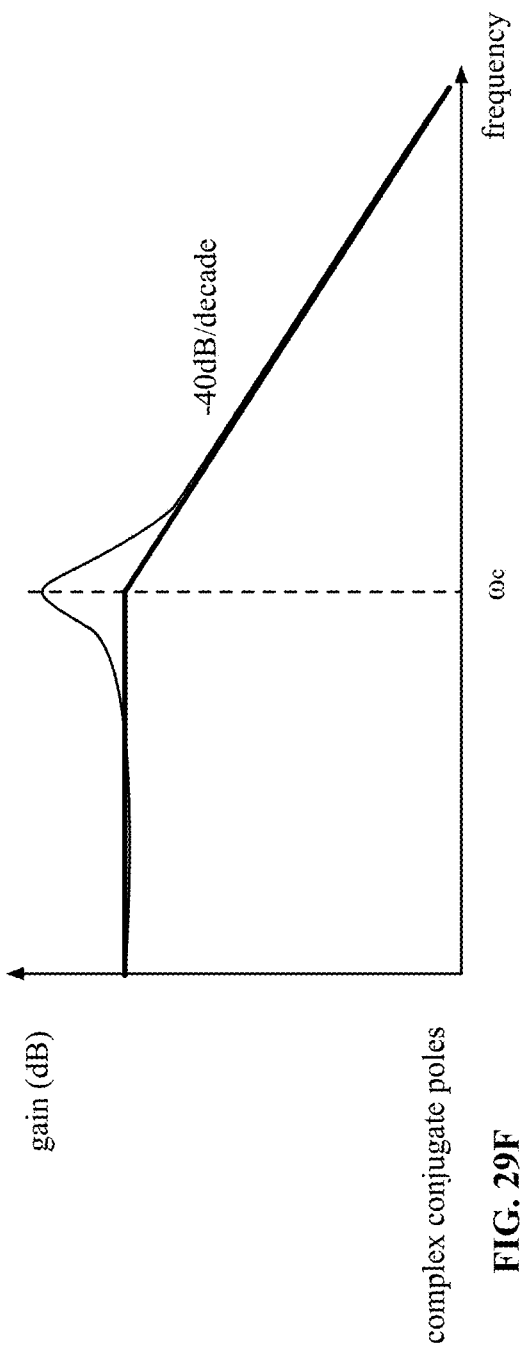

FIGS. 29A-29G are schematic block diagrams of examples of transfer functions produced by a frequency sweep of an input signal (voltage reference signal VREF) of a differential drive-sense circuit (DDSC) of a test container. FIG. 29A depicts a gain vs. frequency bode plot of the transfer function of a constant $H(s)=C$. A bode plot allows for frequency response information to be displayed graphically (on a s-plane) via two separate plots (one for gain and one for phase) both of which are plotted against frequency on a logarithmic horizontal axis. As shown, the transfer function of a constant, $H(s)=C$, is a flat line with a gain of 20 log 10(C) dB. Resistance in the Laplace domain is a constant. A circuit equivalent having this transfer function could be a resistor with a value C in parallel with the output Vout.

FIG. 29B depicts a gain vs. frequency bode plot of the transfer function of a single real pole at the origin, $H(s)=1/s$. When angular frequency $(\omega)=1$ rad/s (10^0 on the logarithmic scale), the gain is also equal to 1 (or 0 dB). The plot has a slope of $-20$ dB/decade. A circuit containing a capacitor in parallel with the output Vout may include a pole at the origin where capacitance has an impedance $1/sC$ in the Laplace domain. s FIG. 29C depicts a gain vs. frequency bode plot of the transfer function of a single real zero at the origin, $H(s)=s$. The plot has a slope of 20 dB/decade. When angular frequency $(\omega)=1$ rad/s (10^0 on the logarithmic scale), the gain is also equal to 1 (or 0 dB). A circuit containing an inductor in parallel with the output Vout may include a zero at the origin where inductance has an impedance sL in the Laplace domain.

FIG. 29D depicts a gain vs. frequency bode plot of the transfer function of a single real pole not at the origin, $$H(s) = \frac{1}{1 + \frac{s}{\omega}}.$$

The pole frequency corresponds to a corner frequency $(\omega c)$ at which the slope of the magnitude curve decreases by 20 dB/decade. At the corner frequency, the output power has dropped to one half of its maximum value (0.707 of the maximum value of the transfer function or $-3$ dB). An RC or LR low pass filter has this form of transfer function. For example, an RC lowpass filter has a transfer function $$H(s) = \frac{\frac{1}{RC}}{s + \frac{1}{RC}}$$

where $\omega c=1/RC$ and LR lowpass filter has a transfer function $$H(s) = \frac{\frac{R}{L}}{s + \frac{R}{L}}$$

where $\omega c=R/L$.

FIG. 29E depicts a gain vs. frequency bode plot of the transfer function of a single real zero not at the origin, $$H(s) = 1 + \frac{s}{\omega}.$$

A real zero becomes the negative of a real pole of a bode plot. The zero frequency corresponds to a corner frequency $(\omega c)$ at which the slope of the magnitude curve increases by 20 dB/decade. At the corner or cutoff frequency, the output power has dropped to one half of its maximum value (0.707 of the maximum value of the transfer function or $-3$ dB).

FIG. 29F depicts a gain vs. frequency bode plot of the transfer function of complex conjugate poles. The pole frequency corresponds to a corner frequency $(\omega c)$ at which the slope of the magnitude curve decreases by 20 dB/decade. Due to the presence of two poles, the magnitude curve decreases by 40 dB/decade. Further, due to the complex nature of the poles, there is a peak at the corner frequency where the sharpness of the peak depends on a damping factor. An LRC circuit where $R<2\sqrt{L/C}$ has this form of transfer function.

Figure 29G:
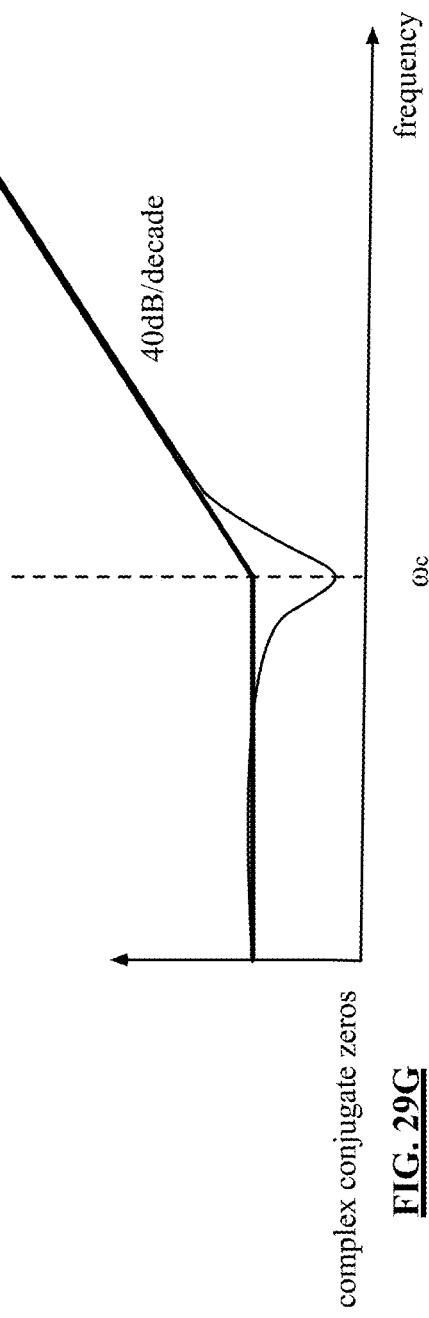

FIG. 29G depicts a gain vs. frequency bode plot of the transfer function of complex conjugate zeros. The zero frequency corresponds to a corner frequency $(\omega c)$ at which the slope of the magnitude curve increases by 20 dB/decade. Due to the presence of two zeros, the magnitude curve increases by 40 dB/decade. Further, due to the complex nature of the zeros, there is a peak at the corner frequency where the sharpness of the peak depends on a damping factor.

Combinations of poles and zeros produce different circuit characteristics. For example, adding a single zero to a single pole system often introduces a high pass characteristic. For example, a CR and a RL high pass filter have a transfer function with a single pole and a single zero. For example, a CR high pass filter has a transfer function $$H(s) = \frac{s}{s + \frac{1}{RC}}$$

where $\omega=1/RC$ and an RL high pass filter has a transfer function $$H(s) = \frac{s}{s + \frac{R}{L}}$$

where $\omega=R/L$. In both cases, the zero at the origin flips the slope of the bode plot (e.g., of FIG. 29D) to make a high pass filter. As another example, an LCR circuit operating as a bandpass filter has a transfer function where $R>2\sqrt{L/C}$. This transfer function has two different real poles and a zero at $s=0$. As such, a circuit equivalent of test container contents can be estimated by analyzing the transfer function.

Figure 30B:
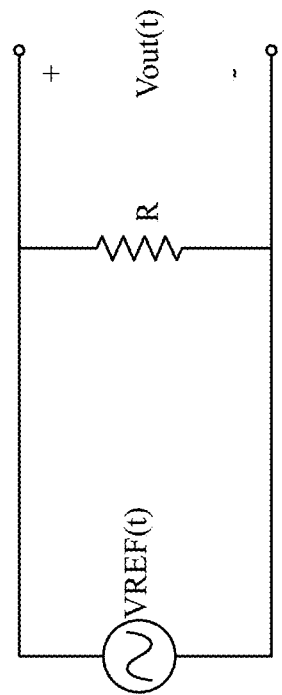
FIGS. 30A-30C are schematic block diagrams of an embodiment of determining a base transfer function of a test container containing a solution in accordance with the present invention.
Figure 30C:
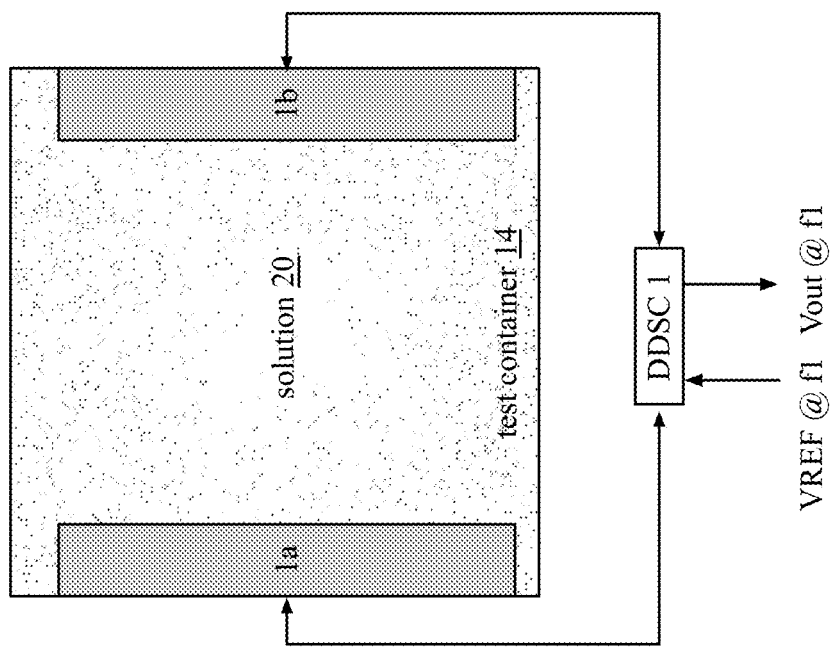
Figure 30A:
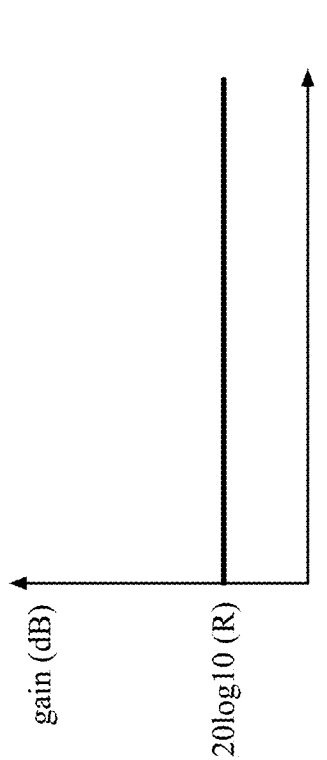

FIGS. 30A-30C are schematic block diagrams of an embodiment of determining a base transfer function of a test container 14 containing a solution 20. FIG. 30A depicts a test container 14 including a differential pair of electrodes 1a and 1b coupled to a "transmit and receive" differential drive sense circuit (DDSC 1). An analog voltage reference signal (VREF) is input to the DDSC 1 and a voltage signal Vout is outputted. The VREF signal includes an oscillating component at a frequency f1 and a DC component. As such, Vout also includes an oscillating component at frequency f1 and a DC component. The Vout signal is representative of contents of the test container 14. The test container 14 includes a solution 20 in this example.

FIG. 30B depicts a bode plot of a transfer function generated by preforming a frequency sweep on the input signal of the test container 14. Here, the transfer function is a flat line having a gain of 20 log 10(R). Therefore the transfer function of the test container solution can be expressed as H(s)=Vout(s)/VREF(s)=R.

FIG. 30C depicts a circuit equivalent of the test container containing the solution 20 based on the transfer function of FIG. 30B. Since the transfer function is a flat line, the solution 20 can be characterized as resistive and has a resistive value of R that can be extracted from the transfer function. Thus the equivalent circuit is VREF(t) in parallel with a resistive value R where the solution has a resistance R.

FIGS. 31A-31C are schematic block diagrams of an embodiment of determining a transfer function of a test container 14 containing a solution 20 and an organic and/or inorganic mass 18. FIG. 31A depicts the test container 14 including a differential pair of electrodes 1a and 1b coupled to a "transmit and receive" differential drive sense circuit (DDSC 1). An analog voltage reference signal (VREF) is input to the DDSC 1 and a voltage signal Vout is outputted. The VREF signal includes an oscillating component at a frequency f1 and a DC component. As such, Vout also includes an oscillating component at frequency f1 and a DC component. The Vout signal is representative of contents of the test container where the contents include a solution 20 and the mass 18 in this example.

FIG. 30B depicts a bode plot of a transfer function generated by preforming a frequency sweep on the input signal of the DDSC 1 of the test container 14. Here, the transfer function has a gain of 20 log 10(R) and at a frequency of ω the slope decreases by 20 dB/decade. Therefore, the transfer function of the test container solution and mass 18 has a single real pole at ω and behaves like a lowpass filter. The base transfer function of the test container solution can be subtracted from this transfer function to provide the transfer function of just the biological material.

FIG. 31C depicts possible circuit equivalents of the test container containing the solution 20 and the mass 18 based on the transfer function of FIG. 31B. With a single real pole, the equivalent circuit could be an LR circuit or an RC circuit as shown. If modeled as an LR circuit, ω equals R/L where R is the resistive component of the mass since the base transfer function representing the solution resistance has been subtracted out. If modeled as an RC circuit, ω equals 1/RC where R is the resistive component of the mass.

To determine which equivalent circuit to use as a model for the mass, assumptions can be made based on known properties of the mass. For example, human cells are primarily capacitive thus the equivalent circuit should include a capacitive element. As another example, additional testing of the mass can be done to determine whether the biological material is primarily capacitive or inductive. For example, an electrical field could be introduced to the test container 14. If the electrical field changes the mass's properties, the mass is primarily capacitive. As another example, a magnetic field could be introduced to the test container 14. If the magnetic field changes the mass's properties, the mass is primarily inductive.

Figure 32B:
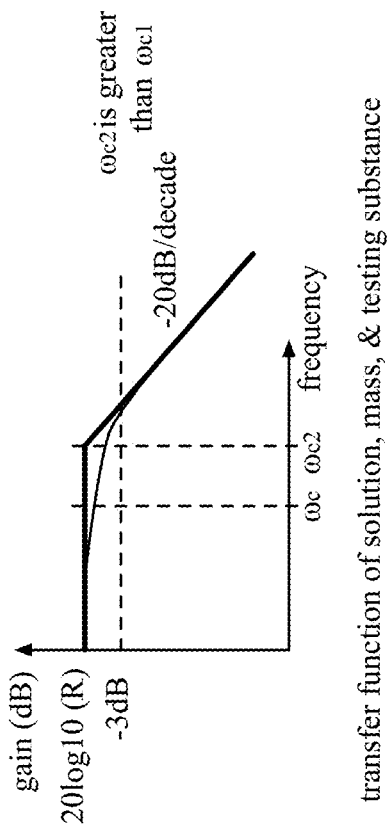
FIGS. 32A-32C are schematic block diagrams of an embodiment of determining a transfer function of a test container containing a solution, an organic and/or inorganic mass, and a testing substance in accordance with the present invention.
Figure 32C:
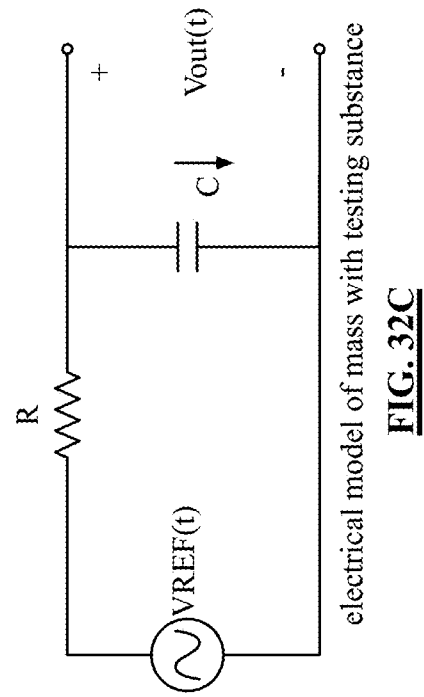
Figure 32A:
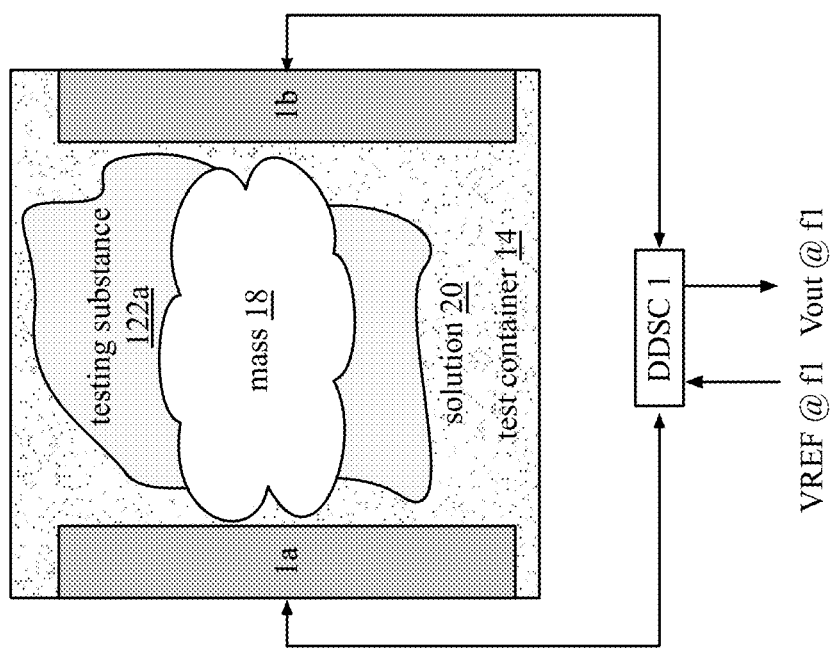

FIGS. 32A-32C are schematic block diagrams of an embodiment of determining a transfer function of a test container 14 containing a solution 20, an organic and/or inorganic mass 18, and a testing substance 122a. FIG. 32A depicts the test container 14 including a differential pair of electrodes 1a and 1b coupled to a "transmit and receive" differential drive-sense circuit (DDSC 1). An analog voltage reference signal (VREF) is input to the DDSC 1 and a voltage signal Vout is outputted. The VREF signal includes an oscillating component at a frequency f1 and a DC component. As such, Vout also includes an oscillating component at frequency f1 and a DC component. The Vout signal is representative of contents of the test container where the contents include a solution 20, the mass 18, and the testing substance 122a in this example.

FIG. 32B depicts a bode plot of a transfer function generated by preforming a frequency sweep on the input signal of the DDSC 1 of the test container 14. Here, the transfer function has a gain of 20 log 10(R) and at a frequency of ω1 the slope decreases by 20 dB/decade (where ω1 is greater than ω of the transfer function of FIG. 31). Therefore, the transfer function of the test container solution 20, mass 18, and the testing substance 122a has a single real pole at ω1 behaves like a lowpass filter. The base transfer function of the test container solution can be subtracted from this transfer function to provide the transfer function of just the mass and the testing substance 122a.

FIG. 32C depicts a circuit equivalent of the test container containing the mass 18 and the testing substance 122a based on the transfer function of FIG. 32B. In FIG. 32C, capacitive properties are assumed or measured, and the equivalent circuit is an RC circuit as shown. Comparing the transfer function of FIG. 31B to the transfer function of FIG. 32B, the corner frequency has increased. Capacitive impedance decreases when frequency increases. As such, the testing substance 122a has caused the capacitive value of the mass 18 to decrease in comparison to the equivalent circuit of the mass 18 of FIG. 31C.

Figure 33B:
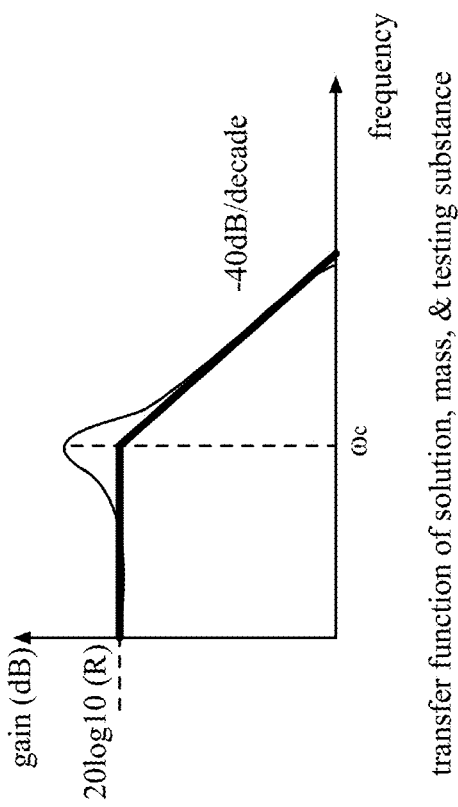
FIGS. 33A-33C are schematic block diagrams of an embodiment of determining a transfer function of a test container containing a solution, an organic and/or inorganic mass, and a testing substance in accordance with the present invention.
Figure 33C:
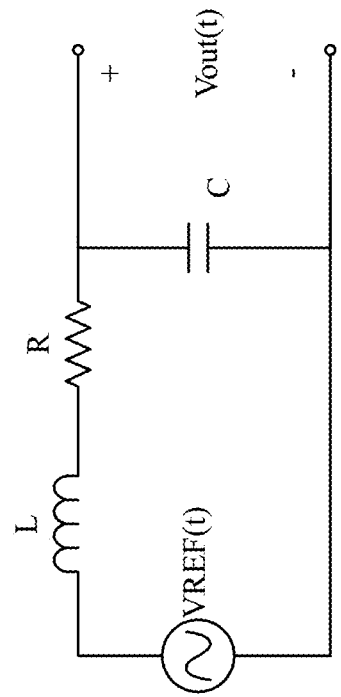
Figure 33A:
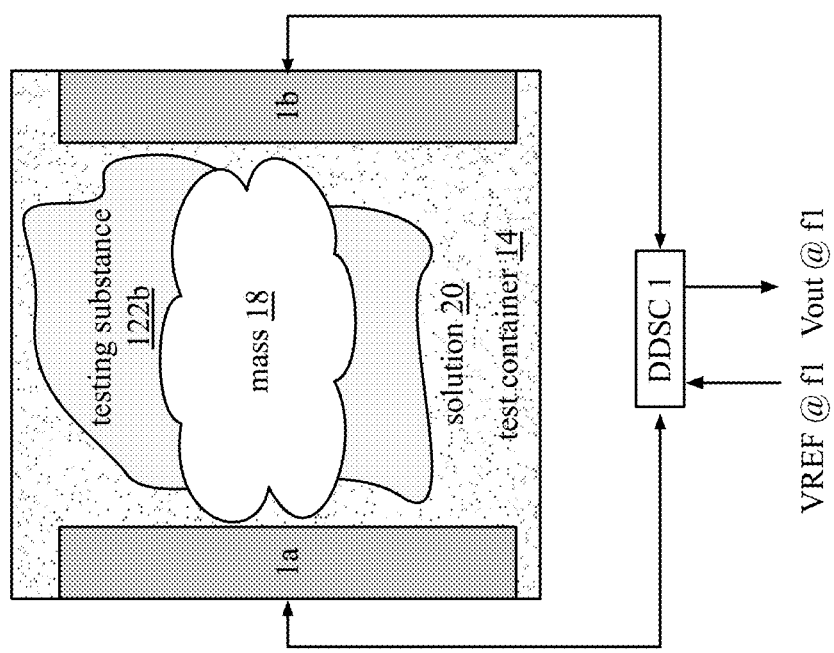

FIGS. 33A-33C are schematic block diagrams of an embodiment of determining a transfer function of a test container 14 containing a solution 20, an organic and/or inorganic mass 18, and a testing substance 122b. FIG. 33A depicts the test container 14 including a differential pair of electrodes 1a and 1b coupled to a "transmit and receive" differential drive-sense circuit (DDSC 1). An analog voltage reference signal (VREF) is input to the DDSC 1 and a voltage signal Vout is outputted. The VREF signal includes an oscillating component at a frequency f1 and a DC component. As such, Vout also includes an oscillating component at frequency f1 and a DC component. The Vout signal is representative of contents of the test container where the contents include a solution 20, the mass 18, and the testing substance 122b in this example.

FIG. 33B depicts a bode plot of a transfer function generated by preforming a frequency sweep on the input signal of the DDSC 1 of the test container 14. Here, the transfer function has a gain of 20 log 10(R) and at a frequency of ω the slope decreases by 40 dB/decade and there is a peak. Therefore, the transfer function of the test container solution 20, mass 18, and the testing substance 122b has complex conjugate poles at oc. The base transfer function of the test container solution can be subtracted from this transfer function to provide the transfer function of just the mass 18 and the testing substance 122*b*.

FIG. 33C depicts a circuit equivalent of the test container containing the mass 18 and the testing substance 122*b* based on the transfer function of FIG. 33B. In FIG. 33C, the equivalent circuit is an RLC circuit where R is less than $2\sqrt{L/C}$ and ω is equal to $1/\sqrt{LC}$. Comparing the transfer function of FIG. 31B to the transfer function of FIG. 33B, there is a peak now at ωc and ωc has a different value. As such, the testing substance 122*b* has caused some resonant behavior in the mass 18.

Figure 34B:
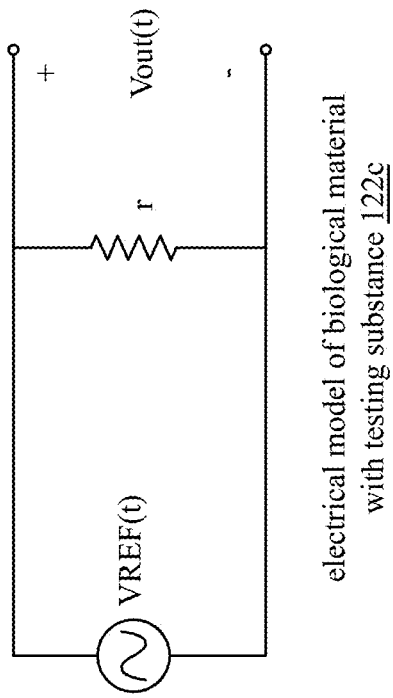
FIGS. 34A-34C are schematic block diagrams of an embodiment of determining a transfer function of a test container containing a solution, an organic and/or inorganic mass, and a testing substance in accordance with the present invention.
Figure 34C:
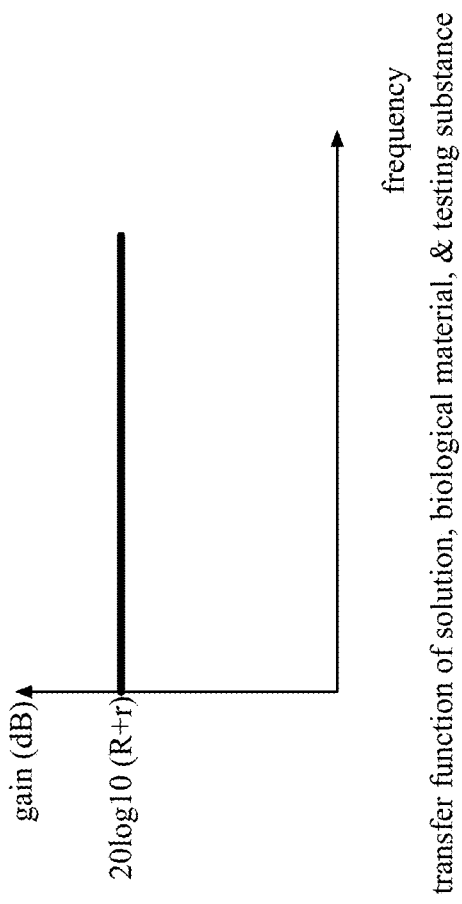
Figure 34A:
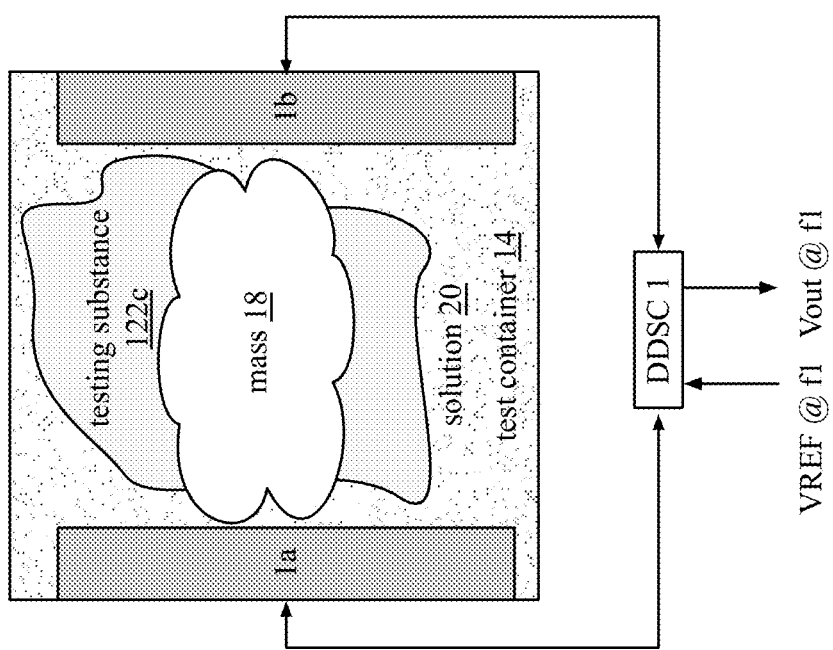

FIGS. 34A-34C are schematic block diagrams of an embodiment of determining a transfer function of a test container 14 containing a solution 20, an organic and/or inorganic mass 18, and a testing substance 122*c*. FIG. 34A depicts the test container 14 including a differential pair of electrodes 1*a* and 1*b* coupled to a "transmit and receive" differential drive-sense circuit (DDSC 1). An analog voltage reference signal (VREF) is input to the DDSC 1 and a voltage signal Vout is outputted. The VREF signal includes an oscillating component at a frequency f1 and a DC component. As such, Vout also includes an oscillating component at frequency f1 and a DC component. The Vout signal is representative of contents of the test container where the contents include a solution 20, the mass 18, and the testing substance 122*c* in this example.

FIG. 34B depicts a bode plot of a transfer function generated by preforming a frequency sweep on the input signal of the DDSC 1 of the test container 14. Here, the transfer function has a gain of 20 log 10(R+r) as shown as a flat line. The base transfer function of the test container solution can be subtracted from this transfer function to provide the transfer function of just the mass 18 and the testing substance 122*c* (e.g., a flat line at 20 log 10(r)).

FIG. 34C depicts a circuit equivalent of the test container containing the mass 18 and the testing substance 122*c* based on the transfer function of FIG. 34B. In FIG. 34C, the equivalent circuit is a resistor (r) in parallel with VREF(t). Comparing the transfer function of FIG. 31B to the transfer function of FIG. 34B, the capacitive and/or inductive behavior of the mass 18 has ceased. For example, the testing substance 122*c* may have killed the mass 18.

Figure 35:
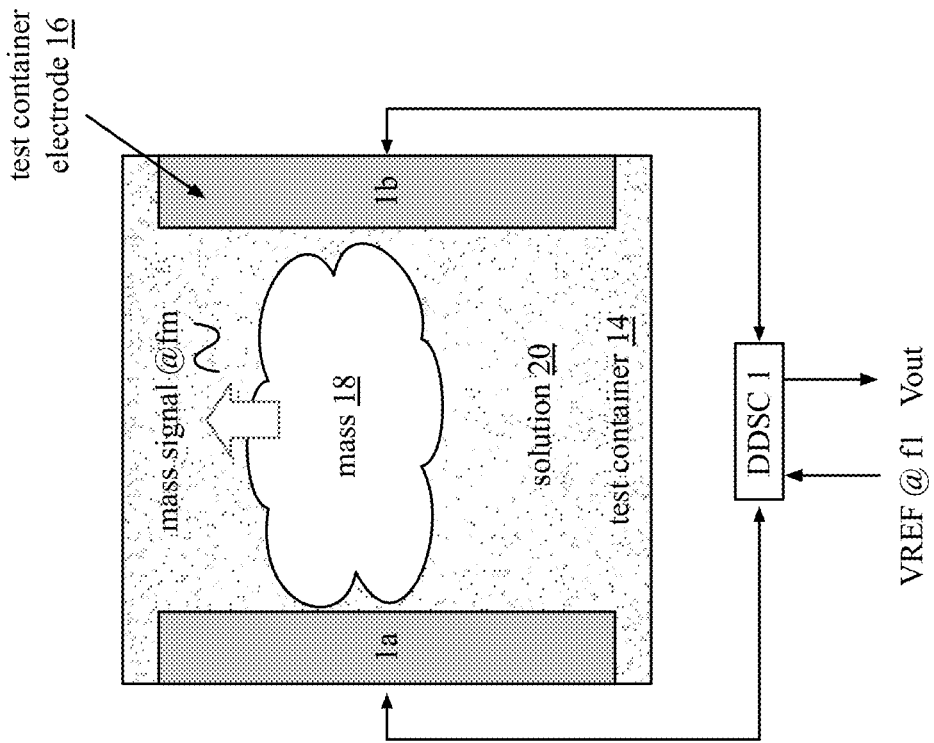
FIG. 35 is a schematic block diagram of an embodiment of a test container including a differential pair of electrodes coupled to a differential drive-sense circuit (DDSC) in accordance with the present invention.

FIG. 35 is a schematic block diagram of an embodiment of a test container 14 including a differential pair of electrodes 1*a* and 1*b* coupled to a "transmit and receive" differential drive-sense circuit (DDSC 1). The DDSC 1 operates similarly to differential drive-sense circuits of previous Figures. An analog voltage reference signal (VREF) is input to the DDSC 1 and a voltage signal Vout is outputted. The VREF signal includes an oscillating component at a frequency f1 and a DC component. As such, Vout also includes an oscillating component at frequency f1 and a DC component. The test container 14 contains a solution 20 and an inorganic or organic mass 18. The mass 18 in this example, produces a signal (e.g., a voltage) at a frequency fm. The Vout signal contains a representation of electrical characteristics of contents of the test container 14.

Figure 36:
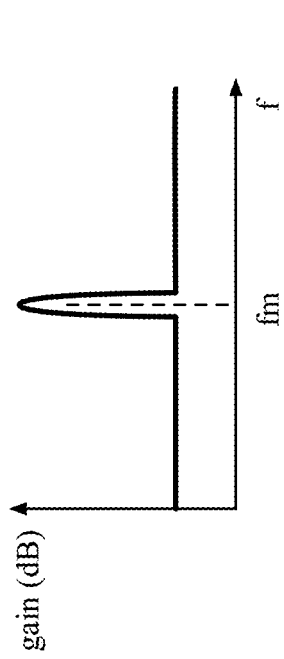
FIG. 36 is a schematic block diagram of an example of a frequency response representation of test container contents of FIG. 35 in accordance with the present invention.

FIG. 36 is a schematic block diagram of an example of a frequency response of Vout when a frequency sweep of the input signal VREF of the test container 14 of FIG. 35 is performed. With the mass 18 producing a mass signal at a frequency fm, the frequency response will show a peak around the frequency fm where the VREF signal at fm combines with the Vmass signal at fm.

In the example of FIG. 36, the mass signal is a sinusoidal voltage signal that results in a pulse in the frequency domain and the impedance of the mass 18 and solution are resistive. In order to capture the desired frequency response at fm, some knowledge of the frequency range of the mass 18 may be required in order to perform the sweep in the desired range. For example, neural tissue can generate oscillatory activity at around 1 Hz to 200 Hz. As such, if the mass is known to be neural tissue, the VREF sweep would need to encompass this frequency range. In another embodiment, the processing module may include a wide bandwidth filter for capturing the signal at fm.

Additionally, a series of frequency sweeps of VREF at different phases can be executed to capture accurate mass signal information. For example, if VREF and the mass signal have opposite phases, signal interference will result in an inaccurate representation of the mass signal. When a phase of VREF is similar to the mass signal, Vout will have an increased magnitude and the frequency response with produce a distinguishable peak at fm.

Figure 37:
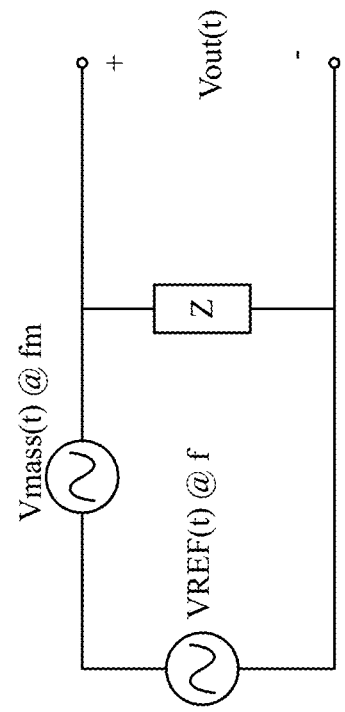
FIG. 37 is a schematic block diagram of an example of a circuit equivalent of the test container of FIG. 35 in accordance with the present invention.

FIG. 37 is a schematic block diagram of an example of a circuit equivalent of the test container 14 of FIG. 35 having a frequency response similar to the example of FIG. 36. The test container 14 can be modeled as a circuit having an alternating current (AC) voltage source VREF(t) (e.g., in the time domain), some unknown impedance attributable to the solution 20 and the mass 18 (Z), and a voltage source at frequency fm attributable to the mass 18. Based on the frequency response of FIG. 36, the impedance Z is resistive and the value of Vmass and frequency fm can be determined.

Figure 38:
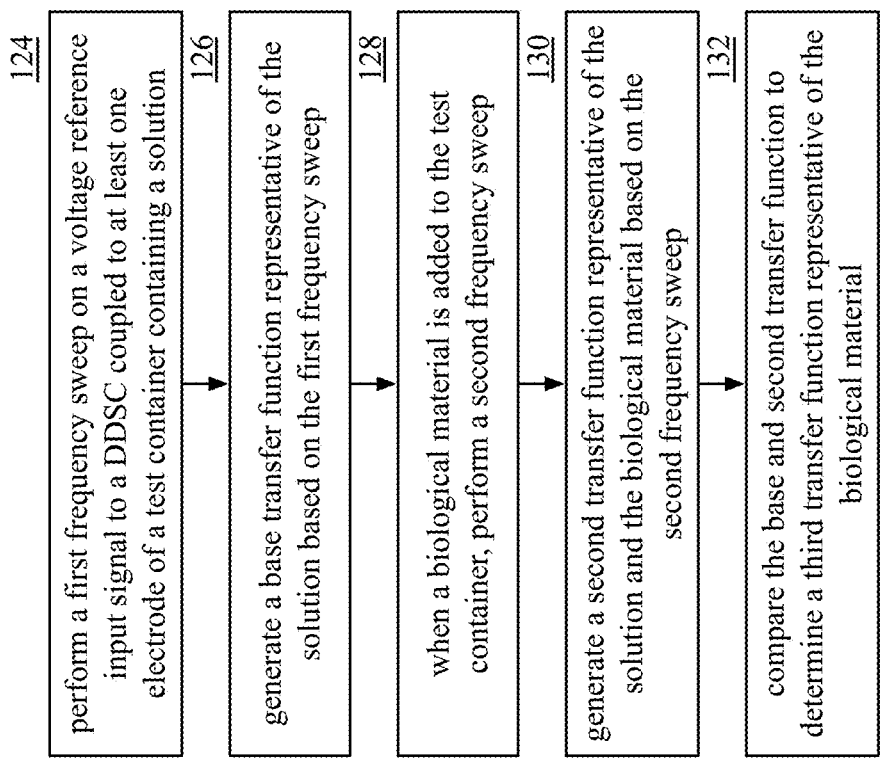
FIG. 38 is a flowchart of an example of a method of generating a transfer function representative of test container contents in accordance with the present invention.

FIG. 38 is a flowchart of an example of a method of generating a transfer function representative of test container contents. The method begins with step 124 where a processing module of an organic and/or inorganic material test system ("test system") performs a first frequency sweep on a voltage reference input signal to at least one differential drive-sense circuit of a test container of the organic and/or inorganic material test system. The organic and/or inorganic material test system includes at least one test container where each test container may be coupled to a respective processing module, or where a processing module is coupled to multiple test containers (e.g., a test container array) of the organic and/or inorganic material test system.

The at least one differential drive-sense circuit is coupled to at least one electrode of at least two electrodes embedded in the test container. For example, the at least one differential drive-sense circuit may be the "receive only" differential drive-sense circuit of FIG. 5 coupled to one electrode, the "transmit and receive" differential drive-sense circuit of FIG. 10 coupled to one electrode, or the "transmit and receive" differential drive-sense circuit of FIG. 22 coupled to a differential pair of electrodes. A differential drive-sense circuit is operable to increase a receive component of an electrode signal and eliminate common mode noise thus making the test system very sensitive to changes in electrical characteristics caused by the contents of the test container.

The purpose of the initial frequency sweep is to obtain the base transfer function of the test container containing a solution without the testing subject matter. A transfer function is a mathematical function which theoretically models a device or system's output for each possible input. The term transfer function is also used in frequency domain analysis of systems using transform methods such as a Laplace transform where the amplitude of the output is a function of the frequency of the input signal.

The solution may include a saline solution, a preservative, a cell culture solution, etc., that is electrically conductive. The testing subject matter may include any organic and/or inorganic material. An organic material (e.g., also referred to herein as a "mass") includes living organisms or portions thereof. For example, the organic material includes one or more cells (e.g., an individual cell, multiple cells, tissue, etc.) and/or one or more portions of a cell (e.g., a section of cell membrane). A cell may be from an animal, human, plant, and/or other biological cell and is any type of cell (e.g., heart, brain, neuron, muscle, skin, lung, etc.). An inorganic material includes non-living organisms that produce an electrical characteristic (e.g., voltage, current, impedance, resistance, reactance, etc.) with or without a stimulus.

The voltage reference signal includes a direct current (DC) component and an oscillating component. The frequency sweep involves changing the frequency of the oscillating component of the voltage reference signal within a particular range of interest.

The method continues with step 126 where the processing module generates a base transfer function representative of the solution of the test container based on the first frequency sweep. The transfer function of the circuit equivalent of a test container in the s-domain (i.e., from doing a Laplace transform) is $H(s)$=output signal/input signal or $H(s)$=Vout/VREF where VREF is the voltage reference signal. By conducting a frequency sweep of the input signal VREF, the transfer function related to Vout can be generated, and impedance information of the equivalent circuit can be determined and analyzed.

When an organic and/or inorganic material is added to the test container, the method continues with step 128 where the processing module performs a second frequency sweep on the voltage reference input signal to the at least one differential drive-sense circuit. The method continues with step 130 where the processing module generates a second transfer function representative of the solution and the organic and/or inorganic material based on the second frequency sweep.

The method continues with step 132 where the processing module compares the base transfer function with the second transfer function to determine a third transfer function representative of the organic and/or inorganic material. For example, the processing module subtracts the base transfer function from the second transfer function to obtain the third transfer function.

Figure 39:
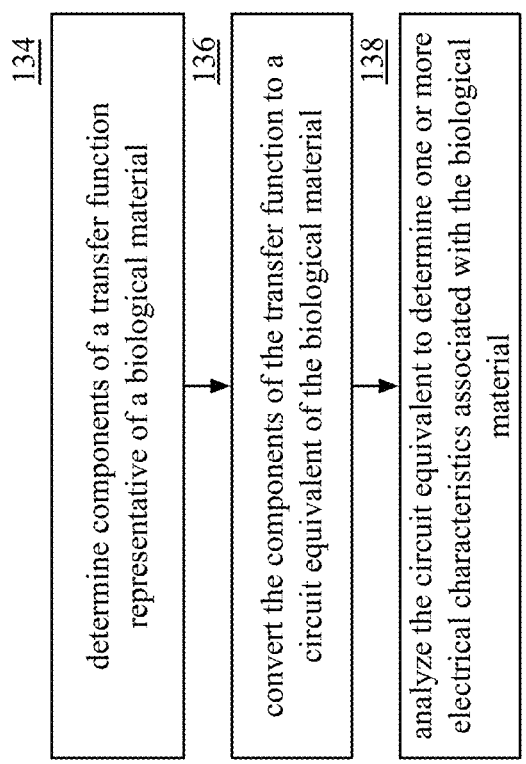
FIG. 39 is a flowchart of an example of a method for analyzing a transfer function to determine information about an organic and/or inorganic material in accordance with the present invention.

FIG. 39 is a flowchart of an example of a method for analyzing a transfer function to determine information about an organic and/or inorganic material. The method begins with step 134 where a processing module of an organic and/or inorganic material test system determines components of a transfer function representative of organic and/or inorganic material of a test container of the organic and/or inorganic material test system. The transfer function is generated by performing one or more frequency sweeps on a voltage reference input signal to at least one differential drive-sense circuit of the test container as discussed with reference to the method of FIG. 38. The at least one differential drive-sense circuit is coupled to at least one electrode of at least two electrodes embedded in the test container.

The method continues with step 136 where the processing module converts the components of the transfer function to a circuit equivalent of the organic and/or inorganic material. For example, all transfer functions have some number of constants, poles and/or zeros at the origin, poles and/or zeros not at the origin, and/or complex poles and/or zeros. Poles of a transfer function are the frequencies (values of s) for which the denominator of the transfer function becomes zero. Zeros of a transfer function are the frequencies (values of s) for which the numerator of the transfer function becomes zero. Depending on the poles, zeros, and/or constants found in the transfer function generated, a circuit equivalent of the test container contents can be generated. For example, on a bode plot, a transfer function of a constant, $H(s)$=C, is a flat line with a gain of 20 log 10(C) dB. A circuit equivalent having this transfer function could be a resistor with a value C in parallel with the output Vout. Resistance in the Laplace domain is a constant.

As another example, on a bode plot, a transfer function having a single real pole not at the origin, with a decreasing slope of 20 dB/decade at a corner frequency may represent an RC or LR lowpass filter. To determine which equivalent circuit to use as a model for the organic and/or inorganic material, assumptions can be made based on known properties of the organic and/or inorganic material. For example, human cells are primarily capacitive thus the equivalent circuit should include a capacitive element. As another example, additional testing of the organic and/or inorganic material can be done to determine whether the organic and/or inorganic material is primarily capacitive or inductive. For example, an electrical field could be introduced to the test container. If the electrical field changes the organic and/or inorganic material's properties, the organic and/or inorganic material is primarily capacitive. As another example, a magnetic field could be introduced to the test container 14. If the magnetic field changes the organic and/or inorganic material's properties, the organic and/or inorganic material is primarily inductive.

The method continues with step 138 where the processing module analyzes the circuit equivalent to determine one or more electrical characteristics associated with the organic and/or inorganic material. For example, when the circuit equivalent of a transfer function is a resistor in parallel with the output, the processing module determines that the organic and/or inorganic material contains resistive properties. As another example, when the circuit equivalent is an LRC circuit, the processing module determines that the organic and/or inorganic material contains a resistive component, a capacitive component, and an inductive component and may have some oscillating behavior. When a testing substance is introduced, the transfer function and resulting equivalent circuit can be analyzed against an equivalent circuit of the organic and/or inorganic material prior to adding the testing substance to determine the electrical effects the testing substance has on the organic and/or inorganic material.

Figure 40:
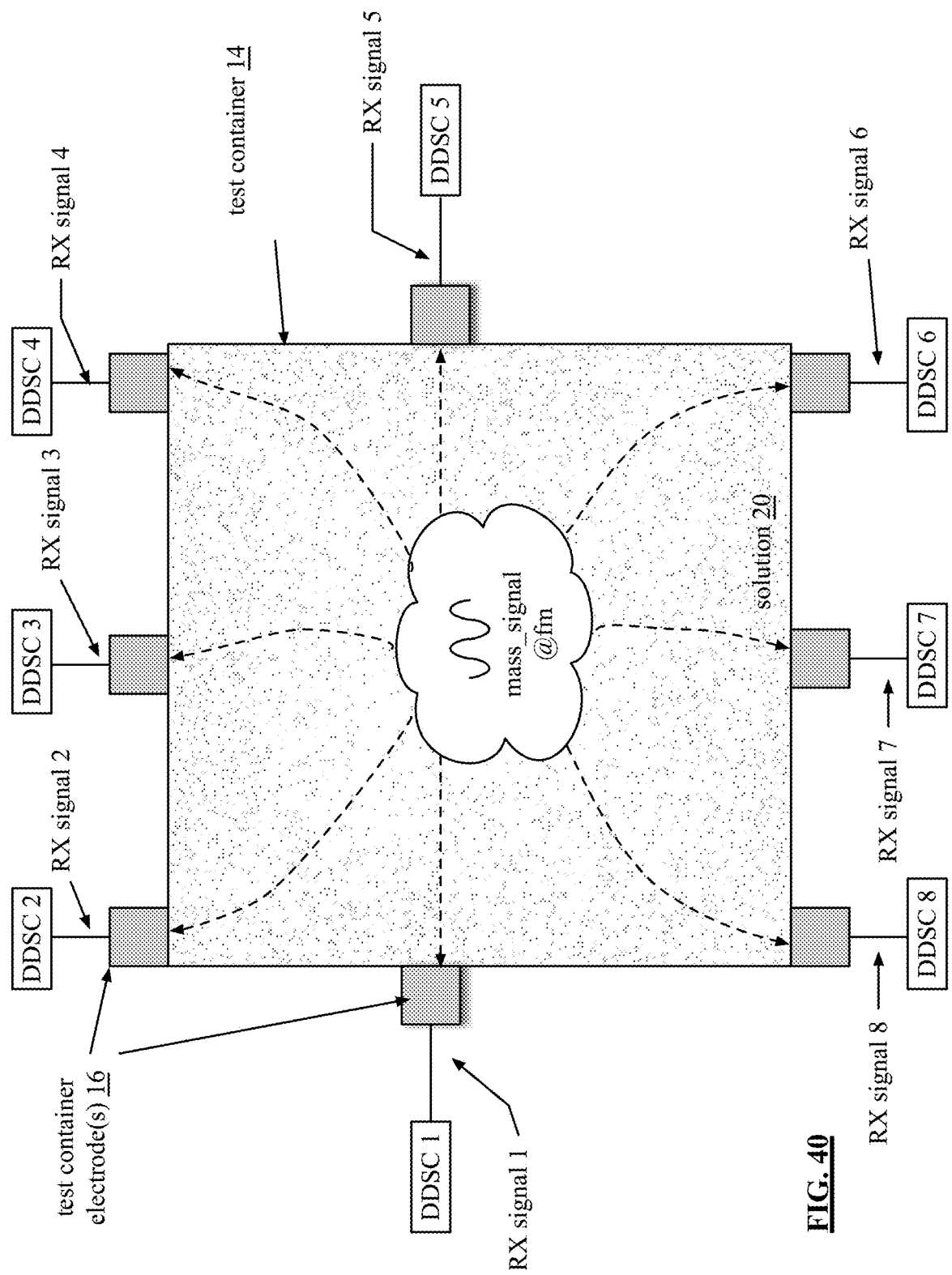
FIG. 40 is a schematic block diagram of an embodiment of passive listening by differential drive-sense circuits (DDSCs) of a test container in accordance with the present invention.

FIG. 40 is a schematic block diagram of an embodiment of passive listening by differential drive-sense circuits (DDSCs) of a test container 14. FIG. 40 includes a test container 14 including eight test container electrodes 16 coupled to differential drive-sense circuits (DDSCs) 1-8 respectively. The DDSCs 1-8 may be "receive only" differential drive-sense circuits or "transmit and receive" differential drive-sense circuits as described in previous Figures.

In this example, the mass 18 is producing an oscillating signal ("mass_signal") at a frequency fm and the DDSCs are in a passive listening mode. To implement a passive listening mode, "receive only" DDSCs operate as described in previous Figures because the transmit signals produced by the "receive only" DDSCs are canceled out. When using "transmit and receive" DDSCs to implement a passive listening mode, the voltage reference signal is a direct current (DC) signal.

As shown, the DDSC 1 receives the RX signal 1, where the RX signal 1 is at frequency fm and includes a representation of the mass_signal with respect to the mass and a test container electrode 1. The DDSC 2 receives the RX signal 2, where the RX signal 2 is at frequency fm and includes a representation of the mass_signal with respect to the mass and a test container electrode 2. The DDSC 3 receives the RX signal 3, where the RX signal 3 is at frequency fm and includes a representation of the mass_signal with respect to the mass and a test container electrode, and so on. As such, the information obtained in the RX signals 1-8 provides information pertaining to mass_signal from the mass and various electrode locations of the test container.

When the frequency range of the mass_signal is unknown, digital filtering circuits coupled to the DDSCs can be centered around different frequency ranges. When a signal is detected, the processing module can adjust the digital filtering circuits to converge on a particular frequency range based on the detected signal. In another embodiment, some of the digital filtering circuits coupled to the DDSCs can be centered around frequency ranges corresponding to fundamental frequencies of a substance and some of the digital filtering circuits coupled to the DDSCs can be centered around frequency ranges corresponding to harmonics of a substance.

Figure 41A:
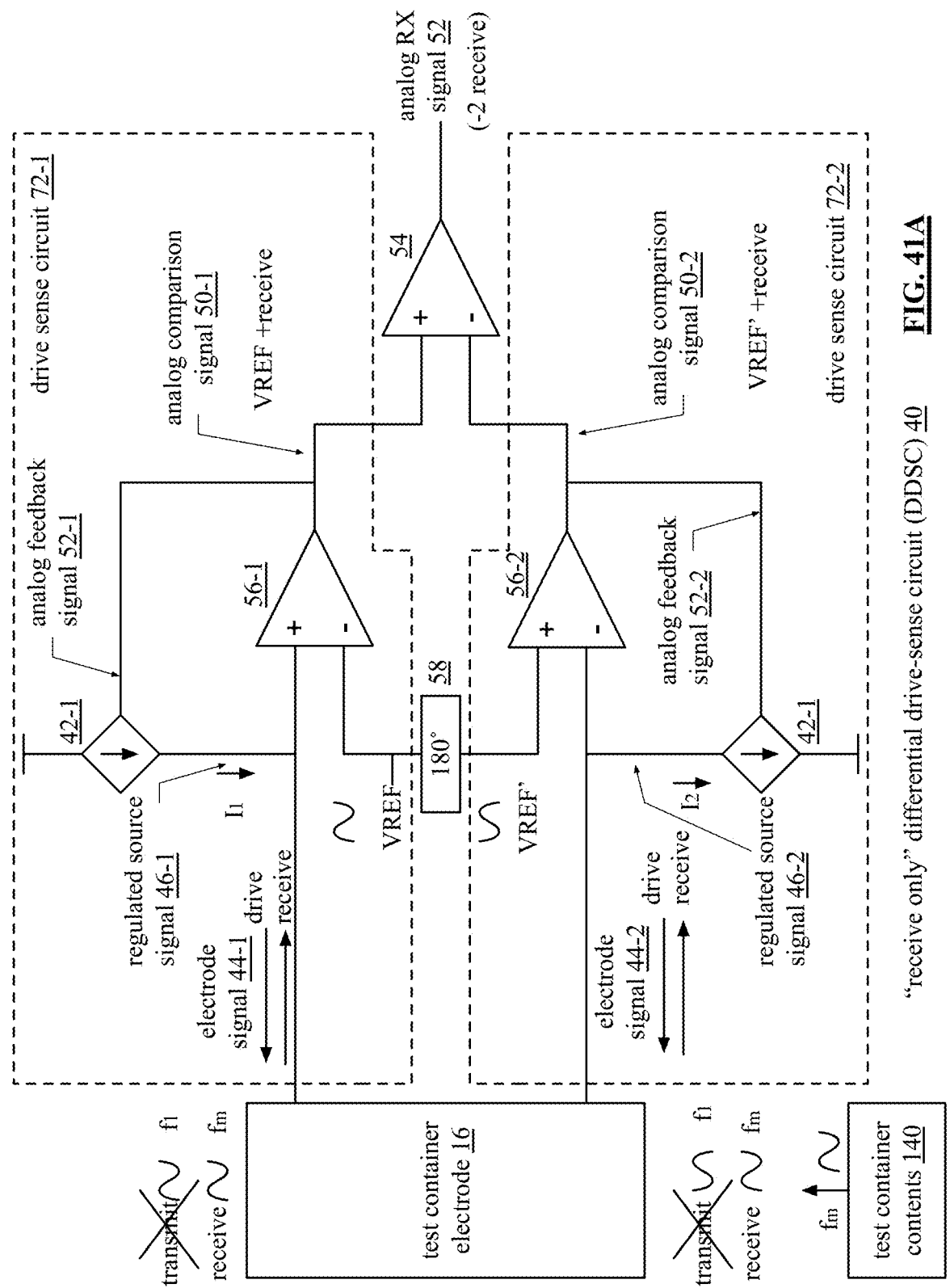
FIGS. 41A-41B are schematic block diagrams of embodiments of differential drive-sense circuits (DDSCs) in a passive listening mode in accordance with the present invention.
Figure 41B:
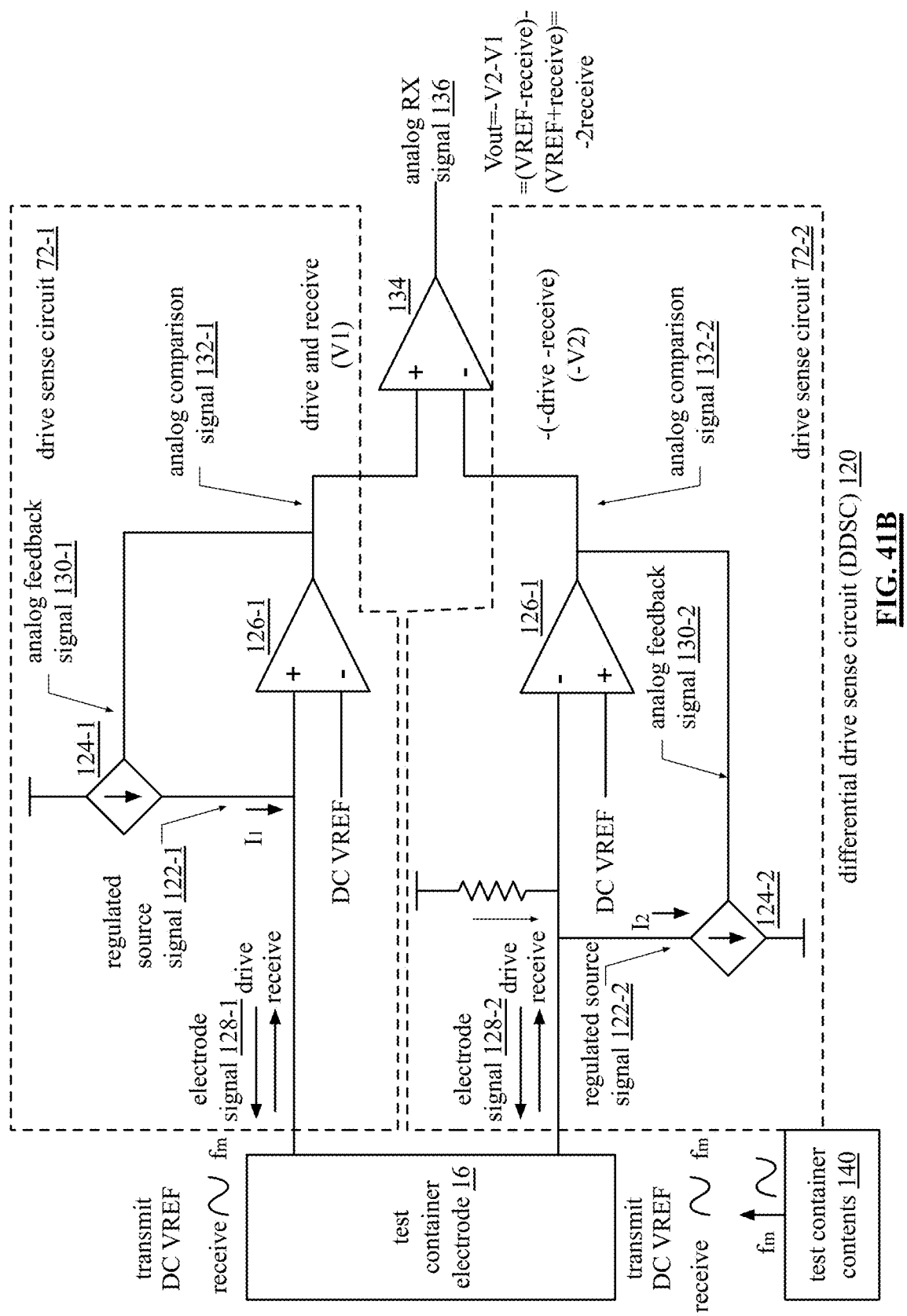

FIGS. 41A-41B are schematic block diagrams of embodiments of differential drive-sense circuits (DDSCs) in a passive listening mode. FIG. 41A is an embodiment of a "receive only" differential drive sense circuit (DDSC) 40 that includes drive-sense circuits 72-1 and 72-2, a 180° phase shifter 58, and an output operational amplifier (op-amp) 54. The "receive only" differential drive sense circuit (DDSC) 40 of FIG. 41A operates similarly to the "receive only" differential drive sense circuit (DDSC) 40 of FIG. 5 except that the receive signal components of electrode signals 44-1 and 44-2 at a frequency fm are produced by test container contents 140 and not by the transmit signal of another circuit of the test container.

The op-amp 56-1 of the drive-sense circuit 72-1 compares the electrode signal 44-1 to the VREF signal having the oscillating component frequency f1 to produce an analog comparison signal 50-1. The analog comparison signal 50-1 contains a representation of the receive signal having the oscillating component frequency fm (e.g., the analog comparison signal 50-1 contains a representation of the VREF signal and the receive signal). The analog comparison signal 50-1 is fed back to the regulated current source circuit 42-1 as analog feedback signal 52-1. The regulated current source circuit 42-1 generates a regulated source signal 46-1 (e.g., a regulated current signal (I1)) based on the analog feedback signal 52-1. The regulated current signal (I1) in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. For example, if the impedance increases the voltage on the electrode, the regulated current signal (I1) provides more current to keep the voltage substantially equal to VREF.

The op-amp 56-2 of the drive-sense circuit 72-2 compares the electrode signal 44-2 to the VREF' signal (the 180° phase shifted VREF signal) having the oscillating component frequency f1 to produce an analog comparison signal 50-2. The analog comparison signal 50-2 contains a representation of the receive signal having the oscillating component frequency fm (e.g., the analog comparison signal 50-2 contains a representation of the VREF' signal and the receive signal). The analog comparison signal 50-2 is fed back to the regulated current source circuit 42-2 as analog feedback signal 52-2. The regulated current source circuit 42-2 generates a regulated source signal 46-2 (e.g., a regulated current signal (I2)) based on the analog feedback signal 52-2. The regulated current signal (I2) in combination with the impedance (Z) of the contents of test container (e.g., solution and/or mass) creates a voltage (V), where V=I*Z. As the impedance (Z) of test container contents changes, the regulated current (I) signal is adjusted to keep the voltage (V) substantially unchanged. For example, if the impedance lowers the voltage on the electrode, the regulated current signal (I2) is increased to keep the voltage substantially equal to VREF'.

The output op-amp 54 compares the analog comparison signal 50-1 and the analog comparison signal 50-2 to produce an analog receive (RX) signal 52. Comparing the analog comparison signal 50-1 and the analog comparison signal 50-2 cancels out the VREF and VREF' components due to the phase and doubles the receive component.

FIG. 41B depicts an embodiment of a "transmit and receive" differential drive-sense circuit (DDSC) 120 that includes drive-sense circuits 72-1 and 72-2 and an output operational amplifier (op-amp) 136. The "transmit and receive" DDSC 120 of FIG. 41B operates similarly to the "transmit and receive" DDSC 120 of FIG. 10 except that the "transmit and receive" DDSC 120 of FIG. 41B, is fed a direct current (DC) voltage reference signal input (e.g., DC VREF) instead of an analog voltage reference signal.

The electrode signals 128-1 and 128-2 include a drive signal component and a receive signal component. The receive signal components correspond to a signal at a frequency fm produced by test container contents 120.

The op-amp 126-1 of the drive-sense circuit 72-1 compares the electrode signal 128-1 to the VREF signal having the DC component to produce an analog comparison signal 132-1. The analog comparison signal 132-1 contains a representation of the receive signal having the oscillating component frequency fm (e.g., the analog comparison signal 132-1 contains a representation of the VREF signal and the receive signal). The analog comparison signal 132-1 is fed back to the regulated current source circuit 124-1 as analog feedback signal 130-1.

The op-amp 126-2 of the drive-sense circuit 72-2 compares the electrode signal 128-2 to the VREF signal having the DC component to produce an analog comparison signal 132-2. The analog comparison signal 132-2 contains a representation of the receive signal having the oscillating component frequency fm (e.g., the analog comparison signal 132-2 contains a representation of the VREF signal and the receive signal). The analog comparison signal 132-2 is fed back to the regulated current source circuit 124-2 as analog feedback signal 130-2.

The output op-amp 134 compares the analog comparison signal 132-1 and the analog comparison signal 132-2 to produce an analog receive (RX) signal 136. Comparing the analog comparison signal 132-1 and the analog comparison signal 132-2 removes the VREF components due to the inverting configuration of the op-amp 126-1 and doubles the receive component.

Figure 42:
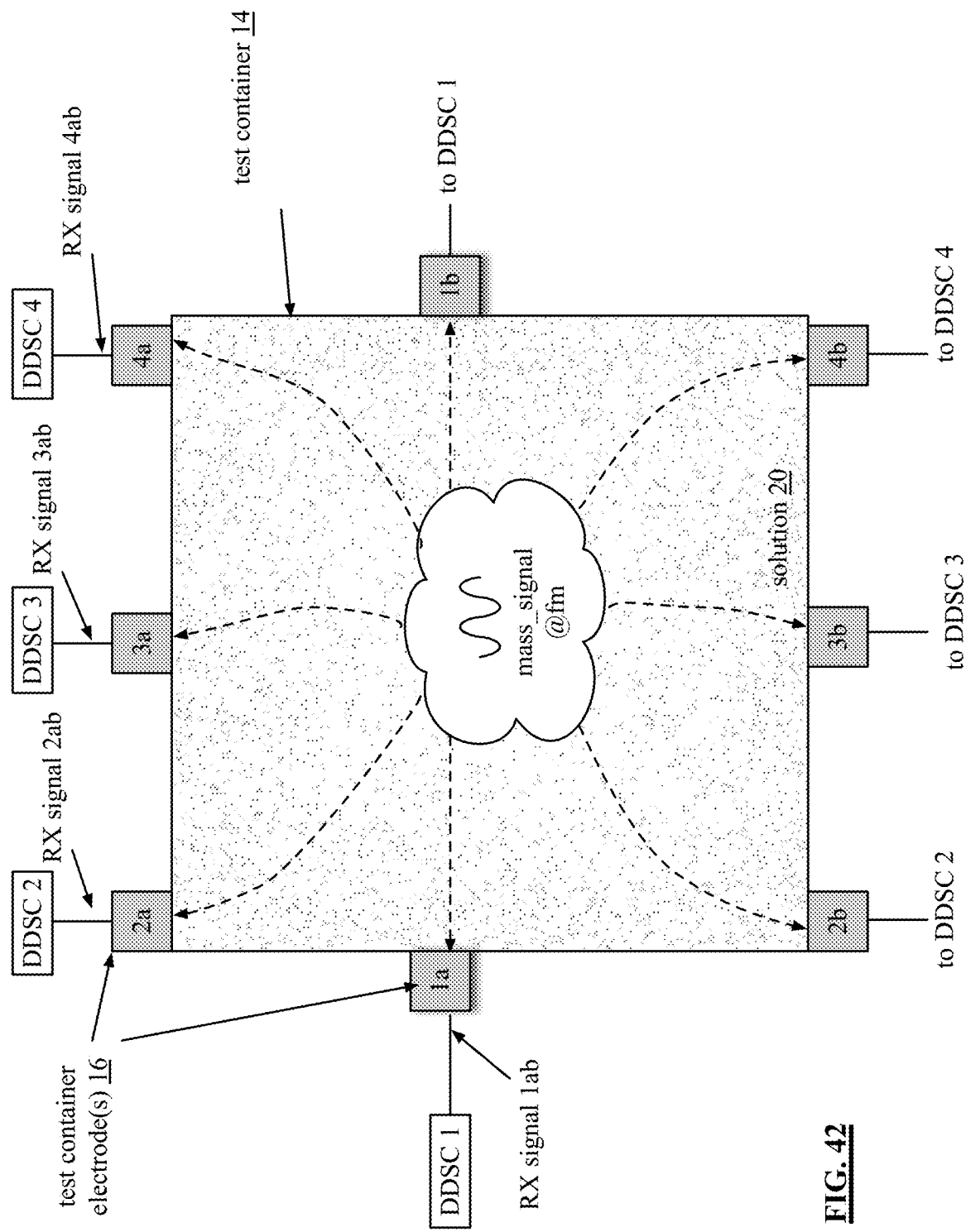
FIG. 42 is a schematic block diagram of an embodiment of passive listening by differential drive-sense circuits (DDSCs) of a test container in accordance with the present invention.

FIG. 42 is a schematic block diagram of an embodiment of passive listening by differential drive-sense circuits (DDSCs) of a test container 14. FIG. 42 includes a test container 14 including four differential pairs of electrodes coupled to differential drive-sense circuits (DDSCs) 1-4 respectively. The DDSCs 1-4 may be "receive only" differential drive-sense circuits and/or "transmit and receive" differential drive-sense circuits as described in previous Figures. The test container 14 contains a solution 20 and mass 18 (e.g., one or more cells, etc.). The example of FIG. 42 operates similarly to the example of FIG. 40 except that differential pairs of electrodes are each connected to a DDSC.

When "receive only" or "transmit and receive" DDSCs are coupled to differential pairs of test container electrodes, the voltage reference signal is a direct current (DC) signal to implement a passive listening mode. As such, any alternating current (AC) disturbances detected are due to the mass_signal.

As shown, the DDSC 1 receives the RX signal 1ab, where the RX signal 1ab is at frequency fm and includes a representation of the mass_signal from electrodes 1a to 1b. The DDSC 2 receives the RX signal 2ab, where the RX signal 2ab is at frequency fm and includes a representation of the mass_signal from electrodes 2a to 2b. The DDSC 3 receives the RX signal 3, where the RX signal 3 is at frequency fm and includes a representation of the mass_signal from electrodes 2a to 2b. The DDSC 4 receives the RX signal 4, where the RX signal 4 is at frequency fm and includes a representation of the mass_signal from electrodes 4a to 4b. As such, the information obtained in the RX signals 1ab-4ab provides information pertaining to mass_signal as it is interpreted between differential pairs of electrodes.

Figure 43:
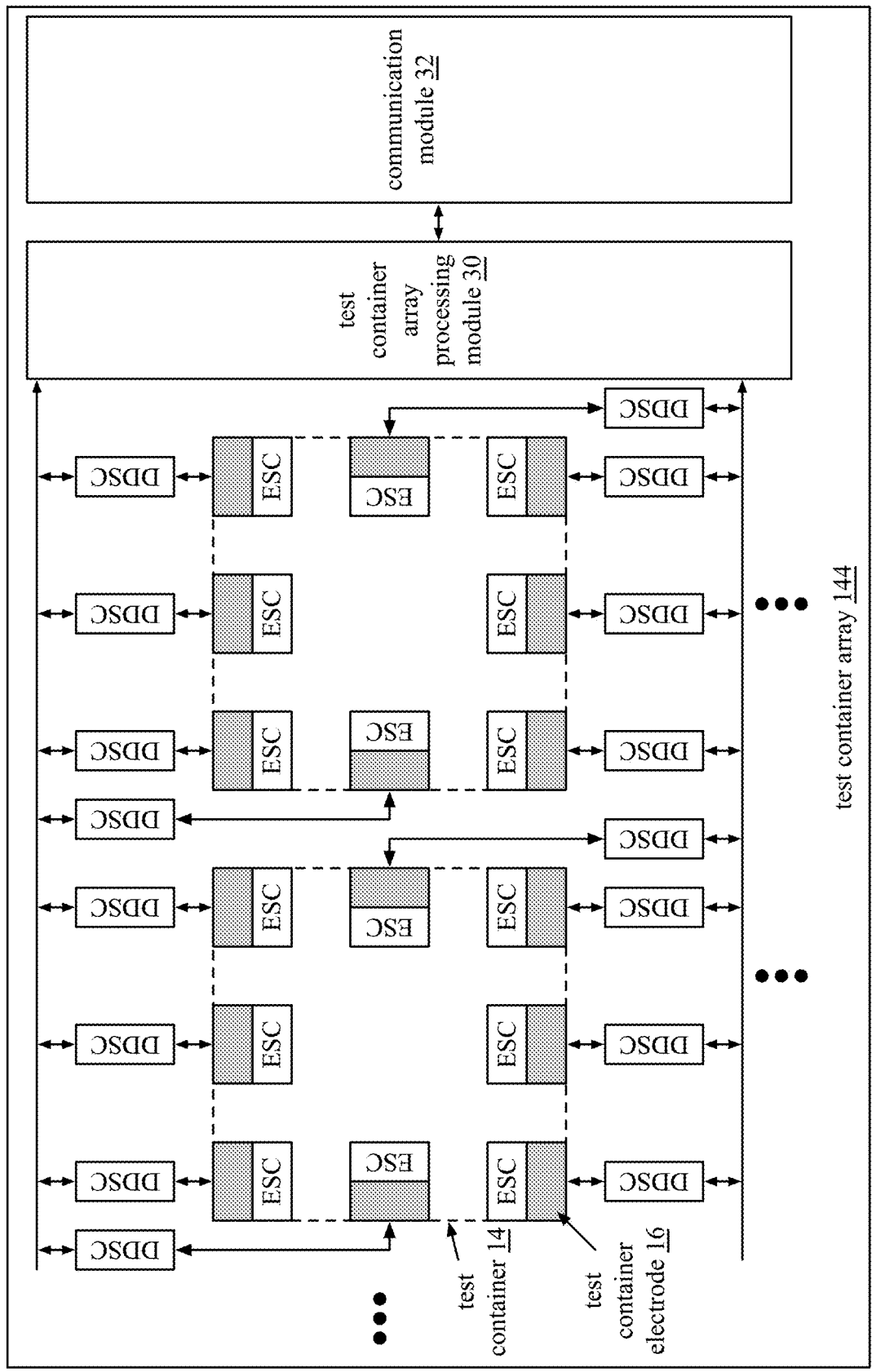
FIG. 43 is a schematic block diagram of an embodiment of a reactive material test system in accordance with the present invention.

FIG. 43 is a schematic block diagram of an embodiment of a reactive material test system 142 that includes a test container array 144 including at least one test container 14, a plurality of test container electrodes 16 (i.e., at least two test container electrodes), a plurality of energy to signal converters (ESCs), a plurality of differential drive sense circuits (DDSCs), a test container array processing module 30, and a communication module 32. The reactive material test system 142 of FIG. 43 operates similarly to the test systems of previous Figures except for the addition of the energy to signal converters (ESCs) which are incorporated into the test system to detect various conditions and/or characteristics of reactive materials. Reactive materials include any combination of organic and/or inorganic materials that have reactive properties that produce some form of energy such as a chemical reaction between two or more materials, a chemical reaction between a material and a catalyst, a chemical reaction between a material and stimulus, combustible materials, etc.

An energy to signal converter converts energy from one form to another. For example, a thermocouple is an energy to signal converter that changes temperature differences into an electric voltage signal. As another example, a pressure sensor generates a signal as a function of pressure imposed. As another example, a vibration powered generator is a type of electric generator that converts kinetic energy from vibration into electrical energy. Other types of energy to signal converter include pH probes, hydrogen sensors, air flow sensors, accelerometers, photodiodes, transducers, etc.

The energy to signal converters convert a condition detected in the test container to an electrical signal on an electrode. Depending on the materials being tested, a combination of various types of ESCs may be included in the test container to obtain different information about the test container contents. The test container electrodes 16 are each coupled to a differential drive-sense circuit (DDSCs). The DDSCs are operable to detect very small changes in electrical characteristics of the test container electrodes 16 caused by the signals provided by the energy to signal converters.

The DDSCs provide the detected changes in electrical characteristics of the test container electrodes 16 (i.e., sensed signals, analog receive signals, etc.) to the test container array processing module 30. In another embodiment, a processing module is coupled to each test container (e.g., a test container processing module). The test container array processing module 30 (i.e., the processing module) is described in greater detail at the end of the detailed description of the invention section. The test container array processing module 30 processes the detected changes in electrical characteristics of the test container electrodes 16 from the DDSCs to determine the characteristics of reactive materials of the test system 10. For example, the test container array processing module 30 filters the data (e.g., via one or more bandpass filters) received from the DDSCs interprets the filtered data to determine energy values (e.g., temperature changes, pressure changes, etc.) caused by the reactive materials of the test container 14.

Figure 44:
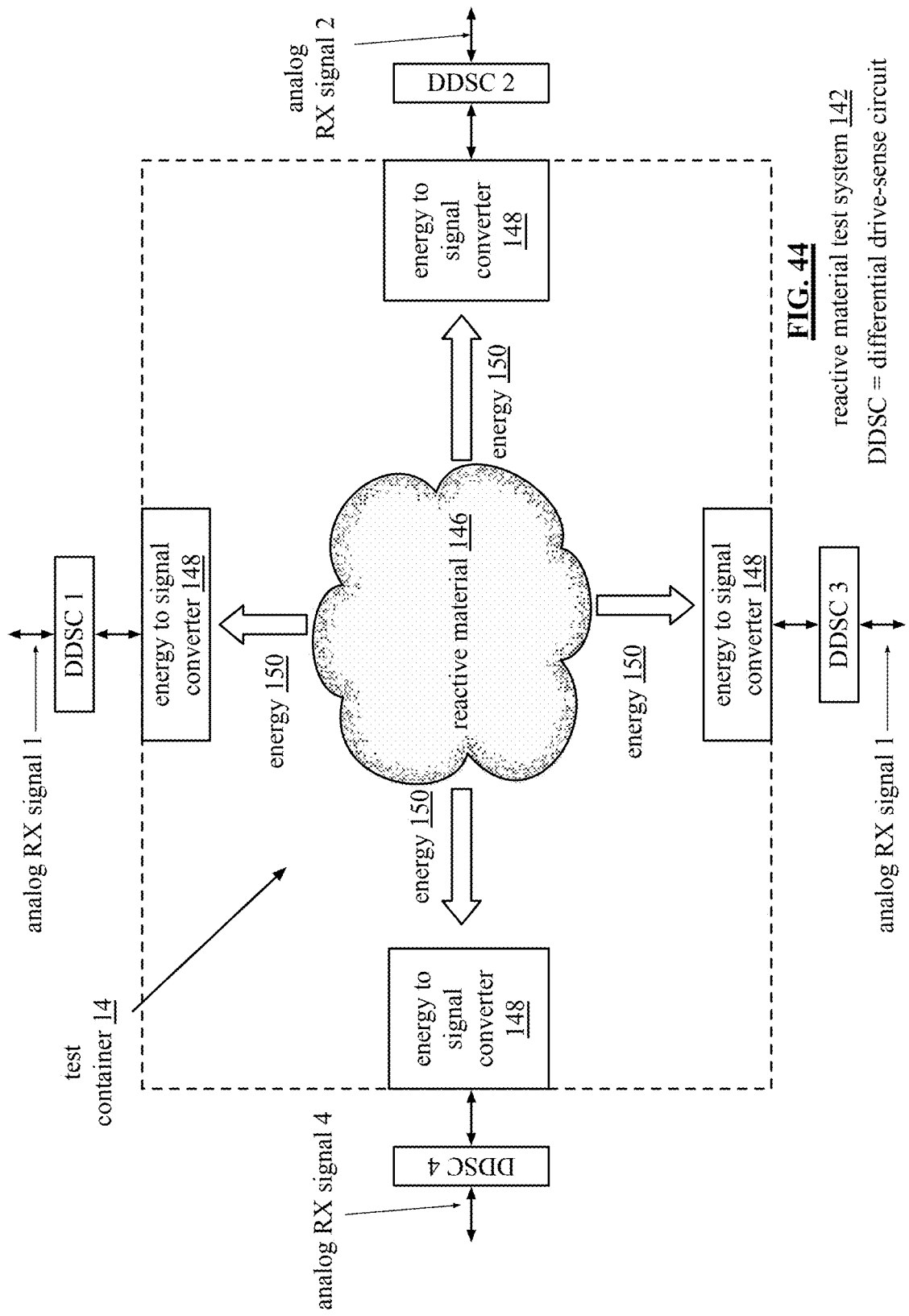
FIG. 44 is a schematic block diagram of an embodiment of a test container of a reactive material test system in accordance with the present invention.

FIG. 44 is a schematic block diagram of an embodiment of a test container 14 of a reactive material test system 142 that includes a plurality of energy to signal converters (ESCs) 148 and a plurality of differential drive sense circuits (DDSCs) 1-4. The reactive material test system 142 of FIG. 44 operates similarly to the reactive material test system 142 of FIG. 43 except that due to the nature of the testing and the energy to signal converters 148, electrodes are not needed. For example, when the energy to signal converters (ESCs) 148 are transducers operable to convert vibrations into electrical signals, the energy to signal converters (ESCs) 148 may be directly coupled to the DDSCs 1-4.

Here, the reactive material 146 (e.g., a chemical reaction) is releasing energy 150. The energy is converted by the energy to signal converters (ESCs) 148 into electrical signals which are communicated to the DDSCs 1-4. The DDSCs are operable to detect very small electrical signals produced by the ESCs.

The DDSCs provide electrical signals representative of energy to the test container array processing module 30 as analog receive (RX) signals 1-4 (or digital sensed signals when the DDSCs include analog to digital converters). In another embodiment, a processing module is coupled to each test container (e.g., a test container processing module). The test container array processing module 30 (i.e., the processing module) is described in greater detail at the end of the detailed description of the invention section. The test container array processing module 30 processes the analog receive (RX) signals 1-4 to determine electrical characteristics of reactive materials of the test system 142.

Figures 45A, 45B, 45C:
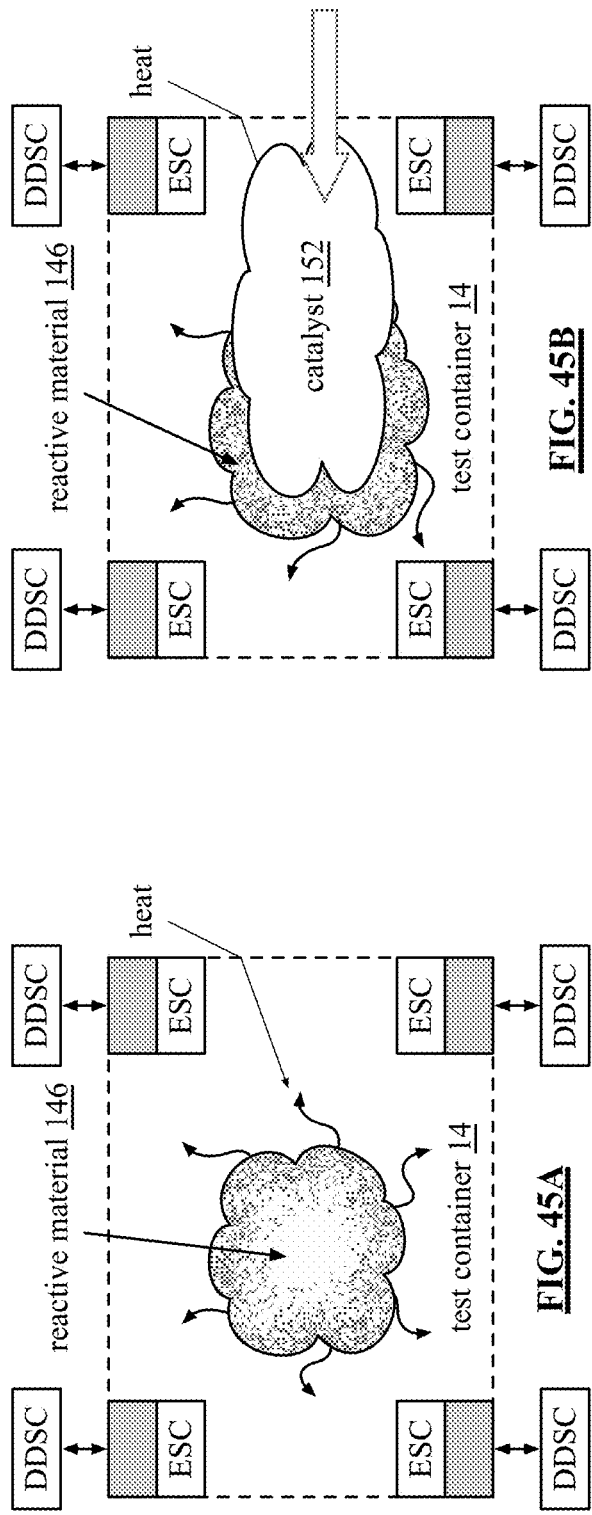
FIGS. 45A-45C are schematic block diagrams of an embodiment of a test container of a reactive material test system in accordance with the present invention.

FIGS. 45A-45C are schematic block diagrams of an embodiment of a test container 14 of a reactive material test system. In FIGS. 45A-45B the energy to signal converters are thermocouples that are operable to convert temperature changes to voltage signals. In FIG. 45A, a reactive material 146 is present in the test container 14 and is emitting an amount of heat that is detected by the DDSCs via the ESCs. For example, the reactive material 146 is hydrogen peroxide. Hydrogen peroxide decomposes into water and oxygen gas. The decomposition emits some amount of heat that is converted to an electrical signal by the energy to signal converters (ESCs) and detected by the differential drive-sense circuits (DDSCs).

In FIG. 45B, a catalyst 152 is added to the test container 14. For example, the catalyst 152 is potassium permanganate. In FIG. 45C, the reactive material 146 reacts with the catalyst 152 which produces heat. For example, the potassium permanganate catalyst speeds up the decomposition of hydrogen peroxide causing a chemical reaction that produces a lot of heat and water vapor. The emitted heat is converted to electrical signals by the energy to signal converters (ESCs) and detected by the differential drive-sense circuits (DDSCs). The detected heat before and after the catalyst was added can by analyzed to determine information about the reactive material 146.

As may be used herein, one or more claims may include, in a specific form of this generic form, the phrase "at least one of a, b, and c" or of this generic form "at least one of a, b, or c", with more or less elements than "a", "b", and "c". In either phrasing, the phrases are to be interpreted identically. In particular, "at least one of a, b, and c" is equivalent to "at least one of a, b, or c" and shall mean a, b, and/or c. As an example, it means: "a" only, "b" only, "c" only, "a" and "b", "a" and "c", "b" and "c", and/or "a", "b", and "c".

As may also be used herein, the terms "processing module", "processing circuit", "processor", "processing circuitry", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, processing circuitry and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with one or more other routines. In addition, a flow diagram may include an "end" and/or "continue" indication. The "end" and/or "continue" indications reflect that the steps presented can end as described and shown or optionally be incorporated in or otherwise used in conjunction with one or more other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While the transistors in the above described figure(s) is/are shown as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid-state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. An organic and inorganic material test system comprises:
   at least one test container;
   a first and second set of electrodes embedded in the at least one test container;
   a set of transmit circuits coupled to the first set of electrodes, wherein a first transmit circuit of the set of transmit circuits is coupled to a first electrode of the first set of electrodes, wherein the first electrode of the first set of electrodes is embedded in a first test container of the at least one test container, wherein the first transmit circuit is operable to produce a first transmit signal at a first frequency for transmission through contents of the first test container; and
   a set of differential drive-sense circuits coupled to the second set of electrodes, wherein a first differential drive-sense circuit of the set of differential drive-sense circuits is coupled to a second electrode of the second set of electrodes, wherein the second electrode is embedded in the first test container, and wherein the first differential drive-sense circuit of the set of differential drive-sense circuits includes:
   a pair of drive-sense circuits, wherein a first drive-sense circuit of the pair of drive-sense circuits is operable to:
   generate a second transmit signal at a second frequency on the second electrode of the second set of electrodes; and
   generate a first receive signal based on the first transmit signal at the first frequency; and
   wherein a second drive-sense circuit of the pair of drive-sense circuits is operable to:
   generate a third transmit signal at the second frequency on the second electrode; and
   generate a second receive signal based on the first transmit signal at the first frequency; and
   an output operational amplifier coupled to the pair of drive-sense circuits, wherein the output operational amplifier is operable to:
   compare the first and second receive signals to produce an analog receive signal, wherein the analog receive signal has a greater magnitude than a magnitude of the first or second receive signals, and wherein the analog receive signal includes a representation of electrical characteristics of the contents of the first test container with respect to positioning of the first electrode of the first set of electrodes and second electrode of the second set of electrodes.

2. The organic and inorganic material test system of claim 1 further comprises:
   a processing module coupled to the set of transmit circuits and the set of differential drive-sense circuits, wherein the processing module is operable to:
   provide an analog voltage reference signal to the first differential drive-sense circuit of the set of differential drive-sense circuits, wherein the analog voltage reference signal includes a direct current (DC) component and an oscillating component at the second frequency on the second electrode;
   receive the analog receive signal from the first differential drive-sense circuit of the set of differential drive-sense circuits; and
   interpret the analog receive signal to determine the electrical characteristics of the contents of the first test container.

3. The organic and inorganic material test system of claim 2, wherein the processing module is operable to interpret the analog receive signal by:
   converting the analog receive signal to an impedance value.

4. The organic and inorganic material test system of claim 3 further comprises:
   obtaining other analog receive signals from other differential drive-sense circuits of the first test container;
   converting the other analog receive signals to other impedance values; and
   generating an impedance map representative of the contents of the first test container based on the impedance value and the other impedance values.

5. The organic and inorganic material test system of claim 4 further comprises:
   a communication module operably coupled to the processing module, wherein the communication module is operable to output one or more of:
   the impedance value;
   the other impedance values;
   the analog receive signal;
   the other analog receive signals; and
   the impedance map.

6. The organic and inorganic material test system of claim 1 further comprises:
   wherein the first drive-sense circuit of the pair of drive-sense circuits includes:
   a first operational amplifier (op-amp) coupled to the second electrode, wherein the first op-amp is operable to compare an analog voltage reference signal to an electrode signal of the second electrode to produce the first receive signal at the first frequency, wherein the electrode signal of the second electrode includes a first drive component and a first receive component, wherein the first receive signal includes a representation of the first drive component and the first receive component, and wherein the first receive component is representative of the electrical characteristics of the contents of the first test container with respect to the positioning of the first electrode of the first set of electrodes and second electrode of the second set of electrodes; and a first voltage controlled current source coupled to the output of the first op-amp and a first input of the first op-amp, wherein the first voltage controlled current source is operable to generate the first drive component based on the first receive signal such that the inputs of the first op-amp remain substantially equal; and wherein the second drive-sense circuit of the pair of drive-sense circuits includes:

a second operational amplifier (op-amp) coupled to the second electrode of the second set of electrodes, wherein the second op-amp is operable to compare the analog voltage reference signal to the electrode signal of the second electrode to produce the second receive signal at the first frequency, wherein the electrode signal of the second electrode includes a second drive component and a second receive component, wherein the second receive signal includes a representation of the second drive component and the second receive component, and wherein the second receive component is representative of the electrical characteristics of the contents of the first test container with respect to the positioning of the first electrode of the first set of electrodes and second electrode of the second set of electrodes; and a second voltage controlled current source coupled to the output of the second op-amp and a first input of the second op-amp, wherein the second voltage controlled current source is operable to generate the second drive component based on the second receive signal such that the inputs of the second op-amp remain substantially equal.

7. The organic and inorganic material test system of claim 6 further comprises:

the first op-amp is a non-inverting op-amp; and
the second op-amp is an inverting op-amp.

8. The organic and inorganic material test system of claim 1 further comprises:

wherein the second drive-sense circuit is a mirror image of the first drive-sense circuit; and
wherein the first differential drive-sense circuit further includes:
a phase shifter coupled to an input of the second drive-sense circuit, wherein the phase shifter is operable to shift an oscillating component of an analog voltage reference signal by 180 degrees to produce a phase shifted analog voltage reference signal, wherein the analog voltage reference signal is provided to the first drive-sense circuit, and wherein the phase shifted analog voltage reference signal is provided to the second drive-sense circuit.

9. The organic and inorganic material test system of claim 1, wherein the first transmit circuit of the set of transmit circuits includes one of:

a drive-sense circuit; and
another differential drive-sense circuit.

10. The organic and inorganic material test system of claim 1 further comprises:

wherein the first electrode of the first set of electrodes is shaped to cover a first area of a perimeter of the first test container; and
wherein the second electrode of the second set of electrodes is shaped to cover an opposite area to first area.

11. The organic and inorganic material test system of claim 1, wherein the contents of the first test container include one or more of:

a solution;
an organic material;
an inorganic material; and
a testing substance.

* * * * *